US010882886B2

(12) United States Patent
Hallwirth et al.

(10) Patent No.: US 10,882,886 B2
(45) Date of Patent: Jan. 5, 2021

(54) ADENO-ASSOCIATED VIRUS POLYNUCLEOTIDES, POLYPEPTIDES AND VIRIONS

(71) Applicants: Children's Medical Research Institute, Westmead (AU); The Sydney Children's Hospitals Network (Randwick and Westmead) (incorporating The Royal Alexandra Hospital For Children), Westmead (AU); The United States of America, as represented by the Secretary, Department of Health and Human Services, Bethesda, MD (US)

(72) Inventors: Claus Hallwirth, Parramatta (AU); Ian Alexander, Pennant Hills (AU); Richard Smith, Germantown, MD (US); Robert Kotin, Bethesda, MD (US)

(73) Assignees: CHILDREN'S MEDICAL RESEARCH INSTITUTE, Westmead (AU); THE SYDNEY CHILDREN'S HOSPITALS NETWORK (RANDWICK AND WESTMEAD) (INCORPORATING THE ROYAL ALEXANDRA HOSPITAL FOR CHILDREN), Westmead (AU); THE UNITED STATES OF AMERICA, AS REPRESENTED BY THE SECRETARY, DEPARTMENT OF HEALTH AND HUMAN SERVICES (WASHINGTON DC), Bethesda, MD (US)

( * ) Notice: Subject to any disclaimer, the term of this patent is extended or adjusted under 35 U.S.C. 154(b) by 0 days.

(21) Appl. No.: 16/098,810

(22) PCT Filed: May 3, 2017

(86) PCT No.: PCT/US2017/030808
§ 371 (c)(1),
(2) Date: Nov. 2, 2018

(87) PCT Pub. No.: WO2017/192699
PCT Pub. Date: Nov. 9, 2017

(65) Prior Publication Data
US 2019/0135870 A1 May 9, 2019

Related U.S. Application Data

(60) Provisional application No. 62/331,188, filed on May 3, 2016.

(51) Int. Cl.
| | | |
|---|---|---|
| C07K 14/005 | (2006.01) | |
| C07K 14/015 | (2006.01) | |
| C12N 15/86 | (2006.01) | |
| C12N 15/10 | (2006.01) | |
| A61K 38/00 | (2006.01) | |
| A61K 48/00 | (2006.01) | |

(52) U.S. Cl.
CPC ........ C07K 14/005 (2013.01); C12N 15/1093 (2013.01); C12N 15/86 (2013.01); *A61K 38/00* (2013.01); *A61K 48/00* (2013.01); *C07K 2319/00* (2013.01); *C12N 2750/14121* (2013.01); *C12N 2750/14122* (2013.01); *C12N 2750/14133* (2013.01); *C12N 2750/14143* (2013.01); *C12N 2750/14152* (2013.01)

(58) Field of Classification Search
CPC ...... C12N 15/8645; C12N 2750/14344; A61K 39/23; G01N 33/9406
See application file for complete search history.

(56) References Cited

U.S. PATENT DOCUMENTS 9,186,419 B2 11/2015 Xiao
2015/0240226 A1 8/2015 Mathur et al.

FOREIGN PATENT DOCUMENTS

WO WO 2004/112727 A2 12/2004

OTHER PUBLICATIONS

Extended European Search Report, dated Sep. 2, 2019, in European Application No. EP 17 79 3239.9.
Baillie, G.J. et al. 2001 "Endogenous Type D Retrovirus in a Marsupial, the Common Brushtail Possum (*Trichosurus vulpecula*)" *J. Virol* 75: 2499-2507.
Bellaganahalli, M.N. et al. 2014 "Full Genome Characterization of the *Culicoides*-Borne Marsupial Orbiviruses: Wallal Virus, Mudjinbarry Virus and Warrego Viruses" *PLOS One* 9: e108379.
Hallwirth, C.V. et al. 2015 "Discovery of ancient and contemporary adeno-associated viruses from Australian marsupials" *The Journal of Gene Medicine* 17: p. 183 (Abstract).

*Primary Examiner* — Bao Q Li
(74) *Attorney, Agent, or Firm* — Knobbe, Martens, Olson & Bear, LLP

(57) ABSTRACT

Polypeptides are encoded by an adeno-associated virus (AAV)-derived endogenous viral element (mAAV-EVE1) found within the germline of numerous closely-related marsupial species. Nucleic acid molecules encode the polypeptides. Vectors can include the nucleic acid molecules, and recombinant AAV virions can include the polypeptides. A chimeric capsid protein can also include an MAAV-EVE1 polypeptide.

21 Claims, 7 Drawing Sheets
Specification includes a Sequence Listing.

FIGURE 5

```
SEQ_ID_NO:1   MSFLEKFEDWYEKSAATWRHLEAGPFHPKANQQHQDESHGLVLPGYKYLIPFNGLYKGEP
SEQ_ID_NO:30  MSFLEKFEDWYEKSAATWRHLEAGPFHPKANQQHQDESHGLVLPGYKYLIPFNGLDKGEP
              ***************************************************** ****

SEQ_ID_NO:1   VNQADKATLEQEKAYDQFLKEGENPYLTYNHTDQEFQEKLSEDTSFGGNLEKAVFQGKKR
SEQ_ID_NO:30  VNQADEAALEHDKAYDQLLKEGDNPYLTYNHADQEFQEKLSEDTSFGGNLEKAVFQGKKR
              *****:*:**:;*****;****;******:*;****************************

SEQ_ID_NO:1   LLKPLGVVEPDLEPVKGETFEKLRIFQQLQIFPFPSKRQKTRGLPFNPNSDNGAYTSSQQ
SEQ_ID_NO:30  LLEPLGLVEPDLAPVKGETFEKLRIFQQLQIFPFPSKRQKTRGLPFNPNSDNGAYTSSQQ
              **:***;***** ************************************************

SEQ_ID_NO:1   SAPTNLGSGIMAEGGGAPMENNQQGADGVGNSSGNWHCDSQWMGHRVATRKTHTWVLPTY
SEQ_ID_NO:30  SAPTNLGSGIMAEGGGAPMGDNQQGADGVGNSSGNWHCDSQWMGNRVVTRTTRTWVLPTY
              *******************:;************************:**:**:*:*******

SEQ_ID_NO:1   NNHLYKRVQNSVTTGSANNYFGFSTPWGYFDFNRFHCHFSPRDWQRLINNNWGLRPKNLH
SEQ_ID_NO:30  NNHLYKRIQNSVTTGSANNYFGFSTPWGYFDFNRFHCHFSPRDWQRLINNNWGLRPKSLR
              *******;************************************************:*;

SEQ_ID_NO:1   FKLFNIQVKEVTRRNVETTIANNLTSTIQVFADSEYQLPYVIRSAQEGCLPFFPDVFML
SEQ_ID_NO:30  FKLFNIQVKEVTTTNGETTIANNLTSTIQVFADSEYQLPYVIGSAQEGCLPFFPDVFML
              ************ * **************************:*******************

SEQ_ID_NO:1   PQYGYCTLDNDGKSLERSAFYCLEYFPSQMLREGNNFEFSYAFESVPFHSMWMHNQSLDR
SEQ_ID_NO:30  PQYGYCTLDNDGKSLERSAFYCLEYFPSQMLRTGNNFEFSYAFESVPFHSMWMHNQSLDR
              ********************************:****************************

SEQ_ID_NO:1   LMNPLIDQYLYRFDNLTSGNFVNPTFFYKKGSAGDMASQARNWLPGPMLFNQGLMDGPNN
SEQ_ID_NO:30  LMNPLIDQYLYRFDNLTSGNFVNPTFFYKKGSAGDMASQARNWLPGPMLFNQGLMDGPNN
              ************************************************************

SEQ_ID_NO:1   QANLDGWRISPPMVINGKSSIIPFGPSMYTAHNAADELEVQPSIRLPIFAKLASVPESTI
SEQ_ID_NO:30  QANLDGWRISPPMVINGKSSIIPFGPSMYTAHNAADELEVQPSIRLPIFAKLASVPESTI
              ************************************************************

SEQ_ID_NO:1   ISSIGNQDPNSKLIVTDENEVGTVNATAANTWGSMAVNQQFPTPTSAGQVLNQMSVMPGM
SEQ_ID_NO:30  ISSIGNQDPNSKLIVTDENEVGTVNATAANTWGSMAVNQQFPTPTSAGQVLNQMGVMPGM
              *****************************************************:*****

SEQ_ID_NO:1   VWQNFDIDLHGPIWAKIPHTDGYFRPSFLMGGFGLKRPPQIMIKNTPVPANPAFIFTPV
SEQ_ID_NO:30  VWQNFDIYLQGPIWAKIPHTDGHFRPSFLMGGFGLKRPPQIMIKNTPVPANPAFIFTPV
              *******:*;***********:***************************************

SEQ_ID_NO:1   KQNSFITQYSTGQVTVEIEWELQKETSKKWRPEIQFTSNFKNTIDLPFAPNNEGVYSEPR
SEQ_ID_NO:30  KQNSFITQYSTGQVTVEIEWELQKETSKKWRPEIQFTSNFKNTIDLPFAPNNEGVYSEPR
              ************************************************************

SEQ_ID_NO:1   PIGTRYLTRPI
SEQ_ID_NO:30  PIGTRYLTRPI
              ***********
```

*96.17% identity*

SEQUENCE LISTING

```
<160> NUMBER OF SEQ ID NOS: 41

<210> SEQ ID NO 1
<211> LENGTH: 731
<212> TYPE: PRT
<213> ORGANISM: Artificial Sequence
<220> FEATURE:
<223> OTHER INFORMATION: mAAV-EVE1 deduced capsid protein

<400> SEQUENCE: 1

Met Ser Phe Leu Glu Lys Phe Glu Asp Trp Tyr Glu Lys Ser Ala Ala
1               5                   10                  15

Thr Trp Arg His Leu Glu Ala Gly Pro Pro His Pro Lys Ala Asn Gln
            20                  25                  30

Gln His Gln Asp Asp Ser His Gly Leu Val Leu Pro Gly Tyr Lys Tyr
        35                  40                  45
```

-continued

```
Leu Ile Pro Phe Asn Gly Leu Tyr Lys Gly Glu Pro Val Asn Gln Ala
    50                  55                  60

Asp Lys Ala Thr Leu Glu Gln Glu Lys Ala Tyr Asp Gln Phe Leu Lys
 65                  70                  75                  80

Glu Gly Glu Asn Pro Tyr Leu Thr Tyr Asn His Thr Asp Gln Glu Phe
                 85                  90                  95

Gln Glu Lys Leu Ser Glu Asp Thr Ser Phe Gly Gly Asn Leu Gly Lys
            100                 105                 110

Ala Val Phe Gln Gly Lys Lys Arg Leu Leu Lys Pro Leu Gly Val Val
            115                 120                 125

Glu Pro Asp Leu Glu Pro Val Lys Gly Glu Thr Pro Glu Lys Leu Arg
130                 135                 140

Ile Pro Gln Gln Leu Gln Ile Pro Pro Pro Ser Lys Arg Gln Lys
145                 150                 155                 160

Thr Arg Gly Leu Pro Phe Asn Pro Asn Ser Asp Asn Gly Ala Tyr Thr
                165                 170                 175

Ser Ser Gln Gln Ser Ala Pro Thr Asn Leu Gly Ser Gly Ile Met Ala
            180                 185                 190

Glu Gly Gly Gly Ala Pro Met Gly Asn Asn Gln Gln Gly Ala Asp Gly
            195                 200                 205

Val Gly Asn Ser Ser Gly Asn Trp His Cys Asp Ser Gln Trp Met Gly
210                 215                 220

His Arg Val Ala Thr Arg Lys Thr His Thr Trp Val Leu Pro Thr Tyr
225                 230                 235                 240

Asn Asn His Leu Tyr Lys Arg Val Gln Asn Ser Val Thr Thr Gly Ser
                245                 250                 255

Ala Asn Asn Tyr Phe Gly Phe Ser Thr Pro Trp Gly Tyr Phe Asp Phe
            260                 265                 270

Asn Arg Phe His Cys His Phe Ser Pro Arg Asp Trp Gln Arg Leu Ile
            275                 280                 285

Asn Asn Asn Trp Gly Leu Arg Pro Lys Asn Leu His Phe Lys Leu Phe
290                 295                 300

Asn Ile Gln Val Lys Glu Val Thr Arg Arg Asn Val Glu Thr Thr Ile
305                 310                 315                 320

Ala Asn Asn Leu Thr Ser Thr Ile Gln Val Phe Ala Asp Ser Glu Tyr
                325                 330                 335

Gln Leu Pro Tyr Val Ile Arg Ser Ala Gln Glu Gly Cys Leu Leu Pro
            340                 345                 350

Phe Pro Pro Asp Val Phe Met Leu Pro Gln Tyr Gly Tyr Cys Thr Leu
            355                 360                 365

Asp Asn Asp Gly Lys Ser Leu Glu Arg Ser Ala Phe Tyr Cys Leu Glu
370                 375                 380

Tyr Phe Pro Ser Gln Met Leu Arg Thr Gly Asn Asn Phe Glu Phe Ser
385                 390                 395                 400

Tyr Ala Phe Glu Ser Val Pro Phe His Ser Met Trp Met His Asn Gln
                405                 410                 415

Ser Leu Asp Arg Leu Met Asn Pro Leu Ile Asp Gln Tyr Leu Tyr Arg
            420                 425                 430

Phe Asp Asn Leu Thr Ser Gly Asn Thr Val Asn Pro Thr Phe Thr Tyr
            435                 440                 445

Lys Lys Gly Ser Ala Gly Asp Met Ala Ser Gln Ala Arg Asn Trp Leu
450                 455                 460

Pro Gly Pro Met Leu Arg Asn Gln Gly Leu Met Asp Gly Pro Asn Asn
```

```
                465                 470                 475                 480
Gln Ala Asn Leu Asp Gly Trp Arg Ile Ser Pro Pro Met Val Ile Asn
                    485                 490                 495
Gly Lys Ser Ser Ile Ile Phe Pro Gly Pro Ser Met Tyr Thr Ala His
                    500                 505                 510
Asn Ala Ala Asp Glu Leu Glu Val Gln Pro Ser Ile Asn Leu Pro Ile
                    515                 520                 525
Phe Ala Lys Asp Ala Ser Val Pro Glu Ser Thr Ile Ile Ser Ser Ile
                    530                 535                 540
Gly Asn Gln Asp Pro Asn Ser Lys Leu Leu Val Thr Asp Glu Asn Glu
545                 550                 555                 560
Val Gly Thr Val Asn Ala Thr Ala Ala Asn Thr Trp Gly Ser Met Ala
                    565                 570                 575
Val Asn Gln Gln Thr Pro Thr Pro Thr Ser Ala Gly Val Leu Asn
                    580                 585                 590
Gln Met Ser Val Met Pro Gly Met Val Trp Gln Asn Arg Asp Ile Asp
                    595                 600                 605
Leu His Gly Pro Ile Trp Ala Lys Ile Pro His Thr Asp Gly Tyr Phe
                    610                 615                 620
His Pro Ser Pro Leu Met Gly Gly Phe Gly Leu Lys His Pro Pro Pro
625                 630                 635                 640
Gln Ile Met Ile Lys Asn Thr Pro Val Pro Ala Asn Pro Ala Thr Ile
                    645                 650                 655
Phe Thr Pro Val Lys Gln Asn Ser Phe Ile Thr Gln Tyr Ser Thr Gly
                    660                 665                 670
Gln Val Thr Val Glu Ile Glu Trp Glu Leu Gln Lys Glu Thr Ser Lys
                    675                 680                 685
Lys Trp Asn Pro Glu Ile Gln Phe Thr Ser Asn Phe Arg Asn Thr Ile
                    690                 695                 700
Asp Leu Pro Phe Ala Pro Asn Asn Glu Gly Val Tyr Ser Glu Pro Arg
705                 710                 715                 720
Pro Ile Gly Thr Arg Tyr Leu Thr Arg Pro Ile
                    725                 730

<210> SEQ ID NO 2
<211> LENGTH: 541
<212> TYPE: PRT
<213> ORGANISM: Artificial Sequence
<220> FEATURE:
<223> OTHER INFORMATION: mAAV-EVE1 deduced VP3 protein

<400> SEQUENCE: 2

Met Ala Glu Gly Gly Gly Ala Pro Met Gly Asn Asn Gln Gln Gly Ala
1               5                   10                  15
Asp Gly Val Gly Asn Ser Ser Gly Asn Trp His Cys Asp Ser Gln Trp
                20                  25                  30
Met Gly His Arg Val Ala Thr Arg Lys Thr His Thr Trp Val Leu Pro
                35                  40                  45
Thr Tyr Asn Asn His Leu Tyr Lys Arg Val Gln Asn Ser Val Thr Thr
                50                  55                  60
Gly Ser Ala Asn Asn Tyr Phe Gly Phe Ser Thr Pro Trp Gly Tyr Phe
65                  70                  75                  80
Asp Phe Asn Arg Phe His Cys His Phe Ser Pro Arg Asp Trp Gln Arg
                85                  90                  95
Leu Ile Asn Asn Asn Trp Gly Leu Arg Pro Lys Asn Leu His Phe Lys
```

```
                100                 105                 110
Leu Phe Asn Ile Gln Val Lys Glu Val Thr Arg Arg Asn Val Glu Thr
            115                 120                 125
Thr Ile Ala Asn Asn Leu Thr Ser Thr Ile Gln Val Phe Ala Asp Ser
            130                 135                 140
Glu Tyr Gln Leu Pro Tyr Val Ile Arg Ser Ala Gln Glu Gly Cys Leu
145                 150                 155                 160
Leu Pro Phe Pro Pro Asp Val Phe Met Leu Pro Gln Tyr Gly Tyr Cys
                165                 170                 175
Thr Leu Asp Asn Asp Gly Lys Ser Leu Glu Arg Ser Ala Phe Tyr Cys
            180                 185                 190
Leu Glu Tyr Phe Pro Ser Gln Met Leu Arg Thr Gly Asn Asn Phe Glu
            195                 200                 205
Phe Ser Tyr Ala Phe Glu Ser Val Pro Phe His Ser Met Trp Met His
            210                 215                 220
Asn Gln Ser Leu Asp Arg Leu Met Asn Pro Leu Ile Asp Gln Tyr Leu
225                 230                 235                 240
Tyr Arg Phe Asp Asn Leu Thr Ser Gly Asn Thr Val Asn Pro Thr Phe
                245                 250                 255
Thr Tyr Lys Lys Gly Ser Ala Gly Asp Met Ala Ser Gln Ala Arg Asn
            260                 265                 270
Trp Leu Pro Gly Pro Met Leu Arg Asn Gln Gly Leu Met Asp Gly Pro
            275                 280                 285
Asn Asn Gln Ala Asn Leu Asp Gly Trp Arg Ile Ser Pro Pro Met Val
            290                 295                 300
Ile Asn Gly Lys Ser Ser Ile Ile Phe Pro Gly Pro Ser Met Tyr Thr
305                 310                 315                 320
Ala His Asn Ala Ala Asp Glu Leu Glu Val Gln Pro Ser Ile Asn Leu
                325                 330                 335
Pro Ile Phe Ala Lys Asp Ala Ser Val Pro Glu Ser Thr Ile Ile Ser
            340                 345                 350
Ser Ile Gly Asn Gln Asp Pro Asn Ser Lys Leu Leu Val Thr Asp Glu
            355                 360                 365
Asn Glu Val Gly Thr Val Asn Ala Thr Ala Ala Asn Thr Trp Gly Ser
            370                 375                 380
Met Ala Val Asn Gln Gln Thr Pro Thr Pro Thr Ser Ala Gly Gln Val
385                 390                 395                 400
Leu Asn Gln Met Ser Val Met Pro Gly Met Val Trp Gln Asn Arg Asp
                405                 410                 415
Ile Asp Leu His Gly Pro Ile Trp Ala Lys Ile Pro His Thr Asp Gly
            420                 425                 430
Tyr Phe His Pro Ser Pro Leu Met Gly Gly Phe Gly Leu Lys His Pro
            435                 440                 445
Pro Pro Gln Ile Met Ile Lys Asn Thr Pro Val Pro Ala Asn Pro Ala
            450                 455                 460
Thr Ile Phe Thr Pro Val Lys Gln Asn Ser Phe Ile Thr Gln Tyr Ser
465                 470                 475                 480
Thr Gly Gln Val Thr Val Glu Ile Glu Trp Glu Leu Gln Lys Glu Thr
                485                 490                 495
Ser Lys Lys Trp Asn Pro Glu Ile Gln Phe Thr Ser Asn Phe Arg Asn
            500                 505                 510
Thr Ile Asp Leu Pro Phe Ala Pro Asn Asn Glu Gly Val Tyr Ser Glu
            515                 520                 525
```

```
                       Pro Arg Pro Ile Gly Thr Arg Tyr Leu Thr Arg Pro Ile
                           530                 535                 540

<210> SEQ ID NO 3
<211> LENGTH: 2196
<212> TYPE: DNA
<213> ORGANISM: Artificial Sequence
<220> FEATURE:
<223> OTHER INFORMATION: mAAV-EVE1 deduced cap gene

<400> SEQUENCE: 3
atgtcttttt tggagaaatt tgaggactgg tacgaaaagt cagctgctac ttggagacac     60
cttgaagctg gcccacctca tcctaaagct aatcaacaac atcaagatga ctctcatgga    120
ctggttctgc caggctataa gtatctcatt ccctttaatg gtctctataa gggggagcca    180
gttaatcaag cagacaaagc cacactggaa caagagaaag cctacgatca attcctcaaa    240
gaagggaaaa tccttacct cacctacaac cacacagacc aagagttcca ggaaaaactt    300
tcggaggaca cttcgtttgg tggtaacctt ggcaaggcag tgtttcaagg aaagaaacga    360
ctgcttaagc cattaggagt agtagaacca gacctggagc ctgtgaaagg agaaactcct    420
gagaagctgc gcatccctca gcaactccaa atccctcctc ctccatctaa cgacaaaaag    480
acgagaggac tccctttcaa cccaaacagc gacaatggag catacaccag cagtcagcaa    540
tcagccccca ctaatttggg atctggtatc atggcagaag aggtggcgc accaatgggc    600 aataatcaac agggtgctga tggagtaggt aattcctcag gaaattggca ttgtgattcc    660
caatggatgg gccacagagt cgccacccga aaaactcaca cctgggtctt gcccacctac    720
aacaaccacc tctacaagcg agttcaaaac agtgtcacca caggcagtgc caacaactac    780
tttggcttca gcacccctg ggggtatttt gacttcaaca gattccactg ccacttcagc    840
ccccgagact ggcaaagact tatcaataac aactggggac tgcgacctaa aaacctgcac    900
ttcaaactct tcaacatcca agtcaaggag gtcacaagga ggaatgttga ccacaatt    960 gctaataacc ttaccagcac gattcaagtc tttgcggact cagagtatca actcccatac   1020
gtgatcagga gtgctcaaga ggggtgtcta ctccccttcc ctcctgatgt gttttatttg   1080
cctcagtatg ggtattgtac tttggacaat gatgggaaaa gtttagagag gagtgcattc   1140
tactgtctag aatatttcc tagccaaatg ttgagaacgg gtaacaactt tgaattttcc   1200
tatgcttttg aatctgtccc ctttcatagc atgtggatgc ataatcagag cttggataga   1260
ttgatgaatc cattgattga tcaatatctg tatagatttg ataatctaac cagtggaaac   1320
actgttaatc ccaccttcac ttacaaaaag ggatcagcag gtgatatggc ttctcaggct   1380
aggaattggt tacctggtcc tatgcttagg aatcagggac taatggatgg tcctaacaat   1440
caggccaatc tagatggttg gaggatcagt cctccaatgg tgatcaatgg aaaatcttct   1500
attatatttc ctgggccatc catgtatacc gcacacaatg ctgcagatga actggaggtt   1560
caacctagca ttaatctccc tatctttgct aaagatgcct ctgtacctga atccaccata   1620
attagtagta ttggtaatca agatcctaat agtaaattgt tagtcactga tgagaacgag   1680
gtcgggacag tgaatgctac tgctgctaat acctggggggt ctatggcagt caaccagcag   1740
actcccaccc ccactagtgc aggacaggtt ctaaatcaaa tgagtgtcat gcctggaatg   1800
gtctggcaga atagagacat cgatctccca ggtcccattt gggctaagat tcctcacaca   1860
gatggttact ccatccctc tcctctcatg ggtggctttg gtctcaaaca tcctcctcct   1920
cagattatga ttaaaaacac tcctgtccct gctaaccctg ccaccatctt cactcctgtc   1980
```

| aaacaaaatt ctttcatcac tcaatactct actggtcaag tgactgtaga aattgaatgg | 2040 |
| gaactccaga aggaaacctc caagaaatgg aatcctgaaa tccagtttac ttccaatttc | 2100 |
| agaaacacta ttgacttacc ttttgctccc aacaatgaag gtgtatactc tgaacctcgt | 2160 |
| cccattggta cccgatacct tacccgtccc atctaa | 2196 |

```
<210> SEQ ID NO 4
<211> LENGTH: 1626
<212> TYPE: DNA
<213> ORGANISM: Artificial Sequence
<220> FEATURE:
<223> OTHER INFORMATION: mAAV-EVE1 deduced VP3 coding sequence

<400> SEQUENCE: 4
```

| atggcagaag gaggtggcgc accaatgggc aataatcaac agggtgctga tggagtaggt | 60 |
| aattcctcag gaaattggca ttgtgattcc caatggatgg ccacagagt cgccacccga | 120 |
| aaaactcaca cctgggtctt gcccacctac aacaaccacc tctacaagcg agttcaaaac | 180 |
| agtgtcacca caggcagtgc caacaactac tttggcttca gcaccccctg ggggtatttt | 240 |
| gacttcaaca gattccactg ccacttcagc ccccgagact ggcaaagact tatcaataac | 300 |
| aactggggac tgcgacctaa aaacctgcac ttcaaactct tcaacatcca agtcaaggag | 360 |
| gtcacaagga gaatgttga gaccacaatt gctaataacc ttaccagcac gattcaagtc | 420 |
| tttgcggact cagagtatca actcccatac gtgatcagga gtgctcaaga ggggtgtcta | 480 |
| ctcccctcc ctcctgatgt gtttatgttg cctcagtatg gtattgtac tttggacaat | 540 |
| gatgggaaaa gtttagagag gagtgcattc tactgtctag aatattttcc tagccaaatg | 600 |
| ttgagaacgg gtaacaactt tgaatttttc tatgcttttg aatctgtccc ctttcatagc | 660 |
| atgtggatgc ataatcagag cttggataga ttgatgaatc cattgattga tcaatatctg | 720 |
| tatagatttg ataatctaac cagtggaaac actgttaatc ccaccttcac ttacaaaaag | 780 |
| ggatcagcag gtgatatggc ttctcaggct aggaattggt tacctggtcc tatgcttagg | 840 |
| aatcagggac taatggatgg tcctaacaat caggccaatc tagatggttg gaggatcagt | 900 |
| cctccaatgg tgatcaatgg aaaatcttct attatatttc ctgggccatc catgtatacc | 960 |
| gcacacaatg ctgcagatga actggaggtt caacctagca ttaatctccc tatctttgct | 1020 |
| aaagatgcct ctgtacctga atccaccata attagtagta ttggtaatca agatcctaat | 1080 |
| agtaaattgt tagtcactga tgagaacgag gtcgggacag tgaatgctac tgctgctaat | 1140 |
| acctgggggt ctatggcagt caaccagcag actcccaccc ccactagtgc aggacaggtt | 1200 |
| ctaaatcaaa tgagtgtcat gcctggaatg gtctggcaga atagagacat cgatctccat | 1260 |
| ggtcccattt gggctaagat tcctcacaca gatggttact tccatccctc tcctctcatg | 1320 |
| ggtggctttg gtctcaaaca tcctcctcct cagattatga ttaaaaacac tcctgtccct | 1380 |
| gctaaccctg ccaccatctt cactcctgtc aaacaaaatt ctttcatcac tcaatactct | 1440 |
| actggtcaag tgactgtaga aattgaatgg gaactccaga aggaaacctc caagaaatgg | 1500 |
| aatcctgaaa tccagtttac ttccaatttc agaaacacta ttgacttacc ttttgctccc | 1560 |
| aacaatgaag gtgtatactc tgaacctcgt cccattggta cccgatacct tacccgtccc | 1620 |
| atctaa | 1626 |

```
<210> SEQ ID NO 5
<211> LENGTH: 4343
<212> TYPE: DNA
```

<213> ORGANISM: Macropus rufogriseus

<400> SEQUENCE: 5

```
agagccagcg atcaaagaag tggccacact ctccttaaga tttgaaaagc ccaccaaagc      60
agatgacgta attacccata atgcaattgg aatcagtccc agactgcatt gcaagaggct     120
ataaaaagaa ggatgtgtgc ctagaaattc attaatcatc tactgactga gcgagtgtgc     180
atcaaaagaa gaagaataaa tagaagagat gaagacatgc tggagctaga acacgtgaag     240
ttttatgagg caattttcct tgtgcccaga gacttggagt ctgacatccc tggctatcct     300
aagagactgg tcactcagac agaagagacc aagtggacgc tttcagaaaa ggacaacctg     360
gacttggaag ctttggagag tcgacaagta acatttgccc atctattctc ctgcaaattc     420
cttaagcact gggagtacct gacaagaaat cgagaattca atactatgt ccagctgaaa      480
aagggtgaga tctattacca tttacatatg cttttttgaga ccagtggaat tcagtgcatg     540
gtgctcagcc gttacatcag tcagatcaag acctcgctgc gagctaaagt ctctaacaat     600
gctgaggtta atatcgaaaa ctgaaaactg actggccatt atgacgacta aggccactgg     660
tgggggtcaa acaaacaggt ggactataat tgcatcaact ggtatttaat agcataaaaa     720
caaccagaat ttcagtgggg gtggacaaat attgaggaat ataaggactt gatcctcaat     780
atccctgcca gaccgcagct cgtaggctag ttcttcacat agacctactt cgctcctggg     840
gtgagtgact cccaatcctc ttaaatctct aatacttctg gtgctcttct attgttatgg     900
aaatactgag agatacatgg agcttgtaaa ttggcttgtg gagcagcacc tctgaaaagc     960
agtggattat tgaaaatcag gaaagttatc tctgtcacca atccactagc aatggagcca    1020
ggaagattaa agtcgctctg gacaatactt ctaaaattat gaatctgacc aaaaatgcag    1080
atgattacct tatccctaaa gaatttgtca gttttgacaa cattaaacag aaccatatct    1140
attggatctt taagaatgga tacggatcta tcctggtagg ctgggccaga aaagaatttg    1200
gcaaagaaa caccatctgg gtctatggaa aggccactac tgagaactaa cattgtggaa    1260
gccgttgcac acacggtgcc cttctacggg tatgtgaatt ggactaatga aactttcca    1320
ttcaatgatt gtgtggataa aatgctcatc tggtgggagg aaggcaagat tacctctatg    1380
gtggttgaga cagctaaagc catcctcaga ggagctaaag ttcaggtgga ccaggaatgt    1440
aagtcctctg ttcaaattga ttgtactcca gtcatcatca cctccaacac cgacatgtgc    1500
tacgtggtgg atcggaacac tatgatcttt gagcataagc agttgttaca agaccacatg    1560
tttcaattca tgctcatgga gagacttcct gatgactttg gcaaggtgac aaaggaggag    1620
gtgcatcagt tctttttaaat gggcagcttt taatcaaatt cccccccgagc aggaattcac    1680
tgtcaagaag attatgtcat ccattgactg ttattatgac cacaagcaga aatgggagga    1740
gtatccctcg actttctatc aaggggggcta taaaaagggc gagcctccct caaaaaagtt    1800
ctttccattt caggatttga agaaaattga ggtcattaag cagagagccc ccacagtgga    1860
attgaacttt gagaatctca aaaggtttgg tctcaatgta attcctgctt ctgatcctat    1920
tgctttggat gactgtcagg atgaggaata aaatccctag atgtcttttt tggagaaatt    1980
tgaggactgg tacaaaaagt cagctgctat ttggagacac cttgaagatg gcccacctca    2040
tcctaaagct aatcaacaac atcaagatga ctctcatgga ctggtttttt caggctataa    2100
gtatcttatt cccctttaatg gtctccataa gggagagcta gttaatcaag cagacaaagc    2160
cacacttgaa caagagaaag cctatgatca attcctcaaa gaaatccttt cctcgcctac    2220
aaccacacag accaagagtt ccaggaaaaa cttttcggagg gcacttcgtt tggtggtaac    2280
```

```
cttggcaagg cagtgtttca aggaaagaaa tgactgctta agccattagg agtagtagaa    2340
ccagacctgg agcctgtgaa aggagaaact cctgagaagc tgtgcatccc tcagcaactc    2400
caaatccctc ctctttcttt taaacgacaa aagacaagag gactcccttt caacccaaac    2460
agtgacaatg gaccatacaa cagcattcag caatcagccc ccactaattt gggatctggt    2520
atcatggcag aaggaggtgg agtaccaatg ggcaataatc aacagggtgc tgatagagta    2580
ggaaattctt cgggaaatta gcattgtgat tctcaataga tgggccacag aatcaccacc    2640
cgaaaagctc tctggatcta gcctacctgc aacaaccacc tctacaagca gttcaaaata    2700
gtgtcaccac aggcagtgcc aacaacttca gctttggctt cagtaccctc tgggggaatt    2760
ttgacttcaa cagattccac tgccacttca gcccccgaga ctggcaaaga cttatcaata    2820
acaactgggg actgtgacct aaaaacctgc acttcaaact ctttaacatt caagtcaagg    2880
aggtcacaag gaggaatgtt gaaccacaa ttgctaataa ccttaccagc atgattcaag     2940
tctttgcgga ctcagagtgt caactcccat acgtgatgag gagtgctcaa gagaggtgcc    3000
tactcccctt ccctcctgat gtgtttgtgt tgcctcagta tggatattgt actttggaca    3060
atgatgggaa aagtttagag aggagcgcat tctactttct agaatatttt cctcatcacc    3120
aaatattgag aatgggtaac aactttgcat tttcctatgc ttttgaatct gtcccctttc    3180
atagcatgtg gatacataat cagagcttgg atagattgat gaatccattg attgatcaat    3240
atctgtacag atttgataat ccaacctgtg aaaacactgt taatcctacc ttcacttaca    3300
aaaagggatc agcaggtgat atggcttctc aggctaggaa ctggttgcct ggtcctatgc    3360
ttaggaatca gggactaaag gatggtccta acaatcaggc caatttagat ggttggagga    3420
tcagtcttcc aatggtgatc aatggaaaat cttctattat atttcctggg ccatccatgt    3480
ataccgcaca caatgctgca gatgaactgg aggttcaacc tagcattaat ctccccatct    3540
ttgctaaaga tgcctctgta ccggaatcca ccataattag tagtattggt aatcagaatc    3600
ctaatagtaa attgtcagtc actgatgaga acgaggtcgg gacagtgaat gctactgctg    3660
ccaatacttg ggggtctatg gcagtcaacc agcagactcc caccccgact agtgcaggac    3720
aggttctaaa tcaaatgagt gtcatgcctg gaatggtctg gcagaataga gacatcaatc    3780
tccatggtcc catttaggct aagattcctc acacagatgg ttacttccat ccctctcctc    3840
ttatgggtgg ctttggtctc aaacatcctt ttcctcagaa tatgattaaa aactctcctg    3900
tccctgctaa ccccaccacc atcttcactc ctgccaaaca acactctttc atcactcaat    3960
actctattgg tcaagtgact gtagaaattg aatgggaact ccataaggaa agttccaaga    4020
aatggactcc tgaaatccag tttacttcca atttcagaaa cactattgac ttaccttttg    4080
ctcccaacaa tgaaggtgta tactatgaac cttgtcccat tggtacctga taccttaccc    4140
ttcccatcta actgtattgt acatatttca tatttgtatt tttttattca ataaactgat    4200
gtattcattt cattgtattt ctcttatcac ttggctctta taagcagatg atgagctgcc    4260
atgggttggc tttcatggga ggcgtggtct cattaaaatc ttatggagaa tgtggtcact    4320
cctttgctcc ttctgcttgc tca                                            4343
```

<210> SEQ ID NO 6
<211> LENGTH: 4320
<212> TYPE: DNA
<213> ORGANISM: Macropus rufus

<400> SEQUENCE: 6

```
agagccagcg atcaaagaag tggccacact ctccttaaga tttgaaaagc ccaccaaagc      60
agatgatgta attacccatg atgcaattgg aatcagtccc agactgcatt gcaagaggct     120
ataaaatgaa ggatgtgtgc ctagaaattc attaatcatc taccgaccga gtgagtgtgc     180
atcaaaagaa gaagaataaa tagtagagat gaagacatgc tggagctgga acacgtgaag     240
ttttatgagg caattttcct tgtgcccaga gatttggagt ctgacatccc tggctatcct     300
aagagactgg tcactcagat agaagagacc aagtggatgc tttcagaaaa ggacaacctg     360
gacttggaag cttttggagag tcgacaggta acatttgccc atctattctc ccgcaaattc     420
cttaagcact gggagtacct gagaagaaat cgagaattca aatactatgt ccagctgaaa     480
aagggtgaga tctattatca tttacatatg cttttttgaga ccagtggaat tcagtccatg     540
gtgctcagcc attacatcag ccagatcaag acctcgctgc gagctaaagt ctctaacaat     600
gctgaggtta atatcgaaaa ctgaaaactg actggccatt acgacggcta aggccaccgg     660
tgggggtcaa ccaaacaggt ggactataat tgcatcaact ggtatttaat agcataaaaa     720
caaccagaat ttcagtgggg gtggacaaat attgaggaat ataaggactt gatcctcaat     780
atccccgcca gaccgcagct cataggctag ttcttcacat agacctactt cgctcctggg     840
gtgagtgact cccaatcctc ttaaatctct aatacttctg gtgctttcta ttgttataga     900
aatactgaga gatacatgga gcttgtaaat tggcttgtgg agcagcaccct ctgaaaagca     960 gtgcattatt gaaaatcagg aaagttatct ccgtcaccaa tccactagca atggagccag    1020
gaagattaaa gtcactctgg acaatgcttc taaaattatg aatctgacca aaaatgcaga    1080
tgattacctt atcccgaaag aatttgtcag ttttgacacc attaaacaga gccatatcta    1140
ttggatcttt aagaatggat atgatctatc ctggtgggct gggccggaaa agaatgtggc    1200
aaaagaaaca ccatctgggt ctatggaaag gccactactg gaacactaa cattgtggaa    1260 gccattgcac acccggtgcc cttctacggg tatgtgaatt ggactaatga aactttcca    1320 ttcaatgatt gtgtggataa aatgctcatc tggtgggagg aaggcaagat tacctctatg    1380
gtggtttaga cagctaaagc catccttgga ggagctaaag ttcaggtgga ccaggaatgt    1440
aagtcctctg ttcaaattga ttgtactcca gtcatcatca cctccagcac cgacatgtgc    1500
tacgtggtgg atcagaacac tatgatcttt gagcacaagc agttgttgca agaccacatg    1560
tttcaattca tgctcatgga gagacttcct gatgactttg gcaaggtgac aaaggaggag    1620
gtgcatcagt tcttttaaat gggcagctgt taatcaaatt cccctgagc aggaattcac    1680 tgtcaagaag attatgtcat ccattgactg ttattatgac cacaagcaga atgggagga    1740 gtatccctcg actttctatc aaggggggcta taaaaaggcc gagcctccct tgaaaaagtt    1800 cttttccattt tgggatttga agaaaattga ggtcatcgag cagaaagccc ccacagtgga    1860
attgaacttt gagaatctca aaaggtttgg tctcaatgta attcctgctt ctgatcctat    1920
tgctttggat gactgtcagg atgaggaata aatccctaga tgtctttttt ggagaaattt    1980
gaggactggt acaaaaagtc agctgctatt tggagacacc ttgaagctgg cccacctcat    2040
cctaaagcta atcaacaaca tcaagatgac tctcatggac tggttctgcc aggctataag    2100
tatcttattc cctttaatgg tctctataag ggggagccag ttaatcaagc agacaaagcc    2160
acactcgaac aaccgaaagc ctatgatcaa ttcctcaaag aaggggaaaa tccttttctc    2220
acctacaacc acacagacca agagttccag gaaaaacttt cggagggcac tttgtttggt    2280
ggtaaccttg gcaaggcagt gtttcaagga aagaaatgac tgcttaagcc attaggagta    2340
gtagaaccag acctggagcc tgtgaaagga gaaactcctg agaagctgtg catccctcag    2400
```

```
caactccaaa tccctcctcc ttcttctaaa cgacaaaaga caagaggact ccctttcaac    2460
ccaaacagtg acaatggacc atacaacagc attccgcaat cagcccccac taatttggga    2520
tctggtatca tggcagaagg aggtggagta ccaatgggca ataatcaaca gggtgctgat    2580
agagggaaat tagcattgtg attctcaatg gatgggccac agagtcacca cccgaaaagc    2640
tctctgggtc ttgcctacct gcaacaacca cctctacaag cagttcaaaa tagtgtcacc    2700
acaggcagtg ccaacaacta ctttggcttc agcactccct gggggaattt tgacttcaac    2760
agattccact gccacttcag ccccctagac tggcaaagac ttatcaataa caactgggga    2820
ctgcgaccta aaaacctgca cttcaaactc ttcaacatcc aagtcaagga ggtcacaagg    2880
aggaatgttg aaaccacaat tgctaataac cttactagca tgattcaagt ctttgcggac    2940
tcagagtgtc aactcccata cgtgatcagg agtgctcaag agaggtgcct actcccttc     3000 cctcctgatg tgtttatgtt gcctcagtat ggatattgta ctttggacag tgatgggaaa    3060
agtttagaga gagcgcatt ctactttcta gaatattttc ctaaccaaat attgagaatg      3120
ggtaacaact ttgcattttc ctatgctttt gaatctgtcc tcttttatag catgtggata    3180
cataatcaga cctcggatgg attgatgaat ccattgattg atcaatatct gtatagattt    3240
gataatccaa cctgtggaaa cactgttaat cccaccttca cttacaaaaa gggatcagca    3300
ggtgatatgg cttctcaggc taggaactgg ttgcctggtc ctatgcttag gaatcaggga    3360
ctaaaggatg gtcctaacaa tcaggccaat ttagatggtt ggaggatcag tcctccaatg    3420
gtgatcaatg gaaaatcttc tattatattt cctgggccat ccatgtatac cgcatacaat    3480
gctgcagatg aactggaggt tcaacctagc attaatctcc ccatctttgc taaagatgcc    3540
tctgtacctg aatccaccat aattagtagt attggtaatc aagatcctaa tagtaaattg    3600
ttagtcacta atgagaacaa ggtcgggaaa gtgaatgcta ctgctgctaa tacctggggg    3660
tctatggcag tcaaccagca gtctcccacc cccactagtg cactaaatca atgagtgtc     3720 atgcctggaa tggtctggca gaatagaaac atcaatctcc atggtccat ttgggctaag      3780 attcctcaca cagatggtta cttccatccc tcctctctta tgggtggctt tggtctcaaa    3840
catcctcctc ctcagaatat gattaaaaac ctcctgtcc ctgctaaccc caccaccatc      3900
ttcactcctg tcaaacaaaa ctcttttcatc actcaatact ctattggtca agtgactgta    3960
gaaattgaat gggaactcca taaggaaagt tccaagaaat ggactcctaa aatccagttt    4020
acttccaatt tcagaaacac tattgactta ccttttgctc ccaacaatga aggtgtatac    4080
tatgaacctc gtcccattgg tacctgatac cttacccttc ccatcgaact gtattgcaca    4140
tatttcatat ttgtatttt ttattcaata aactgatgta ttcatttcat tgtatttctc      4200
ttatcacttg tctcttataa gcagacgatg agctgccgtg aattggcttt cacaggaggc    4260
gtggtctcat taaaatctta tggagaatgt ggtcactcct ttgctccttc tgcttgctca    4320
```

<210> SEQ ID NO 7
<211> LENGTH: 4346
<212> TYPE: DNA
<213> ORGANISM: Macropus parma

<400> SEQUENCE: 7

```
agagccagag atcaaagaag tggccacact ctccttaaga tttgaaaagc ccaccaaagc       60
agatgatgta attacccata atgcaattgg aatcagtccc agactgcatt gcaagaggct     120
ataaaaagaa ggatgtgtgc ctagaaattc attaatcatc taccgactga gcgagtgtgc     180
```

```
atcaaaagaa gaagaataaa tagaagagat gaagacatgc aggagctgga acacgtgaag      240
ttttatgggg caattttcct tgtgtccaga gacttggagt ctgacatccc tggctatcct      300
aagagactgg tcactcagat agaagagacc aagtggacgc tttcagaaaa ggacaacctg      360
gacttggaag ctttggagag tcgacaggta acatttgccc atctattctc ccgcaaattc      420
cttaagcact gggagtacct gacaagaaat cgagaattca aatactatgt ccagcttaaa      480
aagggtgaga tctattacca tttacatatg cttttgtgaga ccagtggaat tcagtccatg      540
gtgctcagcc gttacaccag ccagatcaag acctcgctgt gagctaaagt ctctaacaat      600
gctgaggtta atatcaaaaa ctgaaaactg actggccatt acaacgacta aggccaccgg      660
gggggtcaac caaacaggtg gactataatt gcatcaactg gtatttaata gcataaaaac      720
aaccagaatt tcagtggggg tggacaaata ttgaggaata taaggacttg atcctcaata      780
tccccgccag accacagctc ataggctagt tcttcacata gaccaacttt gctcctgggg      840
tgaatgactc ccaatcctct taaatctcta atacttctgg tgctcttcta ttgttataga      900
aatactgaga gatacatgga gcttgtaaat tggcttgtgg agcagcacct ctgaaaagca      960
gtggattatt gaaaatcagg aaagttatct ctgtcaccaa tccactagca atggagccag     1020
gaagattaaa gtcgctctgg acaatgcttc taaaactatg aatctgagca aaaatgcaaa     1080
tgattacctt atcccaaaag aatttgtcag ttttgataac attaaacaga accatatcta     1140
ttggatcttt aagaatggat acggatctat cctggtgggc tgggccagaa aagaatttgg     1200
caaaagaaac accatctggg tctacggaaa ggccactact gggaacacta acattgtgga     1260
agccattgca cacatggtgc ccttctatgg gtatgtgaat tggactaatg agaactttcc     1320
attcaatgat tgtgtggata aaatgctcat ctggtgggag gaaggcaaga ttacctctat     1380
ggtggttgag acagctaaag ccatcctcag aggagctaaa gttcaggtgg accaggaatg     1440
taagtcctct gttcaaattg attgtactcc agtcatcatt acctccagca ccaacatgtg     1500
ctacgaggtg gatcagagca ctatgatctt tgagcacaag cagttgttac aagaccacat     1560
gtttcaattc atgcttgtgg agagacttcc tgatgacttt ggcaaggtga caaaggagga     1620
ggtgcgtcag ttcttttaaa tgggcagctg ttaatcaaat tcccctgag caggaattca     1680 ctgtcaagaa gattatgtca tccattgact gttattatga ccacaagcag aaatgggagg     1740
agtatccctc gactttctat caagggggct ataaaaaggg tgagcctccc tcgaaaaagt     1800
tctttccatt tctggatttg aagaaaattg aggtcatcaa gcagagagcc cccacggtgg     1860
aattgaactt tgggaatctc aaaaggtttg gtctcaatgt aattcctgct tctgatccta     1920
ttgctttgga tgactgtcag gatgaggaat aaatccctag atgtctttt tggagaaatt     1980 tgaggactgg tacaaaaagt cagctgctat ttggagacac cttgaagct ggcccacctc     2040 atcctaaagc taatcaacaa catcaagatg actttcatgg actggttctg ccaggctata     2100
agtattttat tcgctttaat ggtctctata aggggagcc agttaatcaa gcagacaaag     2160
ccacactcga acaagagaaa gcctatgatc aattcctcaa agaagggaa atcctttcc      2220 tcacctacaa ccacaaagac caagagttcc aggaaaaact ttcggagggc acttcgtttg     2280
gtggtaacct tggcaaggca gtgtttcaag gaaagaaatg actgcttaag ccattaggag     2340
tagtagaacc agacctgcag cctgtgaaag gagaaactcc tgagaagctg tgcatccctc     2400
agcaactcca aatccctcct ccttcttcta aacgacaaaa gacaagagga ctcccttca     2460 acccaaacag tgaaaatgga ccatacaaga gcattcagca atcagccccc actaatttgg     2520
gatctggtat catggcagaa ggaggtggag taccaatggg caataatcaa cagggtgctg     2580
```

| | |
|---|---|
| atagagtagg taattctttg ggaaattagc attgtgattc tcaatggatg ggccacagag | 2640 |
| tcaccacccg aaaagctctc tgggtcttgc ctacctgcaa caaccacctc tacaaacagt | 2700 |
| tcaaaatagt gtcaccacag gcagtgccaa caactacttt ggcttcagca ccccctgggg | 2760 |
| gaattttgac ttcaacagat tccactgcca cttcagcccc ctggactggc aaagacttat | 2820 |
| caataacaac tggggactgc gacctaaaaa cctgcacttc aaactcttca acatccaagt | 2880 |
| caaggaggtc acaaggagga atgttgaaac tacaattgct aataacctta ccagcatgat | 2940 |
| tcaagtcttt gcggactcag agtgtcaact cccatacgtg atcaggagtg ctcaagagaa | 3000 |
| gtgcctactc cctttccctc ctgatgtgtt tatattgcct cagtatggat attgtacttt | 3060 |
| ggacagtgat ggggaaagtt tagagaggag tgcattctac tttctagaat attttcctaa | 3120 |
| ccaaatattg agaacgggta acaactttgc attttcctat gcttttgaat ctgtccccett | 3180 |
| ttatagcatg tggatacata atcagaccett ggatagactg atgaatccat tgattgatca | 3240 |
| atatctgtat agatttgata atccaacctg tggaaacact gttaatccca ccttcacttt | 3300 |
| caaaaaggga tcagtaggtg atatggcttc tcaggttagg aactggttgc ctggtcctat | 3360 |
| gcttaggaat cagggactaa aggatggtcc taacaatcag gccaatttag atggttggag | 3420 |
| gatcagtcct ccaatggtga tcaatggaaa atcttctatt atatttcctg gccatccat | 3480 |
| gtataccgca tacaatgctg cagatgaact ggcggttcaa cctagcatta atctccccat | 3540 |
| ctttgctaaa gatgcctctg tacctgaatc caccataatt agtagtattg gtaatcaaga | 3600 |
| tcctcatagt aaattgttag tcactgatga agaacgaggt cgggaaagta aatgctactg | 3660 |
| ctgctaatac ctgggggtct atagcagtca accagcagac tcccaccccc actagtgcag | 3720 |
| gacaggttct aaatcaaatg agtgtcatgc ctggaatggt ctggcagaac agagacatca | 3780 |
| atctccatgg tcccatttgg gctaagattc ctcacacaga tggttacttc catccctctc | 3840 |
| ctcttatgga tggctttggt ctcaaacatc ctcctcctca gaatatgatt aaaaactctc | 3900 |
| ctgtccctgc taacccacc accatcttca ctcctgtcaa acaaaactct ttcattactc | 3960 |
| aatactctat tggtcaagtg actgtagaaa ttgaatggaa actccataag gaaagttcca | 4020 |
| agaaatggac tcctaaaatc cagtttactt ccaatttcag aaacactatt gacttacctt | 4080 |
| ttgctcccaa caatgaaggt gtatactatg aacctcgtcc cattggtacc tgataccttta | 4140 |
| ccccttcccat ctaactgtat tgcacatatt tcatatttgt attttttttat tcaataaact | 4200 |
| gatatattca tttcattgta tttctcttat cacttggctc ttataagcag aggatgagct | 4260 |
| gccatgtgtt ggctttcaca ggaggtgtgg tctcattaaa atcttatgga gaatgtggtc | 4320 |
| actcctttgc tccttctgct tgctca | 4346 |

<210> SEQ ID NO 8
<211> LENGTH: 4321
<212> TYPE: DNA
<213> ORGANISM: Macropus robustus

<400> SEQUENCE: 8

| | |
|---|---|
| agagccagcg atcaaagaag tggccacact ctccttaaga tgtgaaaagc ccaccaaagc | 60 |
| agatgatgta attaccccatg atgcaattgg aatcagtccc agactgcatt gcaagaggct | 120 |
| ataaaatgaa ggatgtgtgc ctagaaattc attaatcatc taccgactga gtgagtgtgc | 180 |
| atcaaaagaa gaagaataaa tagtagagat gaagacatgc tggagctggt acacgtgaag | 240 |
| ttttatgagg caatttttcct tgtgcccaga gatttggagt ctgacatccc tggctatcct | 300 |

```
aagagactgg tcactcagat agaagagacc aagtggacgc tttcagaaaa ggacaacctg    360
gacttggaag ctttggagag tcgacaggta acatttgccc gtctattctc ccgcaaattc    420
cttaagcact gggagtacct gagaagaaat cgagaattca aatactatgt ccagctgaaa    480
aagggtgaga tctattatca tttacatatg cttttttgaga ccagtggaat tcagtccatg   540
gtgctcagcc gttacatcag ccagatcaag acctcgctgc gagctaaagt ctctaacaat    600
gctgaggtta atatcgaaaa ctgaaaactg actggccatt acgacgacta aggccaccgg    660
gggtgggtca accaaacagg tggactataa ttgcatcagc tggtatttaa tagcataaaa    720
acaaccagaa tttcgtgggg gtggacaaat attgaggaat ataaggactt gatcctcaat    780
atccccgcca gaccacagct cataggctag ttcttcacat agacctactt cgctcctggg    840
gtgagtgact cccaatcctc ttaaatctct aatacttctg gtgctttcta ttgttataga    900
aatactgaga gatacatgga gcttgtaaat tggcttgtgg agcagcacct ctgaaaagca    960
atgcattatt gaaaatcagg aaagttatcc ccgtcaccaa tccactagca atggagccag   1020
gaagattaaa gttgctctgg acaatgcttc taaaattatg gatctgaccg aaaatgcaga   1080
ttgattacct tatcccgaaa gaatttgtca gtttgacacc attaaacaga gccatatcta   1140
ttggatcttt aagaatggat agggatctat cctggtgggc tgggcccaga aaagaatttg   1200
gcaaaagaaa caccatctgg gtctatggaa aggccactac tgggaacact aacattgtgg   1260
aagccgttgc cacccggtg cccttctacg ggtatgtgaa ttggactaat gagaactttc    1320
cattcaatga ttgtgtggat aaaatgctca tctggtggga ggaaggcaag attacctcta   1380
tggtggttga gacagctaaa gccatccttg gaggagctaa agttcaggtg gaccaggaat   1440
gtaagtcctc tgttcaaatt gattgtgctc cagtcatcat cacctccagc accgacatgt   1500
gctacgtggt ggatcagaac actatgatct ttgagcacaa gcagttgtta caagaccaca   1560
tgtttcaatt catgcttgtg gagagacttc ctgatgactt tggcaaggtg acaaaggagg   1620
aggtgcatca gttcttttaa atgggcagct gttaatcaaa ttcccccctga gcaggaattc   1680 actgtcaaga agattatgtc atccattgac tgttattatg accacaagca gaaatgggag   1740
gagtatccct cgactttcta tcaagggggc tataaaaagg ccgagcctcc ctcgaaaaag   1800 ttcttttccat ttcaggattt gaagaaaatt gaagtcatcg agcagagagc ccccacagtg   1860
gaattgaact ttgagaatct caaaaggttt ggtctcaatg taattcctgc ttctgatcct   1920
atcgctttgg atgactgtca ggatgaggaa taaatcccta gatgtctttt ttggagaaat   1980
ttgaggactg atacaaaaag tcagctgcta tttggagaca cttgaagctg cccaccctca   2040
tcctaaagct aatcaacaac atcaagatga ctctcatgga ctggttctgc caggctataa   2100
gtatcttatt cccttttaatg gtctctataa ggggagcca gttaatcaag cagacaaagc   2160
cacactcgaa caagagaaag cctatgatca attactcaag gaagggaaa atcctttcct    2220 cacctacaac cacacagacc aagagttcca ggaaaaattt tcggagggca cttcgtttgg   2280
tggtaacctt ggcaaggcag tgtttcaagg aaagaaatga ctgcttaagc cattaggagt   2340
agtagaacca gacctggagc ctgtgaaagg agaaactcct gagaagctgt gcatccctca   2400
gcaactccaa atccctcctc cttcttctaa acgacaaaag acaagaggac tcccttttcaa   2460 cccaaacaat gacaatggac catacaacag cattccgcaa tcagcccccca ctaatttggg   2520 atctggtatc atggcagaag gaggtggagt accaatgggc aataatcaac agggtgctga   2580
tagagggaaa ttagcattgt gattctcaat ggatgggcca cagagtcacc acccgaaaag   2640
ctctctgggt cttgcctacc tgcaacaacc acctctacaa gcagttcaaa atagtgtcac   2700
```

```
cacaggcagt gccaacaact actttggctt cagcaccccc tgggggaatt ttgacttcaa    2760
cagattccac tgccacttca gcccctaga ctggcaaaga ctcatcaata caactgggg     2820 actgcgacct aaaaacctgc acttcaaact cttcaacatc caagtcaagg aggtcacaag   2880
gaggaatgtt gaaccacaa ttgctaataa ccttactagc atgattcaag tctttgcgga   2940
ctcagagtgt caactcccat acgtgatcag gagtgctcaa gagaggtgcc tactcccctt   3000
ccctcctgat gtgtttatgt tgcctcagta tggatattgt actttggaca gtgatgggaa   3060
aagtttagag aggagcacat tctactttct agaatatttt cctaaccaaa tattgagaac   3120
gggtaacaac tttgcatttt cctatgcttt tgaatctgtc ctcttttata gcatgtggat   3180
acataatcag accttggata gattgatgaa tccattgatt gatcaatatc tgtatagatt   3240
tgataatcca acttgtggaa acactgttaa tcccaccttc acttacaaaa agggatcagc   3300
aggtgatatg tcttctcagg ctaggaactg gttgcctggt cctatgctta ggaatcaggg   3360
actaaaggat ggtcctaaca atcaggccaa tttagatggt tggaggatca gtcctccaat   3420
ggtgatcaat ggaaaatctt ctattatatt tcctgggcca tccatgtata ccgcatacaa   3480
tgctgcagat gaactggagg ttcaacctag cattaatctc cccatctttg ctaaagatgc   3540
ctctgtacct gaatccacca taattagtag tattggtaat caagatctta atagtaaatt   3600
gttagtcact aatgagaacg aggtcgggaa agtgaatgct actgctgcta atacctgggg   3660
gtctatggca gtcaaccagc agtctcccac ccccactagt gcactaaatc aaatgagtgt   3720
catgcctgga atggtctggc agaatagaaa catcaatctc catggtccca tttgggctaa   3780
gattcctcac acagatggtt acttccatcc ctctcctctt atgggtggct ttggtctcaa   3840
acatcctcct cctcagaata tgattaaaaa ctctcctgtc cctgctaacc ccaccaccat   3900
cttcactcct gtcaaacaaa actctttcat cactcaatac tctattggtc aagtgactgt   3960
agaaattgaa tgggaactcc ataaggaaag ttccaagaaa tggactccta aaatccagtt   4020
tacttccaat ttcagaaaca ctattgactt acctttgct cccaacaatg aaggtgtata   4080
ctatgaacct cgtcccattg ctacctgata cctacccctt cccatcgaac tgtattgcac   4140
atatttcata tttgtatttt tttattcaat aaactgatgt attcatttca ttgtattcct   4200
cttatcactt ggctcttata agcagacgat gagctgccgt gggttggctt tcacaggagg   4260
cgtggtctca ttaaaatctt atggagaatg tggtcactcc tttgatcctt ctgcttactc   4320
a                                                                  4321
```

<210> SEQ ID NO 9
<211> LENGTH: 4324
<212> TYPE: DNA
<213> ORGANISM: Macropus giganteus
<400> SEQUENCE: 9

```
agagccagcg atcaaagaag tggccacact ctccttaaga tttgaaaagc ccaccaaagc     60
agatgatgta attacccata atgcaattgg aatcagtccc agactgcatt gcaagaggct    120
ataaaaagta ggatgtgtgc ctagaaattc attaatcacc taccgactga gcgagtgtgc    180
atcaaaagaa gaagaataaa tagaagagat gaagacatgt ggagctggaa cacgtgaag    240 ttttatgagg caattttctt tgtgcccaga gacttggagt ctgacatccc tggctatcct    300
aaaagactgg tcactcagat agaagagacc aagtggacgc tttcagaaaa ggacaacctg    360
gacctggaag ctttggagag tcgacaggta acacttgccc atctattctc ccgcaaattc    420
```

```
cttaagcact gggagtacct gacaagaaat cgagaattca atactatgt ccagctgaaa    480 aagggtgaga tctattacca tttacatatg cttttttgaga ccagtggaat tcagtccatg   540
gtgctcagcc gttacaccag ccagatcaag accccgctgc gagctaaagt ctctaacaat   600
gctgaggtta atatcaaaaa ctgaaaactg actggccatt acaacgacta aggccaccgg   660
gggggtcaac caaacaggtg gactataatt gcatcaactg gtatttaata gcataaaaac   720
aaccagaatt tcagtgggggg tggacaaata ttgaggaata taaggacttg atcctcaata   780
tccccgccag accgcagctc gtaggctagt tcttcacata gacctacttc gctcctgggg   840
tgagtgactc ccaatcctct taaatctcta atacttctgg tgctcttcta ttgtttataga   900 aatactgaga gatacatgga gcttgtaaat tggcttgtgg agcagcacct ctgaaaagca   960
gtggattatt gaaaatcagg aaagttatct ctgtcaccaa tccactagca atggagccag  1020
gaagattaaa gttgctcggg acaatgcttc taaaattatg aatctgacca aaaatgcaga  1080
tgattacctt atcccaaaag aatttgtcag ttttgataac attaaacaga accatatcta  1140
ttggatcttt aagaatggat agggatctat cctggtgggc tgggccagaa aagaatttgg  1200
caaaagaaac accatctggg tctatagaaa ggccactact gggaacacta acattgtgga  1260
agccgttgca cacatggtgc ccttctacag gtatgtgaat tggactaatg agaacttttcc  1320 attcaatgat tgtgtggata aaatgctcat ctggtgggag gaaggcaaga ttacctctat  1380
ggtggttgag acagctaaag ccatcctcgg aggagctaaa gttcaggtgg accaggaatg  1440
taagtcctct gttcaaattg attgtactcc agtcttcatt acctccagca ccaacatgtg  1500
ctacgaggta gatcagaaca ctatgatctt cgagcacaag cagttgttac aagaccacat  1560
gttttaattc atgctcatgg agagacttcc tgatgacttt ggcaaggtga caaaggagga  1620
ggtgcagcag ttcttttaaa tgggcagctg ttaatcaaat tccccctgag caggaattca  1680
ctgtcaagaa gattatgtca tccattgact gttagtgtga ccacaagcag aaacgggagg  1740
agtatccctc aactttctat caaggggggct ataaaaaggg cgagcctccc tcaaaaaagt  1800
tctttccatt tcggcatttg aagaaaattg aggtcatcga gcagagagcc cccacaatgg  1860
aattgaactt tgaaaatctc aaaaggtttg gtctcaatgt aattcccgct tctgatccta  1920
ttgctttgga tgactgtcag gatgaggaat aaatccctag atgtcttttt tggagaaatt  1980
tgaggactgg tacaaaaagt cagctgctat ttggagacac cttgaagctg cccacctca   2040 tcctaaagct aatcaacaac atcaagatga ttctcatgga ctggttctgc caggctataa  2100
gcatcttatt ccctttaatg gtctctataa gggagagcca gttaatcaag cagacaaagc  2160
cacacttgaa gaagagaaag cctatgatca attcctcaaa gaagggggaaa atccttttcct  2220 cacctacaac cacacagacc aagagttcca ggaaaagctt tcggagggca cttcgtttgg  2280
tggtaacctt ggcaaggcag tgtttcaagg aaagaaatga ctgcttaagc cattaggagt  2340
agtagaacca gacctggagc ctgtgaaagg agaaactcct gagaagctgt gcatccctca  2400
gcaactccaa atccctcctc cttcttctga agaggactcc ctttcaaccc aaacagtgac  2460
aatggaccat acaacagcat tcagcaatca gcccccacta atttgggatc tggtatcatg  2520
gcagaaggag gtggagtacc aatgggcaat aatcaacagg gtgctgatag agtaggtaat  2580
tcttcgggaa attagcattg tgattctcaa tggatgggcc acagagtcac cacccgaaaa  2640
gctctctggg tctagcctac ctgcaacaac cacctctaca agcagttcaa atagtgtca   2700 ccacaggcag tgccaacaac tactttggct tcagctccac ctgggggaat tttgacttca  2760
acagattcca ctgccacttc agccccctag actagcaaag acttatcaat aacaactggg  2820
```

```
gactgagacc taaaaacctg cacttcaaac tcttcaacat ccaagtcaag gaggtcacaa    2880
ggaggaatgt tgaaaccaca attgctaata accttaccag catgattcaa gtctttgcgg    2940
actcagagtg tcaactccca tatgtgatca ggagtgttca agagaggtgc ctactcccct    3000
tccctcctga tgtgtttatg ttgcctcagt atggatattg tactttggac aatgatggga    3060
aaagtttaga gaggagcgca ttctactttc tagaatattt ttctaaccaa atattgagaa    3120
cgggtaacaa ctttgcattt tcctatgctt ttgaatctgt cccctctcat agcatgtgga    3180
tacataatca gagcttggat agattgatga atccattgat tgatcaatat ccgtatagat    3240
ttgataatcc aacctgtgga aacactgtta atcccacctt cacttacaaa agggatcag    3300 caggtgatat ggcttttcaa actggttgcc tggtcctatg cttaggaatc agggactaaa    3360
ggatggtcct aacaatcagg ccaatttaga tggttggagg atcagtcctc caatggtgat    3420
caatggaaaa tcttctatta tatttcctgg gccatccatg tataccgcac acagtgctgc    3480
agatgaactg gaggttcaac ctagcattaa tctccccatc tttgctaaag atgcctctgt    3540
acctgaatcc accataatta gtagtattgg taatcaagat cctaatagta aattgttagt    3600
cactgatgag aacgaggtcg ggacagtgaa tgctactgct gctaataccc tggggtctat    3660
ggcagtcaac cagcagactc caccccccac tagtgcagga caggttctaa atcaaatgag    3720
tgtcatgcct ggaatggtct ggcagaatag agacatcaat ctccatggtc ccatttgggc    3780
taagattcct cacacagatg gttacttcca tccctctcct tttataggtg gctttggtct    3840
caaacatcct cctcctcaga atatgattga aaactctcct gtccctgcta accccaccac    3900
catcttcact cctgtcaaac aaaactcttt tatcactcaa tactctattg gtctagtgac    3960
tgtagaaatt gaatgggaac tccataagaa aagttccaag aaatggactc ctgaaatcca    4020
gtttacttcc aatttcagaa acactattga cttacctttt gctcccaaca atgaaggtgt    4080
atactgtgaa cctcatccca ttggtacctg ataccttacc cttcccatct aactgtattg    4140
cacatatttc atatttgtat ttttttattc aataaactga tgtattcatt tcattgtatt    4200
tctcttatca cttggctctt ataagcagac aatgagctgc cgtgagttgg ctttcccagg    4260
aggagtggtc tcattaaaat cttatggaga atgtggtcac tcctttgctc cttctgcttg    4320
ctca                                                                 4324
```

<210> SEQ ID NO 10
<211> LENGTH: 4353
<212> TYPE: DNA
<213> ORGANISM: Macropus eugenii

<400> SEQUENCE: 10

```
agagccagtg atcaaagaag tggccacact ctccttaaga tttgaaaagc ccaccaaagc      60
agatgatgta attacccata atgcaattgg aatcagtccc agactgcatt gcaagaggct     120
ataaaaagaa ggatgtgtgc ctagaaattc attaatcatc tactgactga gcgagtgtgc     180
atcaaaagaa gaagaataaa tagaagagat gaagacatgc tggagctgga cacgtgaag     240 ttttatgagg caattttcct tgtgcccaga gacttggagt ctgacatccc tggctatcct     300
aagagactgg tcactcagac rraacagacc argtggatgc tttcagaaaa ggacaacctg     360
gacttggaag ctttggagag tcgacaagta acatttgccc atctattctc tcgcaaattc     420
cttaatcact gggagtacct gacaagaaat cgagaattca atactatgt ccagctgaaa     480 aagggtgaga tctattacca tttacatatg ctttttgaga ccagtggaat tcagtgcatg     540
```

```
gtgctcagtc gttacatcag tcagatcaag acctcgctgt gagctaaagt ctctaacaat    600
gctgaggtta ataacaaaaa ctgaaaactg actggccatt acgacgacta aggccacggg    660
ggggtggtgg ggtgtcaacc aaacaggtgg actataattg catcaactgg tatttaatag    720
cataaaagca accagaattt cagtgggggt ggacaaatat tgaggaatat aaggacttaa    780
tccttaatat ccccgccaga ccgcagctta taggctagtt cttcacatag acctacttcg    840
ctcctgggt gagtgactcc caatcctctt aaatctctaa tacttctggt gctcttctat     900
tgttatagaa atactgagag atacatggag cttgtaaatt ggcttgtgga gcagcacctc    960
tgaaaagcag tggattattg aaaatcagga aagttatctc tgtcaccaat ccactagcaa   1020
tgcagccagg aagattaaag ttgctctgga caatgcttct aaaattatga atctgaccaa   1080
aaatgcagat gattacctta tcccgaaaga atttgtcagt tttgacaaca ttaaacagaa   1140
ccatatctat tggatcttta agaatggata cggatctatc ctggtaggct gggccagaaa   1200
agaatttggc aaaagaaaca ccatctgggt ctatggaaag gccactactg gaacactaa    1260
cattgtggaa gccgttgcac acacggtgcc cttctacggg tatgtgaatt ggactaatga   1320
gaacttcca ttcagtgatt gtgtggataa aatgctcatc tggtgggagg aaggcaagat    1380
tacctctatg gtggttgaga cagctaaagc catccttgga ggagctaaag ttcaggtgga   1440
ccaggaatgt aagtcctctg ttcaaattga ttgtactcca gtcatcatca cctccaacac   1500
caacatgtgc tacatggtgg atcggaacac tatgatcttt gagcataagc agttgttaca   1560
agaccacatg tttcaattca tgctcgtgga gagacttcct gatgactttg caaggtgac    1620
aaaggaggag gtgcgtcagt tcttttaaat gggcagctgt taatcaaatt ccccctgagc   1680
aggaattcac tttcaagaag attatgtcat ccattgactg ttattatgac cacaagcaga   1740
aatgggagga gtatccctcg actttctatc aaggggggcta taaaaaggcc gagcctccct  1800
cgaaaaagtt cttttccattt cgggatttga agaaaattga agtcatcgag cagagagtcc  1860
ccacagtgga attgaacttt gagaatctca aaaggtttgg tctcaatgta attcccactt    1920
ctgatcctat tgctttggat gactgtcagg atgaggaata aatccctaga tgtctttttt    1980
ggagaaattt gaggactggt acaaaaagtc agctgctatt tggagacacc ttgaagctgg   2040
cccacctcat cctaaagcta atcaacaaca tcaagatgac tctcatggac tggttctggc   2100
aggctataag tatcttattc cctttaatgg tctctataag ggggagccag ttaattaagc   2160
agacaaagcc acactcgaac aagagaaagc ctatgatcaa ttcctcaaag aaggggaaaa   2220
tcctttcctc acctacaacc acacagacca agagttccag gaaaaacttt cagagggcac   2280
ttcatttggt ggtaaccttg gcaaggcagt gtttcaagga aagaaatgac tgcttaagcc   2340
attaggagca gtagaaccag acctggagcc tgtgaaagga gaaactcctg agaagctgtg   2400
catccctcag caactcaaaa tccctcctcc ttcttctaaa agacaaaaga caagaggact   2460
ccctttcaac ccaaacagtg acaatggacc atacaacagc attcagcaat cagcccccac   2520
taatttggga tctggtatca tggcagaagg aggtggagta ccaatgggca ataatcaaca   2580
gggtgctgat agagtaggta attctttggg aaattagcat tgtggttctc aatggatggg   2640
ccacagagtc accaccgaa aagctctctg ggtctcgcct acctgcaaca accacctcta    2700
caagcagttc aaaatagtgc caccacaggc agtgccaaca actactttgg cttcagctcc   2760
ccctggggga tttttgactt caacagattc cactgccact tcagcccctg agactggcaa   2820
agacttatca ataacaactg gggactgcga cctaaaaacc tgcacttcaa actcttcaac   2880
atccaagtca aggaagtcac aaggaggaat gttgaaacca caattgctaa taaccttacc   2940
```

```
agcatgattc aagtctttgc ggactcagag tgtcaactcc catatgtgat caggagtgct    3000
caagagaggt gcctactccc cttccctcct gatgtgttta tgttgcctca gtatggatat    3060
tgtactttgg acaatgatgg gaaaagttta gagaggagcg cattctactt tctagaacat    3120
tttcctaacc aaatattgag aatgggtaac aactttgcat tttcctatgc ttttgaatct    3180 gtccccttc atagcatgtg gatacataat cagagcttgg atagattgat gaatccattg    3240
attgatcaat atctgtatag atttgataat ccaacctgtg gaaacactgt taatcccacc    3300
ttcacttaca aaagggatc agcaggtgat atggcttctc aggctaggaa ctggttgcct    3360
ggtcctatgc ttaggaatca gggactaaag gatggtccta acaatcaggc caatttagat    3420
ggttggagga tcagtcctcc aatggtgatc aatggaaaat cttctattat atttcctggg    3480
acatccatgt gtaccgcaca caatgctgca gatgaactgg aggttcaacc tagcattaat    3540
ctctccatct ttgctaaaga tgcctctgta ccagaatcca ccataattag tagtattggt    3600
aatcaagatc ctaatagcaa attgttagtc actgatgaga acgaggtcgg gacagtgaat    3660
gctactgctg ctaatacctg ggggtctatg gcagtcaacc agcagactcc cacccccact    3720
agtgtaggac aggttctaaa tcaaatgagt gtcatgcctg gaatggtctg gcagaaaaga    3780
gacatcaatc tccatggtcc catttgggct aagattcctc acacagatgg ttacttccat    3840
ccctctcctc ttatgggtgg cttggtctc aaacaatctc ctcctcagaa tatgattaaa    3900
aactctcctg tccctgctaa ccccaccacc atcttcactc ttgtcaaaca aaactctttt    3960
atcactcaat actctattgg tcaagtgact gtagaaattg aatgggaact ccataaggaa    4020
agttccaaga aatggactcc tgaaatccat tttacttcca atttcagaaa cactattgac    4080
ttatcttttg ctcccaacaa tgaaggtgta tactgtaaac ctcgtcccat ggtacctga    4140 taccttaccc ttcccatcta actgtattgc acatatttca tgtttgtatt ttttattca    4200 ataaactgat gtattcattt cattgtattt ctcttatcac ttggctctta taagcagacg    4260
atgagctgcc gtgggttggc tttcacagga ggagtggtct cattaaaatc ttatggagaa    4320
tgtggtcact cctttgctcc ttctgcttgc tca                                 4353
```

<210> SEQ ID NO 11
<211> LENGTH: 4357
<212> TYPE: DNA
<213> ORGANISM: Lagorchestes conspicillatus

<400> SEQUENCE: 11

```
agagccagtg atcaaagaag tggccacact ctccttaaga tttgaaaagc ccaccaaagc     60
agatgatgta attacccata atgcaattgg aatcagtccc agactgcatt gcaagaggct    120 ataaaagaa ggatgtgtgc ctagaaattc attaatcatc taccaactga gcgagtgtgc    180
atcaaaagaa gaagaataaa cagaagagat gaagacatgc tggagctgga acacgtgaag    240
ttttatgagg caattttcct tgtgcccaga gacttggagt ctgacatccc tggctatcct    300
aagagactgg tcactcagat agaagagacc aagtggacgc tgtcagaaaa ggacaacctg    360
gacttggaag ctttggagag tcgacaggta acatttgccc atctattctc ccgcaatttc    420
cttaagcact gggagtacct gacaagaaat ggagaattca aatactacgt ccagctgaaa    480
aagggtgaga tctattacca tttacatatg ctttttgaga ccggtggaat tcagtctatg    540
gtgctcagcc attacatcag ccagatcaag acctcgctac cagctaaagt ctcttaacaa    600
tgctgaggtt aatatcgaaa actgaaaact gactggccat tacgatgact aaggccaaag    660
```

```
aggggggtcaa ccaaacaggt ggactataat tgcatcaact ggtatttaat agcataaaaa    720
caaccagaat ttcagtgggg gtggacaaat attgaggaat ataaggactt gatcctcaat    780
atccctgcca raccgcaact cgtaggctag ttcttcacat agacctactt cgctcctggg    840
gtgagtgact cccaatcctc ttaaatctct aatacttctg gtgctcttct attgttatag    900
aaatactgag agatacatgg agcttgtaaa ttggcttgtg gagcagcacc tctgaaaagc    960
agcggattat tgaaaatcag gaaagttatc tctgtcacca atccactagc aatggagcca   1020
ggaagattaa agtcgctctg aacaatgctt ctaaaattat gaatctgacc aaaaatgcag   1080
atgattacct tatcccgaaa gaatttgtca gttttgataa cattaaacag aaccatatct   1140
attggatctt taagaatgga tacagatcta tcctggtggg ctgggccaga aaagaatttg   1200
gcaaaagaaa caccatctgg gtctatggaa aggccactac tgagaacact aacattgtgg   1260
aagccgttgc acacacagtg cccttctacg ggtatgtgaa ttggactaat gagaactttc   1320
cattcaatga ttgtgtggat aaaatgctca tctggtggga ggaagtaag attaccttta   1380 tggtggtcga gacagctaaa gccatcctca gaggagctaa agttcaggtg gatcaggaat   1440
gtaagtcctc tgttcaaatt gattgtactc cagtcatcat tacctccaac accaacatgc   1500
gctacgtggt agatcggaat accatggtct ttgagcacaa gcagttgtta caagaccaca   1560
tgtttcaatt catgctcgtg gagagacttc ctgatgactt tggcaaggtg acaaaggagg   1620
aggtgcgtca gttcttttaa atgggcagct gttaatcaaa ttcccctga gcaggaattc   1680 actgtcaaga gattatgtc atccattgac tgttattatg accacaagca gaaatgggag   1740
gagtatcctt cgactttcta tcaaggggc tatgaaaagg acgagcctcc ctcgaataag   1800
ttctttccat tttgggattt gaagaaaatt gaggtcattg agcagagagc ccccacagtg   1860
gaattgaact ttgagaatct caaaaggttt ggtctcattg taattcccgc ttctgatcct   1920
attgctttgg atgactgtca ggatgaggaa taaaccccct agatgtcttt tttggagaaa   1980
tttgaggact ggtacaaaaa gtcagctgct atttggagac accttgaagc tggcccacct   2040
catcctaaag ctaatcaaca tcaagatgac tctcatggac tggttctgcc aggctataaa   2100
tatcttattc cctttaatgg tctctataag ggggagccag ttaatcaagc agacaaagcc   2160
acacttgaac aagagaaagc ctatgatcaa ttcctcaaag aaggggaaaa tccttttcctc   2220 acctacaacc acacagacca agagttccag gaaaaacttt cggagggcac tttgtttggt   2280
ggtaaccttg gcaaggcagt gtttcaagga agaaatgac tgcttaagcc attaggagta   2340
gtagaaccag acctggagcc tgtgaaagga gaaactcctg agaagctgtg catccctcag   2400
caactccaaa tccctcctcc ttcttctaaa tgacaaaaga caagaggact cccttttcaac   2460 ccaaacagtg acaatggacc atacaacagc attcagcaat cagccccac taatttggga   2520 tctggtatca tggcagaagg aggtggaata ccaatgggca acaatcaaca gggtgctgat   2580
agagtaggta attcttcggg aaattagcat tgtgattctc aatggatggg ccacagagtc   2640
accacccaaa aaactctctg gtcttgcct acctgcaaca accacctcta caagcagttc   2700
aaaatagtgt caccacaggc agtgccaaca actactttgg cttcagcacc cctggggaa   2760 ttttgacttc aacagattcc actgccactt cagcccctga gactggcaaa gacttatcag   2820
taacaactgg ggactgcgac ctaaaaacct gcacctcaac ctcttcaaca tccaagtcaa   2880
ggaggtcaca aggaggaatg tcgaaaccac aattgctaat aaacttacca gcatgattca   2940
agtctttgcg gactcagagt gtcaactccc atacgtgatc aggagtgctc aagagaggtg   3000
cctactcccc ttccctcctg ttgtgtttat gttgcctcgg tatggatatt gtactttgga   3060
```

```
caatgatggg aaaagtttag ggaggagcac attctacttt ctagaatatt ttcctaacca    3120
aatattgaga atgggtaaca actttgcatt ttcctatgct tttgaatctg tcccctttca    3180
ttgcatgtgg atacataatc agagcttgga tagattgatg aatccattga ttgatcaata    3240
tctgtataga tttgatcatc aacctgtgg aaacactgtt aatcccacct tcacttacaa    3300
aaagggatca ccaggtgata tggcttctca gggtaggaac tggttgcctg gtcctatgct    3360
taggaatcag ggactaaagg atggtcctaa caatcaggcc aatttagatg gttggaggat    3420
cagtcctcca atggtggtca atggaaaatc ttctattata tttcctgggc catccatgta    3480
taccgcacac aatgctgcag atgaactgga ggttcaacct agcattaatc tccccatctt    3540
tgctaaagat gcctctgtac ctgaatccac cataattaat agtatcggta atcaagatct    3600
taatagtaaa ttgttagtca ctgatgagaa cgaggtcggg acagcgaatg ctgctgctgc    3660
taatacctgg gggtctatgg cagtcaacca gcagactccc accccaacta gtgcaggaca    3720
ggttctaaat caaatgagtg tcatgcctgg aatggtctgg cagaatagag acatcaatct    3780
ccatggtccc atttgggcta agattcctca cacagatggt tacttccatc cctctcctct    3840
tatggtctca aacatccctc ttctctttgg tctcaaacat cctcctcctc agaatatgat    3900
taaaaactct cctgtccctg ctaaccccac caccatcttc actcctgtca acaaaaactc    3960
tttcatcact caatactcta ttggtcaagt gactgtagaa attgaatagg aactccataa    4020
ggaaagttcc aagaaatgga ctcctgaaat ccagtttact tccaatttca gaaacactgt    4080
tgacttacct tttgctccca acaatgaagg tgtatactgt gaacctcgtc ccattggtac    4140
ctgataccct accccttccca tctaactgta tcgcacatat ttcatatttg tattatttta    4200
ttcaataaac tgatgtattc atttcattgt atttctctta tcacttggct cttataagca    4260
gacaatgagc tgccgtgggt tggctttcac aggaggcgtg gtctcattaa aatcttatgg    4320
agaatgtggt cactcctttg ctccttctgg ttgctca                             4357
```

<210> SEQ ID NO 12
<211> LENGTH: 4338
<212> TYPE: DNA
<213> ORGANISM: Setonix brachyurus

<400> SEQUENCE: 12

```
agagccagcg atcaaagaag tggccacact ctccttaaga tttgaaaagc ccaccaaagc      60
agatgatgca attacccata atgcaattgg aatcagtccc aggctgcatt gcaagaagct     120
ataaaaagaa ggatgtgtgc ctagaaattc atcaatcatc taccgactga gcgagtgtgc     180
atccaaagaa raaraataaa tagaagagat gaagacatgc tggagctgga atacctgaag     240
ttttatgagg caatttttcct tgtgcccaga gacttggagt stgacatccc tggctatcct     300
aaragactgg tcactcarat agaaragacc aagtggacgc tttcaraaaa ggacaacctg     360
gacttggaag ctttggagag tcgacaggta atatttgccc atctattctc ccgcaaattc     420
ctcaagcact gggagtacct gacaagaaat cgagaattca atactatgt ccagctgaaa     480 aagggtgaga tctattacca tttacatatg cttttttgaga ccagtggaat tcagtgcatg     540
gtgctcakcc attatatcag tcagatcaag acctctctga aactaaagt ctctaacaat     600 gctgaggtta atatcgaaaa ctgaaaactg actggccatt acgacgacta aggccaccgg     660
gggggtcaac caaacaggtg gattataatt acatcaactg gtatttaata gcataaaaac     720
aaccagaatt tcagtggggg tggacaaata ttgaggaata taaggacttg atcctcaata     780
```

```
tccccgccag accgcagctc gtaggctagt tcttcacata gacctacttc actcctgggg    840
tgagtgactc ccaatcctct taaatctcta atacttctgg tgctcttcta ttgttataga    900
aatactgaga gatacatgga gcttgtaaat tggcttgtgg agcagcacct ctgaaaagca    960
gtggattatt gaaaatcagg aaagttatct ctgtcaccaa tccactagca atggagccag   1020
gaatattcaa gtcgctctgg acaatgctcc taaaattatg aatctgacca aaaatgcaga   1080
tgattacctt atcctgaaag aatttgtcag ttttgacaac attgaacaga accatatcta   1140
ttggatcttt aagaatggat atggatctat cctggtgggc tgggccagaa aagaatttgg   1200
caaaagaaac accatctggg tctatggaaa ggccactatt gggaacgcta acattgtgga   1260
agccgttgca cacatggtgc ccttctacag gtatgtgaat tggactaatg agaactttcc   1320
attcaatgat tgtgtggata aaatgctcat ctggtgggag gaaggcaaga ttacctctat   1380
ggtggttgag acagctaaag ccatcctcgg aggagctaaa gttcaggtgg accaggaatg   1440
taagtcctct gttcaaattg atagtactcc agtcatcatc acctccaaca ctgacatgtg   1500
ctacgtggtg gatcggaaca ctatgatctt tgagcacaag cagttgttac aagaccacat   1560
gtttcaattc atgttcgtgg agagacttcc tgatgacttt ggcaaggtga caaggagga   1620 ggtgcatcat ttcttttaaa tgggcagctg ttaatcaaat tccccctgag tagggattca   1680
ctgtcaagaa gattatgtca tccattgact gttattatga ccacaagcag aaatgggagg   1740
agtatccctc aactttctat caagggggct ataaaaaggc tgagcctccc ttgaaaaagt   1800
tctttccatt tcgggatttg aagaaaattg aggtcatcga gcagagagcc cccacagtgg   1860
aattgaactt tgagaatctc aaaaggtttg gtctcaatgt aattcccgct tctgatccta   1920
ttgctttgga tgactgtcag gatgaggaat aaatccctag atgtcttttt tggagaaatt   1980
tgaggactgg tacaaaaagt cagctgctat ttggagacac cttgaagctg cccaccctca   2040
tcctaaagct aatcaacaac atcaagatga ctctcatgga ctggttctgc caggctataa   2100
gtatcttatt cccttttaatg atctctataa ggggagccaa gttaatcaag cagacaaagc   2160
cacactcaaa caagagaaag cctatgatca attcctcaaa gaagggaaa atcctttcct   2220 cacctacaac cacacagacc acgagttcca ggaaaaactt tcggaggaca cttcgtttgg   2280
tggtaacctt ggcaaggcag tgtttcaagg aaagaaatga ctgcttaagc cattaggagt   2340
agtagaacca gaactggagc ctgtgaaagg agaaactcct gagaagctgt gcatccctca   2400
gcaactccaa atccctcctc cttcttctaa acgacaaaag acaagaggac tccttttcaa   2460
cccaaacagt gacaatggac catacaacag cattcagcaa tcagccccac ttaatttggg   2520
atctggtatc atggcagaag gaggtggagt accgatgggc aataatcaac agggtgctga   2580
tagagtaggt aattcttctg gaaattagca ttgtgattct caatggatgg gcccacagagt   2640 caccacccga aaagctctct gggtctagcc tacctgcaac aaccacctct acaagcagtt   2700
caaaatagtg tcaccacagg cagtgccaac aactactttg gcttcagcac cccctggggg   2760
aattttgact tcaacagatt ccactgccac ttcagcccct gagactggca aagacttagc   2820
aataacaact gggtactgtg acctaaaaac ctgcacttca aactcttcaa catccaagtc   2880
aaggaggtca caaggaagaa tgttgaaacc acaattgcta ataaccttac cagcatgatt   2940
caagtctttg cggactcgga gtgtcaactc ccatacatga tcaggagtgc tcaagagcgg   3000
tgcctactct tcttccctcc tgatgtgttt atgttgcctc agtatggata ttgtactttg   3060
gacaatgatg ggaaaagttc agagaggagt gcattctact ttctagaata ttttcctaac   3120
caaatattga gaacgggtaa caactttgca ttttcctatg cttttgaatc tgtccccttt   3180
```

| | |
|---|---|
| catagcatat ggatacataa tcagagcttg catagattga tgaatccatt gattgatcaa | 3240 |
| tatctgtata gatttgacaa tccaacctgt ggaaacactg ttaatcccac cttcacttac | 3300 |
| aaaaagggat cagcaggtga tatggcttct caggctagga actggttgcc tggtcctatg | 3360 |
| ctgaggaatc agggactaaa ggatggtcct aacaatcagg ccaatttaca tggttggagg | 3420 |
| atcagtcctc caatggtgat caatggataa tcttctatta tatttcctgg accatccatg | 3480 |
| tataccgcat acaatgctgc agatgaactg gaggttcaac ctagcattaa tctccccatc | 3540 |
| tttgctaaag atgcctctgt acctgaatcc accataatta gtagtattgc taatcaagat | 3600 |
| cctaatagta aattgttagt cactgatgag aatgaggtcg ggacagtgaa tgctactgct | 3660 |
| gctaatacct gggggtctat gtcagtcaac cagcagactc ccaccccac tggtgcagga | 3720 |
| caggttctaa atcaaatgag tgtcatgcct ggaatggtct ggcagaatag agacatcaat | 3780 |
| ctccatggtc ccatttgggc taagattcct cacacagatg gttacttcca tccctctcct | 3840 |
| cttatggatg gctttggtct caaacatcct cctcctcaga atatgattaa aaactctcct | 3900 |
| gtccctgcta accccaccat catcttcact cctgtcaaac aaaactcttt catcactcaa | 3960 |
| tactctattg gtcaagtgac tgtagaaatt gaatgggaac tccataagga cagttccaag | 4020 |
| aaatggactc ctaaaatcca gtttactttc agaaacacta ttgacttacc ttttgctccc | 4080 |
| aacaatgaag gtgtatacta tgaacctcgt cccattggta cctgatacct tacccttccc | 4140 |
| atctaactgt attgcacata tttcatattt gtattttttt attcaataaa ctgatgtatt | 4200 |
| catttcattg tatttctctt atcacttggc tcttataagc agacgatgag ctgccttggg | 4260 |
| ttggctttca caggaggcgt ggtctcatta aaatcttatg gagaatgtgg tcactccttt | 4320 |
| gctccttctg cttgctca | 4338 |

<210> SEQ ID NO 13
<211> LENGTH: 4334
<212> TYPE: DNA
<213> ORGANISM: Onychogalea unguifera

<400> SEQUENCE: 13

| | |
|---|---|
| agagccagtg atcaaagaag trgccacact ctccttaaga tttgaaaagc ccaccaaagc | 60 |
| agatgatgta attacccata atacaattgg aatcagtccc agattgcatt gcaagaggct | 120 |
| ataaaaagaa ggatgtgtgc ctagaaattc attaatcatc taccgactga gcgagtgtgc | 180 |
| atcaaaagaa gaagaataaa tagaagaaat gaagacatgc tggagctgga acacatgaag | 240 |
| ttttatgagg caatttttcct tgtgcccara gacttggagt ctgacatccc tggctatcct | 300 |
| aagagactgg tcacccagat agaaragacc aagtggacac tttcaraaaa ggacaacctg | 360 |
| gacttggaag ctttggagag ttgacaggta acatttgccc atctattctc ccgcaaattc | 420 |
| cttaagcact gggagtacct gacaagaaat cgagaattca atactatgt tcagctgaaa | 480 |
| aagggtgaga tctattacca tttacatatg cttttttgaga ccagtggaat tcagtccatg | 540 |
| gtgctcagcc gttacatcag ccagatcaag acctcactga gagctaaagt ctctaaccat | 600 |
| gctgaggtta atatagaaaa ctgaaaactg actggccatt acgaccacta aggccaccgg | 660 |
| gggggtcaac caaacaggtg gactgtaatt gcatcaacct ggtatttaat agcataaacc | 720 |
| agaatttcag tggggtggga taaatattga ggaatgtaag gacttgatcc tcaatatccc | 780 |
| cgccagaccg cagctcgtag gctagttctt cacatagacc tacttcgctc tgggggtgag | 840 |
| tgactcccaa tcctcttaaa tctctaatac ttctggtgyt tttctattgt tatagaaata | 900 |

```
ctgagagata catggagctt gtaaattggt tgtggagca gcacctctga aaagcagtgg      960
attattgaaa atcaggaaag ttatctctgt caccaatcca ctagcaatgg agtcaggaag     1020
attaaagtct ctctggacaa tgcttctaga attatgagtc tgaccaaaaa tgcagatgat     1080
taccttatcc tgaaagaaty tgtcagtttc gataacatta aacagaacca tatctattgg     1140
atctttaaga ctggatatgg atctatcctg gtgggctggg ccagaaaaga atttggcaaa     1200
agaaacacta tctgggtcta tggaaaggcc actactggga acactaacat tgtgaagcc      1260 gttgcacaca cggtgccctt ctacggatat gtgaattgga ccaatgagaa ctttccattc     1320
aatgattatg tggataaaat gctcatctcg tgggagcaag gcaagattac ctttatggtg     1380
gttgagacag ctaaagccat cctcggagga gctaaagttc aggtggacca ggaatgtaag     1440
tcctctgttc aaattcattg tactccagtc ataattacct ccaacaccaa catgtgctat     1500
gtggtggatc agaacactat gatctttgag cacaagcagt tgttacaaga ccacatgttt     1560
caattcatgc tcgtggagag acttcctgat gactggcaag gtgacaaagg agggggtgcg     1620
tcagttcttt taaatgggca gctgttaatc aaattctgcc tgagcaggaa ttcattgtca     1680
agaagattat gtcatccatt gactgttatt atgaccacaa gcagaaatgg gaggagtatc     1740
cctcgacttt cttacaaggg ggctatgaaa agggtgagcc tccctcgaaa aagttctttc     1800
cattttggga tttgaagaaa attgaggtca ttgagcagag agcccccaca gtggaactga     1860
actttgagaa tctcaaaagg tttggtctca atgtaattcc cgcttctgat cctattgctt     1920
tggatgactg tcaggatgag gaataaaccc ctagatgtct tttttgtaga aatttgagga     1980
ctggtacaaa aagtcagctg ctatttggaa acaccttgaa gctggcccac ctcatcctaa     2040
agctaatcaa caacatcaag atgactctca tggactggtt ctgccaggct ataagtatct     2100
tattcccttt aatggtctct ataagggggg gccagttaat caagcagaca aagccacact     2160
caaacaagag aaagcctatg atcaattcct caaagaaggg gaaaatcctt tcctcaccta     2220
caaccacaca gaccaagagt tccaggaaaa actttcggag ggcacttcgt ttggtggtaa     2280
ccttggcaag gcagtgtttc aaggaaagaa atgactgctt aagtcattag gagtagtaga     2340
accatacctg gagcctgtgc aaggagaaac ttctgagaag ctgtgcatcc ttcagcaact     2400
ccaaattcct cctttttcta aacgacaaaa gacaagagga ctcccttaa  acccaaacag     2460 tgacaatgga ccatacaaca ccattcagca atcagccctc actaatgtgg gatctgatat     2520
catggcagaa ggaggtggag taccaatggg caataatcaa caggatgctg atagagtagg     2580
taattcttcg ggaaattagc attgtgattc tcaatggatg ggccacagag tcaccacccg     2640
aaaagctctc tgggtcttgc ctacctgcaa caaccacctc tacaagcagt tcaaaatagt     2700
gtcaccacag gcagtgccac caactacttt ggcttcagca ccctgtgggg gaattttgac     2760
ttcaacaaat tccactgcca cttcagcccc cgagactggc aaagacttat caataacaac     2820
tggggactgc gacctaaaaa cctgcacttc aaactcttca gcatccaagt caaggaggtc     2880
acaaggagga atgttgaaac cacaattgct aataaccttA ccagcatgac tcaagtcttt     2940
gcggactcag agtgtcaact cccatacgtg atcaggagtg ctcaagagag gtgtctactc     3000
cccttccctc ctgatgtgtt tatgttgcct cagtatggat gttgtacttt ggacaatgat     3060
gggaaaagtt tagagaggag cgcattctac tttctagaat attttcctaa ccaaatattg     3120
agaatgggta acaactttgc attttcctat gcttttgaat ctgtcccctt tcatagcatg     3180
tggatacata atcagagctt ggatagattg atgaatccat tgattgatca gtatctgtat     3240
agatttgtta atccaacctg tggaaacact gttaatccca ccttcactta caaaaaggga     3300
```

```
tcagcaggtg atatgactgc tcaggctagg aactggttgc ctggtcctat gcttaggaat    3360
cagggactaa aggatggtcc taacaatcag gccaatttag atggttggag gatcattcct    3420
ccaatggtga tcagtggaaa atcttctatt gcatttcctg gccatccat gtataccgca     3480 cacaatgctg cagatgaact ggaggttcaa cctagcacta atctccccac ctttgctaaa    3540
gatgcctctg tacctgaatc caccttaatt agtagtattg ataatcaaga tcctaatagt    3600
aaatgttagt cactgatgag aacgaggtca ggacagtgaa tgctactgct gttaatacct    3660
gggggtctat ggcagtcaac cagcagactc cccaccccca tagtgcagga caggttctaa    3720
atcaaatgag tgtcatgcct ggaatggtct ggcagaatag agacatcaat ctctatggtc    3780
ccatttgggc taagattcct cacacagatg gttacttcca tccctctcct cttatgggtg    3840
gctttggtct caaacatcct cctcctcaga atatgattaa aaactctcct gtccctgcta    3900
accccaccac catcttcact cctctcaaac aaaactcttt catcactcaa tactctattg    3960
gtcaagtgac tgtagaaatt gaatgggaac tccataagga aagttccagg aaatggactc    4020
ctgaaatcca gtttacttcc aatttcagaa acactattga cttacctttc gctcccaaca    4080
atgaaggtgt atactgtgaa cctcatccca ttggtacctg atatcttacc cttcccatct    4140
aactgtatcg cacatatttc atatctgtat ttttttattc aacaaactga tgtattaatt    4200
tcattgtatt tctcttatca cttggctctt ataagcagac aatgagctgc cgtgggttgg    4260 cttcacagg aggcgtggtc tcattaaaat cttatggaga atgtggtccc tcctttgctc     4320
cttctgcttg ctca                                                      4334

<210> SEQ ID NO 14
<211> LENGTH: 4340
<212> TYPE: DNA
<213> ORGANISM: Dendrolagus matschiei

<400> SEQUENCE: 14
agagccagcg atcaaagaag tggccacatt ctccttaaga tttgaaaagc ccaccaaagc      60
agatgatgta attacccata atgcaattgg aatcagtccc agactgcatt gcaagaggct    120 ataaaagaa ggatgtgtgc ctagaaattc attaatcatc taccgactga gcgagtgtgc     180
atcaaaagaa gaagaataaa tagaagagat gaagacatgc tggagctgga acatgtgaag    240
ttttatgagg caatttttcct tgtccccaga gacttggagt ctgacatccc tggctatccc    300
aagagactgg tcactcagat agaagagacc aagtggacac tttcagaaaa ggatgacctg    360
gacttggaag cgctggagag tggacaggta acatttgccc atctattctc ccacaaattc    420
cttaagcact gggagtacct gacaagaaat caagaattca ataccatgt ccagctgata     480 aaggggggaga tctattacca tttacatatg ctttttgaga ccagtggaat tcagtgcatg    540
gtgctcagcc gttacatcag ccagatcaag actttgcccc aagctgaagt ctctaacaat    600
gctgaggtta atatgaaaa ctggctggcc attacgacga ttaaggccac tgggggggtc     660
aaccaaacag gtggactata gttgcatcaa ctggtatta atagcataaa aacaatcaga     720
atttcagtgg gggtggacaa atattgagaa atataaggac ttgatcctca atatccccgc    780
cagactgcag ctcgcaggct agttcttcac atcgacctac ttggctcctg ggtgagtga     840 ttcccaatcc tcttaaatct ctaatacttc tggtgctctt ctattgtgat agaaatactg    900
agagatatgt ggagcttgta aattggcttg tggagcagca cctctgaaaa gcagtggatt    960
attgaaaatc aggaaagtta tctctgtcac caatccacta gaaatggagc caggaagatt   1020
```

```
aaagtcgctc tggacaatgc ttctaaaatt atgaatctga ccaaaaatga ggatgattac   1080
cttatcccga agaatttgt cagttttgac aacattaaac agaaccttat ctattggatc    1140
tttaagaatg tttactaccc tctttatgct ggatctatcc tggtgggctg gccagaaaa    1200 gaatttggca aaagaaacac catctggttc tatggaaagg ccacttctgg aatactaac    1260 attgtggaag ccattgcaca ctcagtgccc ttatatgggc atgtgaattg gactaatgag   1320
aactttccat tcagtgattg tgtggataaa atgctcatct ggtgggagga aggtgagatt   1380
acctctatgg tggttgagac agctaaagcc atccttgaag gagctaaagt tcaggtggac   1440
caggagtgta agtcctctct tcaaattgat tgtactccag tcatcatcac ctccaacatc   1500
aacatgtact acatggtgga ccagaacact atgatctttg aacacaagca gtcattacaa   1560
gaccacatgt ttcaattcat gctcatggag agactttctg atgactttgg aaaagtgaca   1620
aaggaggagg tgtgtcagtt ttttaaatgg gcagctgtta atcaaattcc tcctaagcag   1680
gaattcacta tcaagaagat tacatcatcc attaactgtt actatgacca caggcggaaa   1740
tgggaggagt atccctcgac tttctgtcaa ggggctata aaaggccaag cctccctcaa    1800
aaaagttctt tccattctgg gatttgaaga agttgaggt cattgagcag agagccccca    1860
cagtggattc ggacttcaag aatctcaaaa ggtttggtct caatgtaatt cttgcttctg   1920
ctttggttga ttgtcaagat gagcaataaa tccgtagatg tcttttttg gaaaaatttg    1980 aggactgata ggaaaagtta gctgctactt ggagacacct tgaatctggc ccacctcatc   2040
ctaaagctaa tcaacaacat caaaatgact ctcatggact ggttctgcca ggctataagt   2100
atctcattcc ctttaatggt ctctataagg gggagccagt taatcaaggg acaaagcca    2160 cactggagca agagaaagct tacaatcaat tcctcaaaga aggggaaaat ccttacctca   2220
cctacaacca cacagaccaa gagttccagg acctttcgga ggacactttg tttggtggta   2280
accttggcaa ggcagtgttt caaggaaaga aatgactgct taagccatta ggattagtag   2340
aaccagacct ggagcctgtg aaaggagaaa ctcctgagaa gctgtgcatc cctcagcatc   2400
tccaaatccc tcctcttcca tctaagcaac aaaagatgag aggactccct ttcaacacaa   2460
acagcgacaa tggagcatac accagcagtc agcaatcagt ccccactaat atgggatctg   2520
gtatcatggc agaaggaggt ggcacatgaa tgggcaataa tcaacagggt actgatggag   2580
taggtaattc ctcaggaaat taacattgtg attcccaatg gatgggccac agagtcgtca   2640
cctgaaaaac tctctgggtc ttgcccacct gcaacaattg cctctacaag cagttcaaag   2700
cagtgttacc acaggcagtg ccaacaacta ctttggcttc agaaccccct gggggaattt   2760
tgacttcaac agattccact gccacttcag cccctgagac tggcaaagac ttatcaataa   2820
taacttggga ctgtgaccta aaaacctgca cttcaaactc ctcaacatcc aagtcaagga   2880
ggtcacaagg aggaatgttg agaccacaat tgctaataac cttaccaaca tgattcaagt   2940
ctttgcggac tcaagagtgt taactcccat atgtgaccag gagtgctcaa gagaggtgtc   3000
tactcccctt ccctcctgat gtgtttatgt tgcctcaata tgggtattgt actttggaca   3060
atgatgggaa aagtttagag aggagtacat tctactgtct agtatatttt cctagctaaa   3120
tattgagaat gggtaacaac tttgaatttt cctatgcttt taaatctgtc ccctttcata   3180
gcatgtggat gcataatcag agcttggata gattgatgaa tccattgatt gatcaatatc   3240
tatatagatt tgataatcta ctccagtgga aacactgtta atcccacctt cacttacaaa   3300
aaggtatcag caggtggtat ggcttctcag gctaggaatt ggttacctgg tcctatgctt   3360
aggaatcagg gactaaaggg tggtcctaat aatcaggcca atctagatgg ttggaggatc   3420
```

```
agtcctccaa tggtgatcaa tggaaaatct tctattattt ttcctgggtc atccatgtat   3480
accgcacaaa atgttgcaga tgaactggag gttcaaccta gcattaatct ccctatcttt   3540
gctaaagatg cctctgtacc tgaatccacc ataattggta gtattggtaa tcaagatcct   3600
aatagtaaat tgttagtcgc tgatgagaat gaggtcggga cagtgaatgc tactgctgct   3660
attacctggg ggtttatggt agtcaaccag cagactccca cccccactac tgcaggatag   3720
gttctaaatc aaatgagtgt catgcctgga atgatctggc agaatagaga cattgatctc   3780
catagtccca tttgggctaa gattcctcac acagatggtt acttccatcc ctctcctctc   3840
atgggtggct ttggtctcaa acatcctctt cctcagaata tgattaaaaa ctctcctgtc   3900
cctgctaacc ctgccaccat cttcactcct gtcaaacaaa actctttcat cactcaatac   3960
tctattggtc aagtgactgt agaaattgaa tgggaactcc ataaggaaag ttccaagaaa   4020
tggaatcctg aaatccagtt tacttccaat ttcagaaaca ctattgactt acctttttgct  4080 cctaacaatg aaggtgcata ctctgaacct cgtcccattg gtactcgata ccttacccctt  4140 cccatctaac tgtattgcac atatttcata tttgtgtttt ttattcgata aactgattta   4200
ttcatttcat tgtatttctc ttatcacttg gctcttataa gcagacaatg agctgctgtg   4260
ggttggcttt cacaggaggc gtggtctcat taaaatctta tggagactgt ggtcactcct   4320
ttgctccttc tgcttgctca                                               4340

<210> SEQ ID NO 15
<211> LENGTH: 4343
<212> TYPE: DNA
<213> ORGANISM: Dendrolagus goodfellowi

<400> SEQUENCE: 15
agagccagcg atcaaagaag tggccacatt ctccttaaga tttgaaaagc ccaccaaagc     60
agatgatgta attacccata atgcaattgg aatcagtccc agactgcatt gcaagaggct    120
ataaaaagaa ggatgtgtgc ctagaaattc attaatcatc taccgactga gcgagtgtgc    180
atcaaaagaa gaagaataaa tagaagagat gaagacatgc tggagctgga acatgtgaag    240
ttttatgagg yaattttcct tgtccccaga gacttggagt ctgacatccc tggctatccc    300
aagagactgg tcactcagat agaagagacc aagtggacac tttcagaaaa ggatgacctg    360
gacttggaag cgytggagag tggacaggta acatttgccc atctattctc ccacaaattc    420
cttaagcact gggagtacct gacaagaaat caagaattca ataccatgt ccagctgawa    480 aagggggaga tctattacca tttacatatg cttttttgaga ccagtggaat tcagtgcatg    540
gtgctcagyc gttacatcag ccagatcaag actttgcccc aagctgaagt ctctaacaat    600
gctgaggtta atatggaaaa ctggctggcc attacgacga ttaaggccac tggggggggtc   660 aaccaaacag gtggactata gttgcatcaa ctggtattta atagcataaa aacaatcaga    720
atttcagtgg gggtggacaa atattgagaa atataaggac ttgatcctca atatccccgc    780
cagactgcag ctcgcaggct agttcttcac atcgacctac ttggctcctg gggtgagtga    840
ttcccaatcc tcytaaatct ctaatacttc tggtgctctt ctattgtgat agaaatactg    900
agagatatgt ggagcttgta aattggcttg tggagcagca cctctgaaaa gcagtggrtt    960
attgaaaatc aggaaagtta ctctgtcac caatccacta gaaatggagc caggaagatt    1020
aaagtcgctc tggacaatgc ttctaaaatt atgaatctga ccaaaaatga ggatgattac    1080
cttatcccga aagaatttgt cagttttgac aacattaaac agaaccttat ctattggatc    1140
```

```
tttaagaatg tttactaccc tctttatgct ggatctatcc tggtgggctg ggccagaaaa    1200
gaatttggca aaagaaacac catctggttc tatggaaagg ccacttctgg aataytaac     1260 attgtggaag ccattgcaca ctcagtgccc ttatatgggc atgtgaattg gactaatgag    1320
aactttccat tcagtgattg tgtggataaa atgctcatct ggtgggagga aggtgagatt    1380
acctctatgg tggttgagac agctaaagcc atccttgaag gagctaaagt tcaggtggac    1440
caggagtgta agtcctctct tcaaattgat tgtactccag tyatcatcac ctccaacacc    1500
aacatgtact acatggtgga csagaacact atgatctttg aacacaagca gtcattacaa    1560
gaccacatgt tcaattcat gctcatggag agactttctg atgactttgg aaaagtgaca     1620
aaggaggagg tgtgtcagtt ttttaaatgg gcagctgtta atcaaattcc tcctaagcag    1680
gaattcacta tcaagaagat tacatcatcc attaactgtt actatgacca caggcggaaa    1740
tgggaggagt atccctcgac tttctgtcaa gggggctata aaaggccaag cctccctcaa    1800
aaaagttctt tccattctgg gatttgaaga aagttgaggt cattgagcag agagccccca    1860
cagtggatty ggacttcaag aatctcaaaa ggtttggtct caatgtaatt cttgcttctg    1920
ctttggttga ttgtcaagat gagcaataaa tccgtagatg tcttttttg gaaaaatttg      1980 aggactgata ggaaaagtta gctgctactt ggagacacct tgaatctggc ccacctcatc    2040
ctaaagctaa tcaacaacat caaaatgact ctcatggact ggttctgcca ggctataagt    2100
atctcattcc ctttaatggt ctctataagg gggagccagt taatcaaggg gacaaagcca    2160
cactggagca agagaaagct tacgatcaat tcctcaaaga aggggaaaat ccttacctca    2220
cctacaacca cacagaccaa gagttccagg arracccttc ggaggacact tgtttggtg     2280 gtaaccttgg caaggcagtg tttcaaggaa agaaatgact gcttaagcca ttaggattag    2340
tagaaccaga cctggagcct gtgaaaggag aaactcctga gaagctgtgc atccctcagc    2400
atctccaaat ccctcctctt ccatctaagc aacaaaagat gagaggactc cctttcaaca    2460
caaacagcga caatggagca taccagcagc gtcagcaatc agtccccact aatatgggat    2520
ctggtatcat ggcagaagga ggtggcacat gaatrggcaa taatcaacag ggtactgatg    2580
gagtaggtaa ttcctcagga aattaacatt gtgattccca atggatgggc cacagagtcg    2640
tcacctgaaa aactctctgg gtcttgccca cctgcaacaa ttgcctctac aagcagttca    2700
aagcagtgtt accacaggca gtgccaacaa ctactttggc ttcagmaccc cctggggaa    2760 ttttgacttc aacagattcc actgccactt cagcccctga gactggcaaa gacttatcaa    2820
taataactrg ggactgtgac ctaaaaacct rcacttcaaa ctcttcaaca tccaagtcaa    2880
ggaggtcaca aggaggaatg ttgagaccac aattgctaat aaccttacca acatgattca    2940
agtctttgyg gactcaagag tgttaactcc catatgtgac caggagtgct caagagaggt    3000
gtctactccc cttccctcct gatgtgttta tgttgcctca atatgggtat tgtactttgg    3060
acaatgatgg gaaagttta gagaggagta cattctactg tctagtatat ttccctagct     3120
aaatattgag aatgggtaac aactttgaat tttcctatgc ttttaaatct gtcccctttc    3180
atagcatgtg gatgcataat cagagcttgg atagattgat gaatccattg attgatcaat    3240
atctatatag atttgataat ctactccagt ggaaacactg ttaatcccac cttcacttac    3300 aaaaggtat cagcaggtgg tatggcttct caggctagga attggttacc tggtcctatg     3360
cttaggaatc agggactaaa gggtggtcct aataatcagg ccaatctaga tggttggagg    3420
atcagtcctc caatgtgtgat caatggaaaa tcttctayta ttttttcctgg gtcatccatg   3480 tataccgcac aaaatgttgc agatgaactg gaggttcaac ctagcattaa tctccctatc    3540
```

```
tttgctaaag atgcctctgt acctgaatcc accataattg gtagtattgg taatcaagat    3600
cctaatagta aattgttagt cactgatgag aatgaggtcr ggacagtgaa tgctactgct    3660
gctattacct gggggtttat ggtagtcaac cagcagactc ccaccccac tactgcagga     3720
taggttctaa atcaaatgag tgtcatgcct ggaatgatct ggcagaatag agacattgat    3780
ctccatagtc ccatttgggc taagattcct cacacagatg gttacttcca tccctctcct    3840
ctcatgggtg gctttggtct caaacatcct cttcctcaga atatgattaa aaactctcct    3900
gtccctgcta accctgccac catcttcact yctgtcaaac aaaactcttt catcactcaa    3960
tactctattg gtcaagtgac tgtagaaatt gaatgggaac tccataagsa aagttccaag    4020
aaatggaatc ctgaaatcca gtttacttcc aatttcagaa acactattga cttacctttt    4080
gctcctaaca atgaaggtgc atactctgaa cctcgtccca ttggtactyg ataccttacc    4140
cttcccatct aactgtattg cacatatttc atatttgtat tttttattca ataaactgat    4200
ttattcattt cattgtattt ctcttatcac ttggctctta taagcagasg atgagctgct    4260
gtgggttggc tttcacagga ggcgtggtct cattaaaatc ttatggagac tgtggtcact    4320
cctttgctcc ttctgcttgc tca                                            4343

<210> SEQ ID NO 16
<211> LENGTH: 4341
<212> TYPE: DNA
<213> ORGANISM: Petrogale lateralis

<400> SEQUENCE: 16
agagccagcg aacaaagaag tggccacatt ctccttaaga tttgaaaagc ccaccaaagc      60
agatgatgta attacccata atgcaattgg aatcagtccc agactgcatt gcaagaggct     120
ataaaaagaa ggatgtgtgc ctagaaattc attaatcatc taccaactga gcgagtgtgc     180
atcaaaagaa gaagaataaa tagaagagat gaagacacgc tggagctgga acatgtgaag    240
ttttatgagg caattttcct tgtgcccaga gacttggagt ctgacatccc tggctatact    300
aagagactgg tcactcagat araagagacc aagtggacac tttcagaaaa ggacgacctg    360
gacttggaag cgttggagag tggacaggta gcatttgccc atctatyctg ccgcaaattc    420
cttaagcact gggagtacct gacaagaaat cgagaattca ataccatgt ccagctgaaa      480
aagggggaga tctattacca tttacatatg ctttttgaga ccagtggaat tcagtgcatg    540
gtgctcagcc attacatcag ccagatcaag accttgccgc aagctgaagt ctctaacgat    600
gctgagatta tatgtgaaaa ctggctggcc attacgggcga ttaaggccac tgggggggtc    660
aaccaagcag gtggactata gttgcatcaa ctggtattta atagcataaa acaatcaga     720
atttcagtgg gggtggacaa atattgagga atataaggac ttgatcatca atatccccac    780
cagactgcag ctcgcaggct agttmttcac atcgacctac ttggctcctg ggtgagtga      840
ctcccaatcc tcttaaatct ctaatacttc tggtgctctt ctattgtgat agaaatagca    900
agagatatgt ggagcttgta aattggcttg tggagcagca cctctgaaaa gcagtggatt    960
attgaaaatc ggraaagtta tctctgtcac caatccacta gaaatggagc caggaagatt   1020
aaagtcgctc tggacaatgc ttctaaaatt atgaatctga ccaaaaatga rgatgattac    1080
cttatcccaa aagaatttgt cagttttgac aacattaaac agaaccttat ctattggatc   1140
tttaagaatg tttactaccc tctttatgct ggatctatcc tggtgggctg gccagaaaa    1200
gaatttggca aaagaaacac catctggttc tatggaaagg ccactactgg gaatactaac   1260
```

-continued

```
attgcagaag ccattgcaca ctcggtgccc ttatatgggt atgtgaattg acaaatgag    1320
aactttccat tcaatgattg tgtggataaa atgctcatct ggtgggagga aggagagatt   1380
acctctatgg tggttgagac agctaaagcc atccttgaag gwgctaaagt tcaggtggac   1440
caggagtgta agtcctctct tcaaattgat tgtactccag tcatcatcac ctccaacacc   1500
aacatgtgct acatggtgga ctggaacact atgatctttg aacacaagga gtcattacaa   1560
gaccacatgt ttcaattcat gctcatggag agactttctg atgactttgg aaaagtggca   1620
aaggaggagg tgtgtcagtt ttttaaatgg gcagctgtta atcaaattct ccccaagcag   1680
gaattcacta tcaagaagat tacatcatcc attgactgtt actatgacca caggtggaaa   1740
tgggaggagt atccctccac tttctgtcaa gggggctata aaaggccgag cctccctcaa   1800
aaaagttctt tccgttctgg gatttgaaga agttgaggt cattgagcag agagccccca    1860
cagtggattc ggacttcaag aatctcaaaa ggtttggtct caatgtaatt cttgcttctg   1920
ctttggttga ctgtcaagat gagcaataaa tccatagatg tctttttcg aaaaatttg    1980
aggactgata ggaaaagtta gctgctactt ggagaaacct tgaatctggc ccacctcatc   2040
ctaaagctaa tcaacaacat caggatgact ctcatggact ggttctgcca ggctataagt   2100
atctcattcc ctttaatggt ctctataagg gggagccagt taatcaaggg acaaagcca    2160
cactggagca agagaaagct tacgatcaat cctcaaaga aggagaaaat cctgacctca    2220
cctacaacca cacagaccaa gagttccagg aaaaactttc ggaggacact tgtttggtg    2280
gtaaccttgg caaggcagtg tttcaaggaa agaaatgact gcttaagcca ttaggattaa   2340
tagaaccaga cctggagcct gtgaaaggag aaactcctga gaagctgcgc atccctcagc   2400
atctccaaat ccctcctctt ccatctaagc aacaaaagat gagaggactc cctttcaacc   2460
caaacagaga caatggagta tacaccagca gtcagcaatc agcccccact aatatgggat   2520
ctggtatcat ggcagaagga ggtggcacat gaatgggcaa taatcaacag agtactgatg   2580
gagtaggtaa ttcctcagga aattaacatt gtgattccca atggatgggc cacagagtca   2640
tcacctgaaa aactctctgg gtcttgccca cctgcaacaa ttgcctctac aagcagttca   2700
aagcagtgtc accacaggca gtgccaacaa ctactttggc ttcagcaccc cctgggggaa   2760
ttttgacttc aacagattcc actgccactt cagcccccga gactggcaaa gacttatcaa   2820
taataactgg ggactgtgat ctaaaaacct gcacttcaaa ttcttcaaca tccaagtcaa   2880
ggaggtcaca aagaggaatg ttgagaccac aattgctaat aaccttacca acatgattca   2940
agtctttgcg gactcagagt gttaactccc atatgtgacc aggagtgctc aagagaggtg   3000
tctactcccc ttccctcctg atgtgtttat gttgcctcaa tatgggtatt gtactttgga   3060
caatgatggg aaaagtttag agaggagtgc attctactgt cyagtatatt ttcctagcca   3120
aatattgaga acrggtaaca actttgaatt ttcctatgct tttaaatctg tccccttttca  3180
tagcatgtgg atgcataatc agagcttgga tagactgatg aatccattga ttgatcaata   3240
tctgtataga tttgataatc taaccagtgg aaacactgtt aatcccacct ttacttacaa   3300
aaaggtatca gcaggtgata tggcttctca ggctaggaat tggttacctg gtcctatgct   3360
taggaatcag ggactaaagg gtggtcctaa taatcaggcc aatctagatg gttggaggat   3420
cagtcctcca atggtgatca atggaaaatc ttctattatt tttcctgggt catccatgta   3480
tactgcataa aatgttgcag atgaactgga ggttcaacct agcattaatc tccctatctt   3540
tgctaaagat gcctctgtac ctgaatccac cataattggt agtattggta atcaagatcc   3600
taatagtaaa ttgttagtca ctgatgagaa tgaggtcggg acagtgaatg ctactgctgc   3660
```

```
tattacctgg gratttatgg cagtcaacca gcagactccc accccccacta ctgcaggata    3720 gtttctaaat caaatgagtg tcatgcctgg aatgatctgg cagaatagag acattgatct    3780
ccatagtccc atttgggcta agattcctca cacagatggt tacttccatc cctctcctct    3840
catgggtggc tttggtctca aatatcctct tcctcagaat atgattaaaa actctcctgt    3900
tcctgctaac cctgccacca tcttcactcc tgtcaaacaa aactctttca tcactcaata    3960
ctctattggt caagtgactg tagaaattga atgggaactc cataaggaaa gttccaagaa    4020
atggaatctt gaaatccagt ttacttccaa tttcagaaac actattgact tacctttgc     4080 tcccaacaat gaaggtgtat actctgaacc tcatcccayt ggtactcgat accttaccct    4140
tcccatctaa ctgtattgca catatttcat atttgtattt tttattcaat aaactgattt    4200
attcatttca ttgtatttct cttatcactt ggctcttata agcagacaat gagctgctgt    4260
aggttggctt tcacaggagg catggtttca ttaaaatctt atggagaatg tggtcactcc    4320
tttgctcctt ctrtttgctc a                                              4341

<210> SEQ ID NO 17
<211> LENGTH: 4348
<212> TYPE: DNA
<213> ORGANISM: Thylogale stigmatica

<400> SEQUENCE: 17
agagccagcg atcaaagaag tggccacatt ctccttaaga tttgaaaagc ccaccaaagc     60
agatgatgta attacccata atgcaattgg aatcagttcc agactgcatt gcaagaggct    120
acaaaaagaa ggatgtgtgc ctaaaaattc attaatcatc taccgactga gcgagtgtgc    180
atcaaaagaa gaagaataaa tagaagagat gaagacatgc tggagctgga acatgtgaag    240
ttttatgagg caattttcct tgtgcccaga gacttggagt ctgacatccc tggctatccc    300
aagagactgg tcactcaaat agaagagacc aagtggacac tttcagaaaa ggacgacctg    360
gacttggaag cattggagag tggacaggta acatttgccc atctattctc tcacaaattc    420
cttaagcact gggagtacct gacaagaaat cgagaattca ataccatgt ccagctgaaa     480 aagggggaga tctattacca tttacatatg attttgaga ccagtggaat tcagtgcatg      540
gtgctcagcc attacatcag ccagatcaaa accttgctgc aagctgaagt ctctaacaat    600
gctgaggtta atatgaaaa ctggctggcc attatgacga ttaaggccac tgggggggggg     660 ggggtcaacc aatcaggtgg actatagttg catcaactgg tatttaatag cataaaaaca    720
accagaattt cagtgggggt ggacaaatat tgaggaatat aaggacttga tcctcaatat    780
ccccgccaga gggcagctca cagggtagtt cttcacatcg acctgcttgg ctcctggggt    840
gagtgactcc caatcctctt aaatctctaa tacttctggt gctcttctat tgtgacagaa    900
ataccgagag atacgtggag cttgtaaatt ggcttgtgga gcagcacctc tgaaaaggca    960
gtggattatt gaaaatcagg aaagttatct catgtcacca atgccactag aaatggagcc    1020
aggaagatta agttgctmt ggacaacact tctaaaatta tgaatccgac caaaaatgag     1080
gatgattacc ttatcccgac agaatttgtc agttttgaca acattaaaca gaacttatct    1140
attggatctt taagaatgtt tactaccctc tttatgctgg atctatcctg gtgggctggg    1200
ccagaaaaga atttggcaaa agaaacacca tctggttcta tggaaaggcc actactggga    1260
atagtaacat tgcagaagcc attgcacact cagtgccgtt atatgggtat gtgaattgga    1320
ctaatgagac ctttccattc aatgattgtg tggataaaat gctcatctgg tgggaggaag    1380
```

```
gcgagattgc ctctatggtg gttgagacag ctaaagccat ccttgaagga gctaaagttc   1440
aggtggacca ggagtgtaag gcctctcttc aaattgattg tgctccagtc atcatcacct   1500
ccaacaccaa catgtgctac atggtggacc ggaacactat gatctttgaa cacaagcagt   1560
cattacaaga ccacgtttca attcatgctt gtggagagac tttctgatga ctttggaaaa   1620
gtgacaaagg aggaggggtg tcagtttttt aaatgggcaa ctgttaatca aattctccct   1680
aagcaggaat tcactatcaa gaagattaca tcatccattg actgttacta tgaccacagg   1740
tggaaatggg agaagtatcc ctggactttc cgtcaagggg gctataaaag gccgagcctc   1800
cctcaaaaaa gttctttcca ttctgggatt tgaagaaagt tgaggtcatt gagcagagag   1860
cccccacagt ggattcagac ttcaagaatc tcaaaaggtt tggtctcaat gtaattcttg   1920
cttctgcttt ggttgactgt caagatgagc aataaatccg tagatgtctt tttttggaaa   1980
aatttgtgga ctgataggaa aagttagctg ctacttggag acaccttgaa tctgcccac    2040 ctcatactaa agctaatcaa caacatcaag atgactctca tggactggtt ctgccaggct   2100
ataagtatct cattcccttt aatggtctct ataagggggga gccagttaat caaggggaca   2160
aagccacact ggagcaagag aaagcttatg atcaattcct caaagaaggg gaaaatcctt   2220
acctcaccta caaccacacg gaccaagagt tccaggaaaa acttttggag gacactttgt   2280
ttggtgataa ccttggcaag gcagtgtttc aaggaaagaa atgactgctt aagccattag   2340
gattagtaga accagacctg gagcctgtga aggagaaac tcctgaaaag ctgtgcatcc    2400
ctcagcatct ccaaatccct cctcttccat ctaagcaaca aaagatgaga ggactccctt   2460
tcaacccaaa cagcgacaat ggagcataca ccagcagtca gcaatcagcc cccactaata   2520
tgggatctgg tatcatggca gaaggaggtg gtgcatgaat aggcaataat caacagggta   2580
ctgatggagt aggtaattcc tcaggaaatt aacattgtga ttcccaatgg atgggccaca   2640
gagtcaccac ctgaaaaact ctctgggtct tgcccacctg caacaattgc ctctacaagc   2700
agttcaaagc agtgtcacca caggcagtgc caacaactac tttggcttca gcacccctg    2760 ggggaatttt gacttcaaca gattccactg ccacttcagt ccccgagact ggcaaagact   2820
tatcaataat aactggggac tgtgatctaa aaacctgcac ttcaaactct tcaacatcca   2880
agtcaaggag gtcacaagga ggaatgttga gaccacaatt gctaataacc ttaccgacat   2940
gattcaagtc tttgcagact caagaatgtt aactcccata tgtgaccagg agtgctcaag   3000
agaggtatct actcccctcc cctcctgatg tgtttatgtt gcctcaatat gggtattgta   3060
ctttggacaa tgatgggaaa agtttagaga ggagtgcatt ctactgtcta gtatattttc   3120
ctagccaaat attgagaacg ggtaacaact ttgaattttc ctatgctttt aaatctgtcc   3180
cctttcatag aatgtggatg cataatcaga gcttggatag attgatgaat ccattgattg   3240
atcaatatct atatagattt gataatctaa ccagtggaaa cactgttaat cccaccttca   3300
cttacaaaaa ggtatcagca ggtgatatgg cttctcaggc taggaattgg ttacctggtc   3360
ctatgcttag gaatcaggga ctaaagggtg gtcctaacaa tcaggctagt ctagatagtt   3420
gaaggatcag tcctccaatg gtgatcaatg gaaaatcttc tattattttt cctgggccat   3480
ccatgtatac cacacaaaat gttgcagatg aactggaggt tcaacctagc attaatctcc   3540
ctatctttgc taaagatgac tctgtacctg aatccaccat aattggtagt attggtaatc   3600
aagatcctaa tagtaaattg ttagtcactg atgagaatga ggtcgggaca gtgaatgcta   3660
ctgctgctat tacctggggg tttatggcag tcaaccagca gactcccacc cccactactg   3720
caggataggt tttaaatcaa atgagtgtca tgcctgggat gatctggcag aatagagaca   3780
```

```
ttgatctcca tagtcccatt tgggctaaga ttcctcacac agatggttac ttccatccct    3840
ctcctctcat gggtggcttt ggtctcaaac atcctctttc tcagaatatg attaaaaact    3900
ctcctgtccc tgctaaccct gccaccatct tcactcctgt caaacaaaac tctttcatca    3960
ctcaatactg tattggtcaa gtgactgtag aaattgaatg ggaactccat aaggaaagtt    4020
ccaagaaatg gaatcttgaa atccagttta cttccaattt cagaaacact attgacttac    4080
cttttgctcc caacaatgaa ggtgtatact ctgaacctcg tcccattggt actcgatacg    4140
ttacccttcc catctaactg tattgcacat atttcatatt tgtattttt attcaataaa    4200 ctgatttatt catttcattg tatttctctt atcacttggc tcttatatgc agatgatgag    4260
ctgctgtgcg ttggctttcg taggaggtgt ggtctcatta aaatcttatg gagaatgtgg    4320
ttactccttt gctccttctg cttgctca                                      4348

<210> SEQ ID NO 18
<211> LENGTH: 4340
<212> TYPE: DNA
<213> ORGANISM: Lagostrophus fasciatus

<400> SEQUENCE: 18
agagccaggg atcaaagaag tggccacact ctccataaga tttgaaaagc ctgccaaagc      60
agatgatgta attacccata atgcaattgg aatcagtccc agactgcatt gcaagaggtt     120
acaaaaagaa gagtgtatga ctagaaatgc attaatcacc cactgactga gcaagtatgc     180
atcaaaagaa gaagactaaa tagaagagat gaagacatgc tggagctgga acacgtgaag     240
ttttctgagg caatttccct tgtgcccaga gacttggagt ctgacatccc tggctatcct     300
aagagactgg tcgctcagat agaagagacc aagcggacac tttcagaaaa ggacgagctg     360
gacttggaag cggtggtgag tggacagcta acatttgccc atctattctc ccgcaaattc     420
cttaagcact gggagtacct gacaagaaat cgaaagttca atactatgt ccagctgaaa     480 aagggtgaga tctattacca tttatacatg cttttttgaga ccagtagaat tcagtccatg     540
gtgctcagcc gttacatcag ccagatcaag acctcgctgc aagcagaagt ctgtaacaac     600
gctgaggtta atacagaaaa ctgactggcc attacgacga ctaaggccac cgggggggat     660
caaccaaaca ggtggactat aattgcatca actggtatt aatggcataa aaacaaccag     720
aatttcagtg ggtgtggaca atattgagg aatataagga cttgatcctc aatatccctg     780
ccagactgca gctcgcaggc tagttcttta catcaaccta cttggctcct ggggtgagtg     840
actcccaatc ctcttaaatc tctaatactt ctggtgttcc cttctattgt gatagaaata     900
ctgagagata catggagttt gtaaattggc tcgtggagca gcacctctga aaagcagtgg     960
attactgaaa tcaggaaag ttatctctct caccaaatca ctagcaatgg agccaggcag    1020
attaaagtcg ctctggacaa tgcttctaaa attaagaatc tgaccaaaaa tgcagatgat    1080
taccttatcc cgaaagaatt tgtcagtttt gacaacatta acagaaccta tctcattgg     1140 agctttaaga atggatacga ccctctttat gctggatcta tcctggtggt ctgggttaga    1200
aaagagtttg gcaaaagaaa caccatctgg ttctatggaa aggccactac tgggaacagt    1260
aacattgcgg aagtcgttgc acacacggtg cccttatcag ggtatgtgaa ttggatttat    1320
gagaactttc cattcagtaa ctgtgtggat aaaatgctca tttggtggga ggaaggcgag    1380 attacccta aggtgactga gaaagctaaa gccatccttg gaggagctaa agttccagtg    1440
gaccaggaat gtaagtcctc tgttcaaact gattgtactc cagtcatcat cacctccaac    1500
```

```
accgacatgc gctacatggt ggacgggaac actatgatct ttgaacacaa gcagttgtta   1560
caagaccaca tgtttcaatt catgctcatg gagaggcttc ctcatgactt tggcaaggtg   1620
acaaaggagg aagtgagtta gttttttaaa atgggtagct gttaatcaaa ttcccctaa    1680 gcaggaattc actgtcaaga agattatgtc atccattgac tgttactatg ccacaagca    1740 gaaatgggag gagtatccct cgactttctg tcaagggggc tataaaaagg ctgagcctcc   1800
cttgaaaaag ttcttttccat tcagggatct gaagaaaatt gaggtcatca agcagagagc   1860
ccccacagtg gaatcggact ttgagaatct caaaaggttt ggtgtcaatg taattcccac   1920
ttctgatcct gttgctttgg atgactgtca ggatgagcag taaatccgta gatgtctttt   1980
ttggagaaat ttgaggaatg gtatgaaaag tcagctgcta cttggagatg ccttgaagtt   2040
ggcccacctc atcctaaagc taatcaacaa catcaagact actctcatgg actggttctg   2100
ccaggctata agtatctcat tccctttaat ggtctctata agggggagcc agttaatcaa   2160
gcaggcaaag ccactctgga acaagagaaa tcctacgatc aattcctcaa agaaggggaa   2220
aatccttacc tcacctacaa gcacacagac ccagagttcc aggaaaaact ttcagaggac   2280
acttcatttg gtgctaacct tggcaaggca gtgcttcaag gaaagaaacc tctgcttaag   2340
ccattaggag tagtagaacc agacctggat cctgtgaaag gagaaactcc tgagaagctg   2400
cacatccctc agcaactcca aatccttcct cctccatcta agggacaaaa gacgagagga   2460
ccccctttta accgaaacag caacaatgga gcatacacta gcagtcagcg atcagccccc   2520
actaatttgg gatctggtat cattgcagaa ggaggtggcg caccaatggg caataaccaa   2580
cagggtgcta atggagtagg taattcctca ggaaattagc attgtgattc ccaatggatg   2640
ggcaacatag tcgccacctg aaaaactctc tgggtcttgc ccacttgcaa caaccacctc   2700
tacaagcagt tcaaaacaat ggcaccacag gcagtgccaa caactacttt ggcttcagca   2760 cccctggg gtattttgac tttaacagat tccactgccc cttcagcccc tgagattggc    2820
aaagacttat caataacaac tgggaactgc aacctaaaaa cctgcgcttc aaactcttca   2880
acatccaagt caaggaggtc acaaggagga atgttgagac cacatttgct aataacctta   2940
ccagcatgat tcaagtcttt gtggactcag tgtcaactcc catacatgat caggtatgct   3000 caagagggt gtctacttcc cttccctcct gtgtgtttat gttgcctcag tatgggtatt    3060
gtaccttgga caatgatggg aaaagtttag agaggagtgc attctactgt ctagaatatt   3120
ttcctagcca atattgaga atgggcaaca gctttgaatt ttcctatgct tttgaatctg    3180
tccactttca tagcatgtgg atgcataatc agagcatgga tagattgata aatccattga   3240
ttgagcaata tctgtataga ttcgataatc taaccagtgg aaacactgtt aaccccacct   3300
tcacttacaa aaagggatca gcaggtgata tggcttctca ggctaggaat tggttacctg   3360
gtcttgtgct taggaatcag ggactaaagg atggtcttaa taatcagacc aatctagatg   3420 gttgaggat cagtcctcca gtggtgatga gtggaaaatc ttctattata ttccctgggc    3480
catccatgta tactgcccac aatgctgcaa atgaactgga gcattaatct ccttatcttt   3540
gctaaagatg cctctgtacc tgagtccacc ataattagta gttttggtaa tcaagatcct   3600
aatagtaaat tgttagtcac tgatgagaac gaggtcagga cagtgaatgc tactgctgct   3660
aacacctagg ggtctatggc agtcaatcag cagactccca cccccactag tgcaggacaa   3720
gttctaaatc aaatgagtgt catgcctgga atggtctggc agaatagaga cattgatctc   3780
catggttccg tttgggctaa gattcctcac acagatggtt acttccatcc ctctcctctc   3840
atgggtgcct ttggtctcaa acgtcctcct cctcagaata tgattaaaaa tactcctgtc   3900
```

| | |
|---|---|
| cctgctaacc ctgccaccat cttcactcct gtcaaacaaa attctttcat cactcaatag | 3960 |
| tctactggtc aagtgactgt agaaattgaa tgggaactcc ataaggaaag ttccaagaaa | 4020 |
| tgaactcctg aaatccagct tacttccagt ttcagaaaca ttattgactt acccttttgct | 4080 |
| cccaacaatg aaggtgtata ctctgaacct cattccattg gtacccaata ccttaccctc | 4140 |
| ccatctaact gtattgtata tacttcatgt ttgtattttt ttattcaata aactaattta | 4200 |
| ttcatttcat tgtacttctc ttgtcacatg gctcttataa gcagatgatg agctgccctg | 4260 |
| ggttggcttt cacgggaggc atggtctcat taaagtcttt tggagaatgt ggtcactcct | 4320 |
| tggctcattc tgcttgttca | 4340 |

<210> SEQ ID NO 19
<211> LENGTH: 3166
<212> TYPE: DNA
<213> ORGANISM: Aepyprymnus rufescens

<400> SEQUENCE: 19

| | |
|---|---|
| ggagtgagca agcaaagaag tggctacact ctccataaga tttgaaaagc ccaagcagat | 60 |
| gatgttaatt acccataatg caattagaat cagtcctaga ctgagttgca agaggctata | 120 |
| aaaagaaggg tgtatgccta aagttcatt atcatctacc aactgagcta gtgagcatca | 180 |
| aaggaagaag aataaataga agagatgaag acatgctgga gctggaacac gtgaagtttt | 240 |
| ataaggcaat tatccttgtg ccttgtcaga cttggagtct gacatccctg ctatcccaa | 300 |
| gaaactggtc actcagatag aagagaccaa gtggacactt tcataaaagg acgacctgga | 360 |
| cttggaagtg gtggaaagtg gacaggtaac atttgctcat ctattctact gcaaattctt | 420 |
| tgagcactgg gagtacctga caagaaatcg agaattcaaa tactatgtcc agctgaaaaa | 480 |
| gggtgagatc tattaccatt tacatatact ttttgggacc agtggaagtc agtcaatggt | 540 |
| gctcagccgt tacatcagcc agatcaagac ctcgctgcaa gctgaagtct ctaacaatgc | 600 |
| tgaggttaat atcgaaaact tactggccgt tacgactact aaggcctccc ggggagagtg | 660 |
| ggggggggg tcaaccaaac aagtggactt taactgcatc aattggtatt taatggcata | 720 |
| aaaacaacca gaatttccgt gggtgtggac aaatattgag gaatataagg acttgatcct | 780 |
| caatatcccc gccagactgt agcccgcagg ctagttcttc acatcgacct acttggctcc | 840 |
| cggggtgagt gactcccaat cctcttaaat ctctaatact tctggtgctc cctcctattg | 900 |
| tgacagaaat accgagagat acatggagct tgtaaattgg cttgtggagc agtacctctg | 960 |
| aaaagcagtg gattattgaa atcaggaaa gttatctctc tcaccaatcc actagcaatg | 1020 |
| gagccaggcg gattaaagtc gctctgaaca atgcttctaa aattatgaat ctgaccaaaa | 1080 |
| atacggatga ttatccttatc ctgaaagaat ttgtcagttt tgacaacatt aaacagaacc | 1140 |
| atatctgttg gatctttaag aatgggtacg accctcttta ttctggagct atcctggtgg | 1200 |
| gctggaccag gtaagaattc ggcaaaagaa acaccatctg attctgtgga aaggccacta | 1260 |
| ccgggaacac taacattgcg gaagccgttg cacacacggt gcctttatac gggtatgtga | 1320 |
| attgggctaa tgagaacttt ccattcaatg actgtgtgga taaatactc atctggtggg | 1380 |
| aggaaggtga gattacctct acggtggttg agacagctaa agccatcctt ggaggagcta | 1440 |
| aagttcaggt ggaccaggaa tctcagtcct ctgttcaaat tgattgtact ccagtcatca | 1500 |
| cctccaacac cctaaaaact ctctgggtct tacccacctg caacaaccac ctctacaagc | 1560 |
| agttgaaaac agtgtcacca caggcagtgc caacaaatac tttggcttca gcacctcctc | 1620 |

-continued

```
ggggcatgtt gacttcaaca gattccactg ccacttcagc ccctgagact ggcaaagact      1680
tatcaataac aactggagcc tgcgacctaa aaacctccac ttcaaacttc aacatccaag      1740
tcaaggaggt cacaaggagg aatgttgaga ccagcatgat tcaagtcttt gtggactcaa      1800
tgtcaactca cttatatgat caggagtgct caagaggggt gtctactccc cttccctcct      1860
gatgtgttta tgttgcctca gtatgggtat tgtactttgg acaatgatgg ggaaagttta      1920
gacaggagtg cattctactg tctagaatat tttcctagcc aaatgttgag aatgggtaac      1980
aactttgaat tttcctatgc ttttgaatct gtccccttcc atagcatgcg gttgcataat      2040
cagagcttgg atagattgat gaatccgttg attgatcaat atctgtacag atttgataat      2100
ctaaccaggg gaaacactgt taatcccacc ttcacttaca aaaagggatc agcaggtgat      2160
atggcttttc aggctaggaa ttggttacct ggtcctatgc ttagcaatca gggactgaag      2220
gatggtccta acaatcaggc caatctagat ggttagagga tcggtccttc aacggtgatc      2280
aatggaaaat cttctattat atttcctggg tcatccatgt ataccctcaca caatgctgca      2340 gatgaactgg aggtacaacc tagcattaat ctccctatct ttgctaaaga tgcctctata      2400
cctgaattct ctataattag tagtattggt agtcaagatc ctaatagtaa attgctagtc      2460
actgatgaga attaggtcgg gacatgaatg ctgttgctgc taatacctgg gggcttatgg      2520
cagtccatca gcagactccc acccctacta gtgcaggata ggttctaaat caaatgagtg      2580
tcatacctgg aatagtctgg cagaatagag acatcgatct ccatggtcct atttgggtta      2640
agatttctca cacagatggt tacttccatc cctctcctcc catgggtgtc tttggtctca      2700
aacatcctcc tcctcagaat atgattaaaa acactcctgt ctctgctaac cctgccacca      2760
tcttcactcc tgtcaaacaa aattctttca tcattcaata ctctactggt caagtgactg      2820
tagaaattga ggaaagttcc aagaaatgga atcctgaaat ccagttcact tccaatttca      2880
gaaacaccac tgacttacct tttgctccca acaatgaagg tgtatactct gaacctcatc      2940
ccattggtac ctgataccctt acccttccca tgtaactgta ttgtacatat ttcatatttg      3000 tatttttttat tcaataaact gatttattca tttcattgta cttctcttgg gatgtggctc      3060
ttataagcag atgatgagct gctgtgggtt ggctttcatg ggaggtgtgg tctcgttaaa      3120
atcttatgga gaatgtggtc actcttttgc ttgttctgct tgctca                     3166
```

<210> SEQ ID NO 20
<211> LENGTH: 2673
<212> TYPE: DNA
<213> ORGANISM: Hypsiprymnodon moschatus

<400> SEQUENCE: 20

```
agagcaagcg ggcaaaggag tggccacact ctccattaga tttgaaaagc ccgccaaagc       60
ggatgacgta attactcaga atgcaattga aatcagtccc agactgcatt gcgcaagaag      120
ctataaaaag aaaggcatac gccaagaaat tcattaatca tctaccaacc aagcgagtga      180
gcgtcaaaaa aagaagaata aatatgagat gaagatatgc cggagctgaa acacatcaag      240
ttttatgagg caattatctg catgcccaga gacttggagt ctgatgcccc tggctaccct      300
gagagactgg tcactcaggt agaagagacc aagtggatgc ttttggaaaa aaacgacctg      360
gacttggaag tggttgagag tggacaggta acattagccc aggtaacatt tgctcttctg      420
caaatcctta agcacgggga gtacctaaca agaaactaag aattcaaata ctatgtccag      480
ctggaaaagg gtgagatata ttaccattta catactcttt ttgagaccag tggaattcag      540
gccacggtgc tcagccatta catcagccag caagaccacg ctgtaagcgg aagtctataa      600
```

```
caatgctgag gttaatatcg aaaactgact gaccattatg aagactaagg ccacggtggt      660
caaccaaaca ggtggactat gattacgtca actggtatgt agtggggaaa aaacaaccag      720
aattccagtg ggcgtggaca agtattgagg aatataaaga cttgatcctt aatattccca      780
ccacactgaa gcctgatgtc cagttcttca catcgaccta cttgactcct ggagtgagtg      840
actctcaatc ctctcaagtc tccaatactt ctggtgctcc catctatcgt ggtagaaata      900
ccgagagata catggagcac cagtgggcga taatgaacag ggtaccgatg gagtgggtaa      960
ctcgtcggga aattggcatt gccattccca atggaccgtc acccgaataa ttcacacctg     1020
ggtcttgctc acctacaaca accacctctg caaacgagtt caaaacagcg tcaccacagg     1080
cagtgccaac aacaactttg gcttcagcat cccctgaggg tattttgact tcagcagatt     1140
ccactgccac tttggcccc gagactggca aagactcatc aaaacaacta ggaactgtga     1200
cctaaaaacc tgcacttcca actcttcaac attcaagtca aggaggtcac gatgacgatt     1260
ggcaagacga agattgctaa taactttacc agcacgaatc aattctcagc ggactcagac     1320
tatcaactcc catacgtgat cagaagtgcg catgagggtg tctacctccc cttccctcct     1380
gatgcgttta tgttgcctca gtatgggtat tgtactttgg acaatgatgg gaaaagctca     1440
gagaagagtg agttctactg tctagggtat tttcctagtc aaatgttgag aacgggtaac     1500
aactttgaat tttcctatgc ttttgaatct gtccccttc atagaatgtg aatgcataat     1560
cagagcttgg tagattgatg aatccattga ttgatcaata tctatataga tttgataatc     1620
taatcaatgg aaacattgct aatcccacct tcacttacaa aaaggaatca gcaggagata     1680
tggtttctca ggctaggaat tggttaccta gggaccaggg actaatggat ggtcctaaca     1740
atcaagtcag tctagatggt tagaggatca gtcctctaat ggtgttcaat ggaaaatctt     1800
ttactgtatt tcctggacca ttcatgtata ctgcattgcg gatgaactgg aggttcaacc     1860
tagcagcaat ctcctcactt tcgctaaaga tgcctctgta cctgaatcca ccacaactaa     1920
tagtattggt gatcaagatc cgaatagcaa attgttagtc actgatgaga agaaggtcag     1980
gacagtgaat gctactgctg ctaatacctg gggatctgtg acagtgaacc agaagatctc     2040
acctccacta ctgctggaca ggttctaaat caaatgagtg ccatgcctgg aatggtctgc     2100
caaaatagag acacctccat ggtcctattt gggtgaagat tcctcacaca gatcgtcact     2160
tccatccctc tcctctaatg ggtggctttg gtctcaaaca tcttcctcct cagattatga     2220
ttaaaaacac tcctgtccct cctaaccctg ccaccacctt cactcctgtc aaacaaaact     2280
ctttcatcac ttaatactct actggtcaag tgactgtaga aattgaatgg gaactccaga     2340
aagaaacctc ctagaaatgg aatactgaaa tccactttat ttccactttc agaaacacta     2400
ttgacttacc ttttgctccc aacaatgaag atgtgtactc tgaaccttgt ctcattggta     2460
ccggatgcct tacctgtccc atctatctgt gttgtactta ttttatattt gtactttttt     2520
attcaataaa caggtttatt cgtttcattg tacttctctt gtcacgtggt gcttataagc     2580
agacaatgag ctgtggtggg ttggctttca caggaggcgt ggtctcatta aaatcttatg     2640
gagagtgtgg ctactccttt gcttgctcac tca                                  2673
```

<210> SEQ ID NO 21
<211> LENGTH: 581
<212> TYPE: PRT
<213> ORGANISM: Artificial Sequence
<220> FEATURE:
<223> OTHER INFORMATION: mAAV-EVE1 deduced Rep protein

```
<400> SEQUENCE: 21

Met Leu Glu Leu Glu His Val Lys Phe Tyr Glu Ala Ile Phe Leu Val
1               5                   10                  15

Pro Arg Asp Leu Glu Ser Asp Ile Pro Gly Tyr Pro Lys Arg Leu Val
                20                  25                  30

Thr Gln Ile Glu Glu Thr Lys Trp Thr Leu Ser Glu Lys Asp Asp Leu
            35                  40                  45

Asp Leu Glu Ala Val Glu Ser Gly Gln Val Thr Phe Ala His Leu Phe
        50                  55                  60

Ser Arg Lys Phe Leu Lys His Trp Glu Tyr Leu Thr Arg Asn Arg Glu
65                  70                  75                  80

Phe Lys Tyr Tyr Val Gln Leu Glu Lys Gly Glu Ile Tyr Tyr His Leu
                85                  90                  95

His Met Leu Phe Glu Thr Ser Gly Ile Gln Ser Met Val Leu Ser Arg
                100                 105                 110

Tyr Ile Ser Gln Ile Lys Thr Ser Leu Gln Ala Glu Val Ser Asn Asn
            115                 120                 125

Ala Glu Val Asn Ile Glu Asn Trp Leu Ala Ile Thr Lys Thr Lys Ala
        130                 135                 140

Thr Gly Gly Ser Thr Lys Gln Val Asp Tyr Asn Tyr Ile Asn Trp Tyr
145                 150                 155                 160

Leu Val Ala Lys Lys Gln Pro Glu Phe Gln Trp Ala Trp Thr Asn Ile
                165                 170                 175

Glu Glu Tyr Lys Asp Leu Ile Leu Asn Ile Pro Ala Arg Leu Gln Leu
                180                 185                 190

Ala Gly Gln Phe Phe Thr Ser Thr Tyr Leu Ala Pro Gly Val Ser Asp
            195                 200                 205

Ser Gln Ser Ser Gln Ile Ser Asn Thr Ser Gly Ala Pro Phe Tyr Cys
        210                 215                 220

Asp Arg Asn Thr Glu Arg Tyr Met Glu Leu Val Asn Trp Leu Val Glu
225                 230                 235                 240

Gln Leu Thr Ser Glu Lys Gln Trp Ile Ile Glu Asn Gln Glu Ser Tyr
                245                 250                 255

Leu Ser His Gln Ser Thr Ser Asn Gly Ala Arg Gln Ile Lys Val Ala
            260                 265                 270

Leu Asp Asn Ala Ser Lys Ile Met Asn Leu Thr Lys Asn Ala Asp Asp
        275                 280                 285

Tyr Leu Ile Pro Lys Glu Phe Val Ser Phe Asp Asn Ile Lys Gln Asn
        290                 295                 300

His Ile Tyr Trp Ile Phe Lys Asn Gly Tyr Asp Pro Leu Tyr Ala Gly
305                 310                 315                 320

Ser Ile Leu Val Gly Trp Ala Arg Lys Glu Phe Gly Lys Arg Asn Thr
                325                 330                 335

Ile Trp Phe Tyr Gly Lys Ala Thr Thr Gly Asn Thr Asn Ile Ala Glu
            340                 345                 350

Ala Val Ala His Thr Val Pro Leu Tyr Gly Tyr Val Asn Trp Thr Asn
        355                 360                 365

Glu Asn Phe Pro Phe Asn Asp Cys Val Asp Lys Met Leu Ile Trp Trp
370                 375                 380

Glu Glu Gly Glu Ile Thr Ser Lys Val Val Glu Thr Ala Lys Ala Ile
385                 390                 395                 400

Leu Gly Gly Ala Lys Val Gln Val Asp Gln Glu Cys Lys Ser Ser Val
                405                 410                 415
```

```
Gln Ile Asp Cys Thr Pro Val Ile Thr Ser Asn Thr Asn Met Cys
        420                 425                 430
Tyr Met Val Asp Gly Asn Thr Met Ile Phe Glu His Lys Gln Leu Leu
                435                 440                 445
Gln Asp His Met Phe Gln Phe Met Leu Met Glu Arg Leu Pro Asp Asp
    450                 455                 460
Phe Gly Lys Val Thr Lys Glu Glu Val Arg Gln Phe Lys Trp Ala
465                 470                 475                 480
Ala Val Asn Gln Ile Pro Pro Lys Gln Glu Phe Thr Val Lys Ile
                485                 490                 495
Met Ser Ser Ile Asp Cys Tyr Tyr Asp His Lys Gln Lys Trp Glu Glu
                500                 505                 510
Tyr Pro Ser Thr Phe Cys Gln Gly Gly Tyr Lys Lys Ala Glu Pro Pro
        515                 520                 525
Ser Lys Lys Phe Phe Pro Phe Arg Asp Leu Lys Lys Ile Glu Val Ile
        530                 535                 540
Glu Gln Arg Ala Pro Thr Val Glu Ser Asp Phe Glu Asn Leu Lys Arg
545                 550                 555                 560
Phe Gly Leu Asn Val Ile Pro Ala Ser Asp Pro Ile Ala Leu Asp Asp
                565                 570                 575
Cys Gln Asp Glu Gln
            580

<210> SEQ ID NO 22
<211> LENGTH: 1746
<212> TYPE: DNA
<213> ORGANISM: Artificial Sequence
<220> FEATURE:
<223> OTHER INFORMATION: mAAV-EVE1 deduced rep gene

<400> SEQUENCE: 22
atgctggagc tggaacacgt gaagttttat gaggcaattt ccttgtgcc cagagacttg      60
gagtctgaca tccctggcta tcctaagaga ctggtcactc agatagaaga gaccaagtgg     120
acactttcag aaaaggacga cctggacttg aagcgtgtgg agagtggaca ggtaacattt     180
gcccatctat tctcccgcaa attccttaag cactgggagt acctgacaag aaatcgagaa     240
ttcaaatact atgtccagct ggaaaagggt gagatctatt accatttaca tatgcttttt     300
gagaccagtg gaattcagtc catggtgctc agccgttaca tcagccagat caagacctcg     360
ctgcaagctg aagtctctaa caatgctgag gttaatatcg aaaactggct ggccattacg     420
aagactaagg ccaccggggg gtcaaccaaa caggtggact ataattacat caactggtat     480
ttagtggcaa aaaacaacc agaatttcag tgggcgtgga caaatattga ggaatataag     540
gacttgatcc tcaatatccc cgccagactg cagctcgcag ccagttcttc acatcgacc    600
tacttggctc ctgggggtgag tgactcccaa tcctctcaaa tctctaatac ttctggtgct    660
cccttctatt gtgatagaaa taccgagaga tacatggagc ttgtaaattg cttgtggag     720
cagcttacct ctgaaaagca gtggattatt gaaaatcagg aaagttatct ctctcaccaa    780
tccactagca atggagccag gcagattaaa gtcgctctgg acaatgcttc taaaattatg    840
aatctgacca aaaatgcaga tgattacctt atcccgaaag aatttgtcag ttttgacaac    900
attaaacaga accatatcta ttggatcttt aagaatggat acgaccctct ttatgctgga    960
tctatcctgg tgggctgggc cagaaaagaa tttggcaaaa gaacaccat ctggttctat   1020
ggaaaggcca ctactgggaa cactaacatt gcggaagccg ttgcacacac ggtgcccta   1080
```

```
tacgggtatg tgaattggac taatgagaac tttccattca atgactgtgt ggataaaatg    1140
ctcatctggt gggaggaagg cgagattacc tctaaggtgg ttgagacagc taaagccatc    1200
cttggaggag ctaaagttca ggtggaccag gaatgtaagt cctctgttca aattgattgt    1260
actccagtca tcatcacctc caacaccaac atgtgctaca tggtggacgg aacactatg    1320 atctttgaac acaagcagtt gttacaagac cacatgtttc aattcatgct catggagaga    1380
cttcctgatg actttggcaa ggtgacaaag gaggaggtgc gtcagttttt taatgggca    1440 gctgttaatc aaattccccc taagcaggaa ttcactgtca agaagattat gtcatccatt    1500
gactgttact atgaccacaa gcagaaatgg gaggagtatc cctcgacttt ctgtcaaggg    1560
ggctataaaa aggccgagcc tccctcgaaa aagttctttc cattccggga tttgaagaaa    1620
attgaggtca tcgagcagag agcccccaca gtggaatcgg actttgagaa tctcaaaagg    1680
tttggtctca atgtaattcc cgcttctgat cctattgctt tggatgactg tcaggatgag    1740
caataa                                                               1746

<210> SEQ ID NO 23
<211> LENGTH: 44
<212> TYPE: DNA
<213> ORGANISM: Artificial Sequence
<220> FEATURE:
<223> OTHER INFORMATION: AA55 primer

<400> SEQUENCE: 23
gtgcccttct acggctgcgt caactggacc aatgagaact ttcc               44

<210> SEQ ID NO 24
<211> LENGTH: 26
<212> TYPE: DNA
<213> ORGANISM: Artificial Sequence
<220> FEATURE:
<223> OTHER INFORMATION: SIG primer

<400> SEQUENCE: 24
gaatccccag ttgttgttga tgagtc                                   26

<210> SEQ ID NO 25
<211> LENGTH: 56
<212> TYPE: DNA
<213> ORGANISM: Artificial Sequence
<220> FEATURE:
<223> OTHER INFORMATION: AAV-EVE_flank_up primer

<400> SEQUENCE: 25
gatgtttaca gattagtrtt kyatcatcag tgctatttyc ycwcaawrar ratycc    56

<210> SEQ ID NO 26
<211> LENGTH: 36
<212> TYPE: DNA
<213> ORGANISM: Artificial Sequence
<220> FEATURE:
<223> OTHER INFORMATION: AAV-EVE_flank_down primer

<400> SEQUENCE: 26
agggagagta cctattatct taattactgt cagacc                        36

<210> SEQ ID NO 27
<211> LENGTH: 30
<212> TYPE: DNA
<213> ORGANISM: Artificial Sequence
<220> FEATURE:
```

<223> OTHER INFORMATION: Macr(-335)flank_up primer

<400> SEQUENCE: 27
cctggaattt gtgggtggaa acaatgatcc					30

<210> SEQ ID NO 28
<211> LENGTH: 201
<212> TYPE: PRT
<213> ORGANISM: Artificial Sequence
<220> FEATURE:
<223> OTHER INFORMATION: mAAV-EVE1 deduced AAP protein

<400> SEQUENCE: 28

Leu Arg Ser Cys Ala Ser Leu Ser Asn Ser Lys Ser Leu Leu Leu His
1               5                   10                  15

Leu Ser Asp Lys Arg Arg Glu Asp Ser Leu Ser Thr Gln Thr Ala Thr
            20                  25                  30

Met Glu His Thr Pro Ala Val Ser Asn Gln Pro Pro Leu Ile Trp Asp
        35                  40                  45

Leu Val Ser Trp Gln Lys Glu Val Ala His Gln Trp Ala Ile Ile Asn
    50                  55                  60

Arg Val Leu Met Glu Trp Val Ile Pro Gln Ile Gly Ile Val Ile
65                  70                  75                  80

Pro Asn Gly Trp Ala Thr Glu Ser Pro Pro Glu Lys Leu Thr Pro Gly
                85                  90                  95

Ser Cys Pro Pro Thr Thr Thr Ser Thr Ser Glu Phe Lys Thr Val
            100                 105                 110

Ser Pro Gln Ala Val Pro Thr Thr Leu Ala Ser Ala Pro Pro Gly
        115                 120                 125

Gly Ile Leu Thr Ser Thr Asp Ser Thr Ala Thr Ser Ala Pro Glu Thr
    130                 135                 140

Gly Lys Asp Leu Ser Ile Thr Thr Gly Asp Cys Asp Leu Lys Thr Cys
145                 150                 155                 160

Thr Ser Asn Ser Ser Thr Ser Lys Ser Arg Arg Ser Gln Gly Gly Met
                165                 170                 175

Leu Arg Pro Gln Leu Leu Ile Thr Leu Pro Ala Arg Phe Lys Ser Leu
            180                 185                 190

Arg Thr Gln Ser Ile Asn Ser His Thr
        195                 200

<210> SEQ ID NO 29
<211> LENGTH: 606
<212> TYPE: DNA
<213> ORGANISM: Artificial Sequence
<220> FEATURE:
<223> OTHER INFORMATION: mAAV-EVE1 deduced aap gene

<400> SEQUENCE: 29
ctgagaagct gcgcatccct cagcaactcc aaatccctcc tcctccatct aagcgacaaa      60
agacgagagg actcccttc aacccaaaca gcgacaatgg agcatacacc agcagtcagc      120
aatcagcccc cactaatttg ggatctggta tcatggcaga aggaggtggc gcaccaatgg      180
gcaataatca acagggtgct gatggagtgg gtaattcctc aggaaattgg cattgtgatt      240
cccaatggat gggccacaga gtcgccaccc gaaaaactca cacctgggtc ttgcccacct      300
acaacaacca cctctacaag cgagttcaaa acagtgtcac cacaggcagt gccaacaact      360
actttggctt cagcaccccc tgggggtatt ttgacttcaa cagattccac tgccacttca      420

```
gcccccgaga ctggcaaaga cttatcaata caaactgggg actgcgacct aaaaacctgc    480
acttcaaact cttcaacatc caagtcaagg aggtcacaag gaggaatgtt gagaccacaa    540
ttgctaataa ccttaccagc acgattcaag tctttgcgga ctcagagtat caactcccat    600
acgtga                                                                606
```

```
<210> SEQ ID NO 30
<211> LENGTH: 731
<212> TYPE: PRT
<213> ORGANISM: Artificial Sequence
<220> FEATURE:
<223> OTHER INFORMATION: mAAV-EVE1 deduced modified capsid protein

<400> SEQUENCE: 30
```

| Met | Ser | Phe | Leu | Glu | Lys | Phe | Glu | Asp | Trp | Tyr | Glu | Lys | Ser | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Trp | Arg | His | Leu | Glu | Ala | Gly | Pro | Pro | His | Pro | Lys | Ala | Asn | Gln |
|     |     |     | 20  |     |     |     |     | 25  |     |     |     |     | 30  |     |     |

| Gln | His | Gln | Asp | Asp | Ser | His | Gly | Leu | Val | Leu | Pro | Gly | Tyr | Lys | Tyr |
|     |     |     | 35  |     |     |     |     | 40  |     |     |     |     | 45  |     |     |

| Leu | Ile | Pro | Phe | Asn | Gly | Leu | Asp | Lys | Gly | Glu | Pro | Val | Asn | Gln | Ala |
|     | 50  |     |     |     |     | 55  |     |     |     |     | 60  |     |     |     |     |

| Asp | Glu | Ala | Ala | Leu | Glu | His | Asp | Lys | Ala | Tyr | Asp | Gln | Leu | Leu | Lys |
| 65  |     |     |     |     | 70  |     |     |     |     | 75  |     |     |     |     | 80  |

| Glu | Gly | Asp | Asn | Pro | Tyr | Leu | Thr | Tyr | Asn | His | Ala | Asp | Gln | Glu | Phe |
|     |     |     |     | 85  |     |     |     |     | 90  |     |     |     |     | 95  |     |

| Gln | Glu | Lys | Leu | Ser | Glu | Asp | Thr | Ser | Phe | Gly | Gly | Asn | Leu | Gly | Lys |
|     |     |     | 100 |     |     |     |     | 105 |     |     |     |     | 110 |     |     |

| Ala | Val | Phe | Gln | Gly | Lys | Lys | Arg | Leu | Leu | Glu | Pro | Leu | Gly | Leu | Val |
|     |     |     | 115 |     |     |     |     | 120 |     |     |     |     | 125 |     |     |

| Glu | Pro | Asp | Leu | Ala | Pro | Val | Lys | Gly | Glu | Thr | Pro | Glu | Lys | Leu | Arg |
| 130 |     |     |     |     | 135 |     |     |     |     | 140 |     |     |     |     |     |

| Ile | Pro | Gln | Gln | Leu | Gln | Ile | Pro | Pro | Pro | Ser | Lys | Arg | Gln | Lys |
| 145 |     |     |     |     | 150 |     |     |     |     | 155 |     |     |     |     | 160 |

| Thr | Arg | Gly | Leu | Pro | Phe | Asn | Pro | Asn | Ser | Asp | Asn | Gly | Ala | Tyr | Thr |
|     |     |     |     | 165 |     |     |     |     | 170 |     |     |     |     | 175 |     |

| Ser | Ser | Gln | Gln | Ser | Ala | Pro | Thr | Asn | Leu | Gly | Ser | Gly | Ile | Met | Ala |
|     |     |     |     | 180 |     |     |     |     | 185 |     |     |     |     | 190 |     |

| Glu | Gly | Gly | Gly | Ala | Pro | Met | Gly | Asp | Asn | Gln | Gln | Gly | Ala | Asp | Gly |
|     |     |     | 195 |     |     |     |     | 200 |     |     |     |     | 205 |     |     |

| Val | Gly | Asn | Ser | Ser | Gly | Asn | Trp | His | Cys | Asp | Ser | Gln | Trp | Met | Gly |
|     | 210 |     |     |     |     | 215 |     |     |     |     | 220 |     |     |     |     |

| Asn | Arg | Val | Val | Thr | Arg | Thr | Thr | Arg | Thr | Trp | Val | Leu | Pro | Thr | Tyr |
| 225 |     |     |     |     | 230 |     |     |     |     | 235 |     |     |     |     | 240 |

| Asn | Asn | His | Leu | Tyr | Lys | Arg | Ile | Gln | Asn | Ser | Val | Thr | Thr | Gly | Ser |
|     |     |     |     | 245 |     |     |     |     | 250 |     |     |     |     | 255 |     |

| Ala | Asn | Asn | Tyr | Phe | Gly | Phe | Ser | Thr | Pro | Trp | Gly | Tyr | Phe | Asp | Phe |
|     |     |     | 260 |     |     |     |     | 265 |     |     |     |     | 270 |     |     |

| Asn | Arg | Phe | His | Cys | His | Phe | Ser | Pro | Arg | Asp | Trp | Gln | Arg | Leu | Ile |
|     |     |     | 275 |     |     |     |     | 280 |     |     |     |     | 285 |     |     |

| Asn | Asn | Asn | Trp | Gly | Leu | Arg | Pro | Lys | Ser | Leu | Arg | Phe | Lys | Leu | Phe |
|     |     |     | 290 |     |     |     |     | 295 |     |     |     |     | 300 |     |     |

| Asn | Ile | Gln | Val | Lys | Glu | Val | Thr | Thr | Thr | Asn | Gly | Glu | Thr | Thr | Ile |
| 305 |     |     |     |     | 310 |     |     |     |     | 315 |     |     |     |     | 320 |

| Ala | Asn | Asn | Leu | Thr | Ser | Thr | Ile | Gln | Val | Phe | Ala | Asp | Ser | Glu | Tyr |

325                 330                 335
Gln Leu Pro Tyr Val Ile Gly Ser Ala Gln Glu Gly Cys Leu Pro Pro
                340                 345                 350

Phe Pro Pro Asp Val Phe Met Leu Pro Gln Tyr Gly Tyr Cys Thr Leu
            355                 360                 365

Asp Asn Asp Gly Lys Ser Leu Glu Arg Ser Ala Phe Tyr Cys Leu Glu
        370                 375                 380

Tyr Phe Pro Ser Gln Met Leu Arg Thr Gly Asn Asn Phe Glu Phe Ser
385                 390                 395                 400

Tyr Ala Phe Glu Ser Val Pro Phe His Ser Met Trp Met His Asn Gln
                405                 410                 415

Ser Leu Asp Arg Leu Met Asn Pro Leu Ile Asp Gln Tyr Leu Tyr Arg
            420                 425                 430

Phe Asp Asn Leu Thr Ser Gly Asn Thr Val Asn Pro Thr Phe Thr Tyr
        435                 440                 445

Lys Lys Gly Ser Ala Gly Asp Met Ala Ser Gln Ala Arg Asn Trp Leu
450                 455                 460

Pro Gly Pro Met Leu Arg Asn Gln Gly Leu Met Asp Gly Pro Asn Asn
465                 470                 475                 480

Gln Ala Asn Leu Asp Gly Trp Arg Ile Ser Pro Pro Met Val Ile Asn
                485                 490                 495

Gly Lys Ser Ser Ile Ile Phe Pro Gly Pro Ser Met Tyr Thr Ala His
            500                 505                 510

Asn Ala Ala Asp Glu Leu Glu Val Gln Pro Ser Ile Asn Leu Pro Ile
        515                 520                 525

Phe Ala Lys Asp Ala Ser Val Pro Glu Ser Thr Ile Ile Ser Ser Ile
530                 535                 540

Gly Asn Gln Asp Pro Asn Ser Lys Leu Leu Val Thr Asp Glu Asn Glu
545                 550                 555                 560

Val Gly Thr Val Asn Ala Thr Ala Ala Asn Thr Trp Gly Ser Met Ala
                565                 570                 575

Val Asn Gln Gln Thr Pro Thr Pro Thr Ser Ala Gly Gln Val Leu Asn
            580                 585                 590

Gln Met Gly Val Met Pro Gly Met Val Trp Gln Asn Arg Asp Ile Tyr
        595                 600                 605

Leu Gln Gly Pro Ile Trp Ala Lys Ile Pro His Thr Asp Gly His Phe
610                 615                 620

His Pro Ser Pro Leu Met Gly Gly Phe Gly Leu Lys His Pro Pro Pro
625                 630                 635                 640

Gln Ile Met Ile Lys Asn Thr Pro Val Pro Ala Asn Pro Ala Thr Ile
                645                 650                 655

Phe Thr Pro Val Lys Gln Asn Ser Phe Ile Thr Gln Tyr Ser Thr Gly
            660                 665                 670

Gln Val Thr Val Glu Ile Glu Trp Glu Leu Gln Lys Glu Thr Ser Lys
        675                 680                 685

Lys Trp Asn Pro Glu Ile Gln Phe Thr Ser Asn Phe Arg Asn Thr Ile
690                 695                 700

Asp Leu Pro Phe Ala Pro Asn Asn Glu Gly Val Tyr Ser Glu Pro Arg
705                 710                 715                 720

Pro Ile Gly Thr Arg Tyr Leu Thr Arg Pro Ile
                725                 730

<210> SEQ ID NO 31

```
<211> LENGTH: 541
<212> TYPE: PRT
<213> ORGANISM: Artificial Sequence
<220> FEATURE:
<223> OTHER INFORMATION: mAAV-EVE1 deduced modified VP3 protein

<400> SEQUENCE: 31
```

Met Ala Glu Gly Gly Ala Pro Met Gly Asp Asn Gln Gln Gly Ala
1               5                   10                  15

Asp Gly Val Gly Asn Ser Ser Gly Asn Trp His Cys Asp Ser Gln Trp
            20                  25                  30

Met Gly Asn Arg Val Val Thr Arg Thr Thr Arg Thr Trp Val Leu Pro
        35                  40                  45

Thr Tyr Asn Asn His Leu Tyr Lys Arg Ile Gln Asn Ser Val Thr Thr
    50                  55                  60

Gly Ser Ala Asn Asn Tyr Phe Gly Phe Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Leu Arg Pro Lys Ser Leu Arg Phe Lys
            100                 105                 110

Leu Phe Asn Ile Gln Val Lys Glu Val Thr Thr Thr Asn Gly Glu Thr
        115                 120                 125

Thr Ile Ala Asn Asn Leu Thr Ser Thr Ile Gln Val Phe Ala Asp Ser
    130                 135                 140

Glu Tyr Gln Leu Pro Tyr Val Ile Gly Ser Ala Gln Glu Gly Cys Leu
145                 150                 155                 160

Pro Pro Phe Pro Pro Asp Val Phe Met Leu Pro Gln Tyr Gly Tyr Cys
                165                 170                 175

Thr Leu Asp Asn Asp Gly Lys Ser Leu Glu Arg Ser Ala Phe Tyr Cys
            180                 185                 190

Leu Glu Tyr Phe Pro Ser Gln Met Leu Arg Thr Gly Asn Asn Phe Glu
        195                 200                 205

Phe Ser Tyr Ala Phe Glu Ser Val Pro Phe His Ser Met Trp Met His
    210                 215                 220

Asn Gln Ser Leu Asp Arg Leu Met Asn Pro Leu Ile Asp Gln Tyr Leu
225                 230                 235                 240

Tyr Arg Phe Asp Asn Leu Thr Ser Gly Asn Thr Val Asn Pro Thr Phe
                245                 250                 255

Thr Tyr Lys Lys Gly Ser Ala Gly Asp Met Ala Ser Gln Ala Arg Asn
            260                 265                 270

Trp Leu Pro Gly Pro Met Leu Arg Asn Gln Gly Leu Met Asp Gly Pro
        275                 280                 285

Asn Asn Gln Ala Asn Leu Asp Gly Trp Arg Ile Ser Pro Pro Met Val
    290                 295                 300

Ile Asn Gly Lys Ser Ser Ile Ile Phe Pro Gly Pro Ser Met Tyr Thr
305                 310                 315                 320

Ala His Asn Ala Ala Asp Glu Leu Glu Val Gln Pro Ser Ile Asn Leu
                325                 330                 335

Pro Ile Phe Ala Lys Asp Ala Ser Val Pro Glu Ser Thr Ile Ile Ser
            340                 345                 350

Ser Ile Gly Asn Gln Asp Pro Asn Ser Lys Leu Leu Val Thr Asp Glu
        355                 360                 365

Asn Glu Val Gly Thr Val Asn Ala Thr Ala Ala Asn Thr Trp Gly Ser
    370                 375                 380

```
Met Ala Val Asn Gln Gln Thr Pro Thr Pro Thr Ser Ala Gly Gln Val
385                 390                 395                 400

Leu Asn Gln Met Gly Val Met Pro Gly Met Val Trp Gln Asn Arg Asp
            405                 410                 415

Ile Tyr Leu Gln Gly Pro Ile Trp Ala Lys Ile Pro His Thr Asp Gly
        420                 425                 430

His Phe His Pro Ser Pro Leu Met Gly Gly Phe Gly Leu Lys His Pro
    435                 440                 445

Pro Pro Gln Ile Met Ile Lys Asn Thr Pro Val Pro Ala Asn Pro Ala
450                 455                 460

Thr Ile Phe Thr Pro Val Lys Gln Asn Ser Phe Ile Thr Gln Tyr Ser
465                 470                 475                 480

Thr Gly Gln Val Thr Val Glu Ile Glu Trp Glu Leu Gln Lys Glu Thr
                485                 490                 495

Ser Lys Lys Trp Asn Pro Glu Ile Gln Phe Thr Ser Asn Phe Arg Asn
            500                 505                 510

Thr Ile Asp Leu Pro Phe Ala Pro Asn Asn Glu Gly Val Tyr Ser Glu
        515                 520                 525

Pro Arg Pro Ile Gly Thr Arg Tyr Leu Thr Arg Pro Ile
    530                 535                 540

<210> SEQ ID NO 32
<211> LENGTH: 2196
<212> TYPE: DNA
<213> ORGANISM: Artificial Sequence
<220> FEATURE:
<223> OTHER INFORMATION: mAAV-EVE1 deduced modified cap gene

<400> SEQUENCE: 32
atgtcttttt tggagaaatt tgaggactgg tacgaaaagt cagctgctac ttggagacac      60
cttgaagctg cccacctca tcctaaagct aatcaacaac atcaagatga ctctcatgga     120
ctggttctgc caggctataa gtatctcatt ccctttaatg gtctcgataa gggggagcca     180
gttaatcaag cagacgaagc cgcactggaa catgacaaag cctacgatca attactcaaa     240 gaagggata atccttacct cacctacaac cacgcagacc aagagttcca ggaaaaactt     300
tcggaggaca cttcgtttgg tggtaacctt ggcaaggcag tgtttcaagg aaagaaacga     360
ctgcttgagc cattaggatt agtagaacca gacctggcgc ctgtgaaagg agaaactcct     420
gagaagctgc gcatccctca gcaactccaa atccctcctc ctccatctaa gcgacaaaag     480
acgagaggac ttcccttcaa cccaaacagc gacaatggag catacaccag cagtcagcaa     540
tcagccccca ctaatttggg atctggtatc atggcagaag aggtggcgc accaatgggc     600 gataatcaac agggtgctga tggagtgggt aattcctcag gaaattggca ttgtgattcc     660
caatggatgg gcaacagagt cgtcacccga caactcgca cctgggtctt gcccacctac     720
aacaaccacc tctacaagcg aattcaaaac agtgtcacca caggcagtgc aacaactac     780 tttggcttca gcaccccctg ggggtatttt gacttcaaca gattccactg ccacttcagc     840
ccccgagact ggcaaagact tatcaataac aactggggac tgcgacctaa aagcctgcgc     900
ttcaaactct tcaacatcca gtcaaggag gtcacaacga cgaatggcga gaccacaatt     960
gctaataacc ttaccagcac gattcaagtc tttgcggact cagagtatca actcccatac    1020
gtgatcggga gtgctcaaga ggggtgtcta ccccccttcc ctcctgatgt gtttatgttg    1080
cctcagtatg ggtattgtac tttggacaat gatgggaaaa gtttagagag gagtgcattc    1140
```

```
tactgtctag aatattttcc tagccaaatg ttgagaacgg gtaacaactt tgaattttcc    1200
tatgcttttg aatctgtccc ctttcatagc atgtggatgc acaatcagag cttggataga    1260
ttgatgaatc cattgattga tcaatatctg tatagatttg ataatctaac cagtggaaac    1320
actgttaatc ccaccttcac ttacaaaaag ggatcagcag gtgatatggc ttctcaggct    1380
aggaattggt tacctggtcc tatgcttagg aatcagggac taatggatgg tcctaacaat    1440
caggccaatc tagatggttg gaggatcagt cctccaatgg tgatcaatgg aaaatcttct    1500
attatatttc ctgggccatc catgtatacc gcacacaatg ctgcagatga actggaggtt    1560
caacctagca ttaatctccc tatctttgct aaagatgcct ctgtacctga atccaccata    1620
attagtagta ttggtaatca agatcctaat agtaaattgt tagtcactga tgagaacgag    1680
gtcgggacag tgaatgctac tgctgctaat acctgggggt ctatggcagt caaccagcag    1740
actcccaccc ccactagtgc aggacaggtt ctaaatcaaa tgggtgtcat gcctggaatg    1800
gtctggcaga atagagacat ctatctccaa ggtcccattt gggctaagat tcctcacaca    1860
gatggtcact ccatccctc tcctctcatg ggtggctttg gtctcaaaca tcctcctcct    1920
cagattatga ttaaaaacac tcctgtcccc gctaaccctg ccaccatctt cactcctgtc    1980
aaacaaaatt ctttcatcac tcaatactct actggtcaag tgactgtaga aattgaatgg    2040
gaactccaga aggaaacctc caagaaatgg aatcctgaaa tccagtttac ttccaatttc    2100
agaaacacta ttgacttacc ttttgctccc aacaatgaag gtgtatactc tgaacctcgt    2160
cccattggta cccgatacct tacccgtccc atctaa                              2196
```

<210> SEQ ID NO 33
<211> LENGTH: 1626
<212> TYPE: DNA
<213> ORGANISM: Artificial Sequence
<220> FEATURE:
<223> OTHER INFORMATION: mAAV-EVE1 deduced modified VP3 coding sequence

<400> SEQUENCE: 33

```
atggcagaag gaggtggcgc accaatgggc gataatcaac agggtgctga tggagtgggt     60
aattcctcag gaaattggca ttgtgattcc caatggatgg gcaacagagt cgtcacccga    120
acaactcgca cctgggtctt gcccacctac aacaaccacc tctacaagcg aattcaaaac    180
agtgtcacca caggcagtgc caacaactac tttggcttca gcaccccctg ggggtatttt    240
gacttcaaca gattccactg ccacttcagc ccccgagact ggcaaagact tatcaataac    300
aactggggac tgcgacctaa agcctgcgcc ttcaaactct tcaacatcca agtcaaggag    360
gtcacaacga cgaatggcga gaccacaatt gctaataacc ttaccagcac gattcaagtc    420
tttgcggact cagagtatca actcccatac gtgatcggga gtgctcaaga ggggtgtcta    480
ccccccttcc ctcctgatgt gtttatgttg cctcagtatg gtattgtac tttggacaat    540 gatgggaaaa gtttagagag gagtgcattc tactgtctag aatattttcc tagccaaatg    600
ttgagaacgg gtaacaactt tgaattttcc tatgcttttg aatctgtccc ctttcatagc    660
atgtggatgc acaatcagag cttggataga ttgatgaatc cattgattga tcaatatctg    720
tatagatttg ataatctaac cagtggaaac actgttaatc ccaccttcac ttacaaaaag    780
ggatcagcag gtgatatggc ttctcaggct aggaattggt tacctggtcc tatgcttagg    840
aatcagggac taatggatgg tcctaacaat caggccaatc tagatggttg gaggatcagt    900
cctccaatgg tgatcaatgg aaaatcttct attatatttc ctgggccatc catgtatacc    960
gcacacaatg ctgcagatga actggaggtt caacctagca ttaatctccc tatctttgct   1020
```

```
aaagatgcct ctgtacctga atccaccata attagtagta ttggtaatca agatcctaat   1080
agtaaattgt tagtcactga tgagaacgag gtcgggacag tgaatgctac tgctgctaat   1140 acctggggt ctatggcagt caaccagcag actcccaccc ccactagtgc aggacaggtt    1200
ctaaatcaaa tgggtgtcat gcctggaatg gtctggcaga atagagacat ctatctccaa   1260
ggtcccattt gggctaagat tcctcacaca gatggtcact tccatccctc tcctctcatg   1320
ggtggctttg gtctcaaaca tcctcctcct cagattatga ttaaaaacac tcctgtccct   1380
gctaaccctg ccaccatctt cactcctgtc aaacaaaatt ctttcatcac tcaatactct   1440
actggtcaag tgactgtaga aattgaatgg gaactccaga aggaaacctc caagaaatgg   1500
aatcctgaaa tccagtttac ttccaatttc agaaacacta ttgacttacc ttttgctccc   1560
aacaatgaag gtgtatactc tgaacctcgt cccattggta cccgatacct tacccgtccc   1620
atctaa                                                              1626
```

<210> SEQ ID NO 34
<211> LENGTH: 600
<212> TYPE: PRT
<213> ORGANISM: Artificial Sequence
<220> FEATURE:
<223> OTHER INFORMATION: mAAV-EVE1 deduced VP2 protein

<400> SEQUENCE: 34

```
Leu Glu Pro Val Lys Gly Glu Thr Pro Glu Lys Leu Arg Ile Pro Gln
1               5                   10                  15

Gln Leu Gln Ile Pro Pro Pro Ser Lys Arg Gln Lys Thr Arg Gly
        20                  25                  30

Leu Pro Phe Asn Pro Asn Ser Asp Asn Gly Ala Tyr Thr Ser Ser Gln
        35                  40                  45

Gln Ser Ala Pro Thr Asn Leu Gly Ser Gly Ile Met Ala Glu Gly Gly
    50                  55                  60

Gly Ala Pro Met Gly Asn Asn Gln Gln Gly Ala Asp Gly Val Gly Asn
65                  70                  75                  80

Ser Ser Gly Asn Trp His Cys Asp Ser Gln Trp Met Gly His Arg Val
                85                  90                  95

Ala Thr Arg Lys Thr His Thr Trp Val Leu Pro Thr Tyr Asn Asn His
            100                 105                 110

Leu Tyr Lys Arg Val Gln Asn Ser Val Thr Thr Gly Ser Ala Asn Asn
        115                 120                 125

Tyr Phe Gly Phe Ser Thr Pro Trp Gly Tyr Phe Asp Phe Asn Arg Phe
    130                 135                 140

His Cys His Phe Ser Pro Arg Asp Trp Gln Arg Leu Ile Asn Asn Asn
145                 150                 155                 160

Trp Gly Leu Arg Pro Lys Asn Leu His Phe Lys Leu Phe Asn Ile Gln
                165                 170                 175

Val Lys Glu Val Thr Arg Arg Asn Val Glu Thr Thr Ile Ala Asn Asn
            180                 185                 190

Leu Thr Ser Thr Ile Gln Val Phe Ala Asp Ser Glu Tyr Gln Leu Pro
        195                 200                 205

Tyr Val Ile Arg Ser Ala Gln Glu Gly Cys Leu Pro Phe Pro Pro
    210                 215                 220

Asp Val Phe Met Leu Pro Gln Tyr Gly Tyr Cys Thr Leu Asp Asn Asp
225                 230                 235                 240

Gly Lys Ser Leu Glu Arg Ser Ala Phe Tyr Cys Leu Glu Tyr Phe Pro
```

```
                    245                 250                 255
        Ser Gln Met Leu Arg Thr Gly Asn Asn Phe Glu Phe Ser Tyr Ala Phe
                    260                 265                 270

Glu Ser Val Pro Phe His Ser Met Trp Met His Asn Gln Ser Leu Asp
                    275                 280                 285

Arg Leu Met Asn Pro Leu Ile Asp Gln Tyr Leu Tyr Arg Phe Asp Asn
                    290                 295                 300

Leu Thr Ser Gly Asn Thr Val Asn Pro Thr Phe Thr Tyr Lys Lys Gly
        305                 310                 315                 320

Ser Ala Gly Asp Met Ala Ser Gln Ala Arg Asn Trp Leu Pro Gly Pro
                    325                 330                 335

Met Leu Arg Asn Gln Gly Leu Met Asp Gly Pro Asn Asn Gln Ala Asn
                    340                 345                 350

Leu Asp Gly Trp Arg Ile Ser Pro Pro Met Val Ile Asn Gly Lys Ser
                    355                 360                 365

Ser Ile Ile Phe Pro Gly Pro Ser Met Tyr Thr Ala His Asn Ala Ala
                    370                 375                 380

Asp Glu Leu Glu Val Gln Pro Ser Ile Asn Leu Pro Ile Phe Ala Lys
        385                 390                 395                 400

Asp Ala Ser Val Pro Glu Ser Thr Ile Ile Ser Ile Gly Asn Gln
                    405                 410                 415

Asp Pro Asn Ser Lys Leu Leu Val Thr Asp Glu Asn Glu Val Gly Thr
                    420                 425                 430

Val Asn Ala Thr Ala Ala Asn Thr Trp Gly Ser Met Ala Val Asn Gln
                    435                 440                 445

Gln Thr Pro Thr Pro Thr Ser Ala Gly Gln Val Leu Asn Gln Met Ser
                    450                 455                 460

Val Met Pro Gly Met Val Trp Gln Asn Arg Asp Ile Asp Leu His Gly
        465                 470                 475                 480

Pro Ile Trp Ala Lys Ile Pro His Thr Asp Gly Tyr Phe His Pro Ser
                    485                 490                 495

Pro Leu Met Gly Gly Phe Gly Leu Lys His Pro Pro Gln Ile Met
                    500                 505                 510

Ile Lys Asn Thr Pro Val Pro Ala Asn Pro Ala Thr Ile Phe Thr Pro
                    515                 520                 525

Val Lys Gln Asn Ser Phe Ile Thr Gln Tyr Ser Thr Gly Gln Val Thr
                    530                 535                 540

Val Glu Ile Glu Trp Glu Leu Gln Lys Glu Thr Ser Lys Lys Trp Asn
        545                 550                 555                 560

Pro Glu Ile Gln Phe Thr Ser Asn Phe Arg Asn Thr Ile Asp Leu Pro
                    565                 570                 575

Phe Ala Pro Asn Asn Glu Gly Val Tyr Ser Gly Pro Arg Pro Ile Gly
                    580                 585                 590

Thr Arg Tyr Leu Thr Arg Pro Ile
                    595                 600

<210> SEQ ID NO 35
<211> LENGTH: 600
<212> TYPE: PRT
<213> ORGANISM: Artificial Sequence
<220> FEATURE:
<223> OTHER INFORMATION: mAAV-EVE1 deduced, modified VP2 protein

<400> SEQUENCE: 35

Leu Ala Pro Val Lys Gly Glu Thr Pro Glu Lys Leu Arg Ile Pro Gln
```

-continued

```
1               5                   10                  15
Gln Leu Gln Ile Pro Pro Pro Ser Lys Arg Gln Lys Thr Arg Gly
                20                  25                  30
Leu Pro Phe Asn Pro Asn Ser Asp Asn Gly Ala Tyr Thr Ser Ser Gln
                35                  40                  45
Gln Ser Ala Pro Thr Asn Leu Gly Ser Gly Ile Met Ala Glu Gly Gly
                50                  55                  60
Gly Ala Pro Met Gly Asp Asn Gln Gln Gly Ala Asp Gly Val Gly Asn
65                  70                  75                  80
Ser Ser Gly Asn Trp His Cys Asp Ser Gln Trp Met Gly Asn Arg Val
                85                  90                  95
Val Thr Arg Thr Thr Arg Thr Trp Val Leu Pro Thr Tyr Asn Asn His
                100                 105                 110
Leu Tyr Lys Arg Ile Gln Asn Ser Val Thr Thr Gly Ser Ala Asn Asn
                115                 120                 125
Tyr Phe Gly Phe Ser Thr Pro Trp Gly Tyr Phe Asp Phe Asn Arg Phe
                130                 135                 140
His Cys His Phe Ser Pro Arg Asp Trp Gln Arg Leu Ile Asn Asn Asn
145                 150                 155                 160
Trp Gly Leu Arg Pro Lys Ser Leu Arg Phe Lys Leu Phe Asn Ile Gln
                165                 170                 175
Val Lys Glu Val Thr Thr Thr Asn Gly Glu Thr Thr Ile Ala Asn Asn
                180                 185                 190
Leu Thr Ser Thr Ile Gln Val Phe Ala Asp Ser Glu Tyr Gln Leu Pro
                195                 200                 205
Tyr Val Ile Gly Ser Ala Gln Glu Gly Cys Leu Pro Pro Phe Pro Pro
                210                 215                 220
Asp Val Phe Met Leu Pro Gln Tyr Gly Tyr Cys Thr Leu Asp Asn Asp
225                 230                 235                 240
Gly Lys Ser Leu Glu Arg Ser Ala Phe Tyr Cys Leu Glu Tyr Phe Pro
                245                 250                 255
Ser Gln Met Leu Arg Thr Gly Asn Asn Phe Glu Phe Ser Tyr Ala Phe
                260                 265                 270
Glu Ser Val Pro Phe His Ser Met Trp Met His Asn Gln Ser Leu Asp
                275                 280                 285
Arg Leu Met Asn Pro Leu Ile Asp Gln Tyr Leu Tyr Arg Phe Asp Asn
                290                 295                 300
Leu Thr Ser Gly Asn Thr Val Asn Pro Thr Phe Thr Tyr Lys Lys Gly
305                 310                 315                 320
Ser Ala Gly Asp Met Ala Ser Gln Ala Arg Asn Trp Leu Pro Gly Pro
                325                 330                 335
Met Leu Arg Asn Gln Gly Leu Met Asp Gly Pro Asn Asn Gln Ala Asn
                340                 345                 350
Leu Asp Gly Trp Arg Ile Ser Pro Pro Met Val Ile Asn Gly Lys Ser
                355                 360                 365
Ser Ile Ile Phe Pro Gly Pro Ser Met Tyr Thr Ala His Asn Ala Ala
                370                 375                 380
Asp Glu Leu Glu Val Gln Pro Ser Ile Asn Leu Pro Ile Phe Ala Lys
385                 390                 395                 400
Asp Ala Ser Val Pro Glu Ser Thr Ile Ile Ser Ser Ile Gly Asn Gln
                405                 410                 415
Asp Pro Asn Ser Lys Leu Leu Val Thr Asp Glu Asn Glu Val Gly Thr
                420                 425                 430
```

Val Asn Ala Thr Ala Ala Asn Thr Trp Gly Ser Met Ala Val Asn Gln
                435                 440                 445

Gln Thr Pro Thr Pro Thr Ser Ala Gly Gln Val Leu Asn Gln Met Gly
    450                 455                 460

Val Met Pro Gly Met Val Trp Gln Asn Arg Asp Ile Tyr Leu Gln Gly
465                 470                 475                 480

Pro Ile Trp Ala Lys Ile Pro His Thr Asp Gly His Phe His Pro Ser
                485                 490                 495

Pro Leu Met Gly Gly Phe Gly Leu Lys His Pro Pro Gln Ile Met
                500                 505                 510

Ile Lys Asn Thr Pro Val Pro Ala Asn Pro Ala Thr Ile Phe Thr Pro
                515                 520                 525

Val Lys Gln Asn Ser Phe Ile Thr Gln Tyr Ser Thr Gly Gln Val Thr
530                 535                 540

Val Glu Ile Glu Trp Glu Leu Gln Lys Glu Thr Ser Lys Lys Trp Asn
545                 550                 555                 560

Pro Glu Ile Gln Phe Thr Ser Asn Phe Arg Asn Thr Ile Asp Leu Pro
                565                 570                 575

Phe Ala Pro Asn Asn Glu Gly Val Tyr Ser Glu Pro Arg Pro Ile Gly
                580                 585                 590

Thr Arg Tyr Leu Thr Arg Pro Ile
                595                 600

<210> SEQ ID NO 36
<211> LENGTH: 1803
<212> TYPE: DNA
<213> ORGANISM: Artificial Sequence
<220> FEATURE:
<223> OTHER INFORMATION: mAAV-EVE1 deduced VP2 coding sequence

<400> SEQUENCE: 36
ctggagcctg tgaaaggaga aactcctgag aagctgcgca tccctcagca actccaaatc      60
cctcctcctc catctaagcg acaaaagacg agaggactcc ctttcaaccc aaacagcgac     120
aatggagcat acaccagcag tcagcaatca gccccccacta atttgggatc tggtatcatg     180
gcagaaggag gtggcgcacc aatgggcaat aatcaacagg gtgctgatgg agtgggtaat     240
tcctcaggaa attggcattg tgattcccaa tggatgggcc acagagtcgc acccgaaaa      300 actcacacct gggtcttgcc cacctacaac aaccacctct acaagcgagt tcaaaacagt     360
gtcaccacag gcagtgccaa caactacttt ggcttcagca cccctgggg tattttgac      420 ttcaacagat tccactgcca cttcagcccc cgagactggc aaagacttat caataacaac     480
tggggactgc gacctaaaaa cctgcacttc aaactcttca acatccaagt caaggaggtc     540
acaaggagga atgttgagac acaattgct aataaccta ccagcacgat tcaagtcttt     600
gcggactcag agtatcaact cccatacgtg atcaggagtg ctcaagaggg gtgtctactc     660
cccttccctc ctgatgtgtt tatgttgcct cagtatgggt attgtacttt ggacaatgat     720
gggaaaagtt tagagaggag tgcattctac tgtctagaat attttcctag ccaaatgttg     780
agaacgggta caactttga atttttcctat gcttttgaat ctgtcccctt tcatagcatg     840
tggatgcata atcagagctt ggatagattg atgaatccat tgattgatca atatctgtat     900
agatttgata tctaaccag tggaaacact gttaatccca ccttcactta caaaagggga     960
tcagcaggtg atatggcttc tcaggctagg aattggttac ctggtccat gcttaggaat    1020 cagggactaa tggatggtcc taacaatcag gccaatctag atggttggag gatcagtcct    1080

```
ccaatggtga tcaatggaaa atcttctatt atatttcctg ggccatccat gtataccgca    1140
cacaatgctg cagatgaact ggaggttcaa cctagcatta atctccctat ctttgctaaa    1200
gatgcctctg tacctgaatc caccataatt agtagtattg gtaatcaaga tcctaatagt    1260
aaattgttag tcactgatga gaacgaggtc gggacagtga atgctactgc tgctaatacc    1320
tgggggtcta tggcagtcaa ccagcagact cccaccccca ctagtgcagg acaggttcta    1380
aatcaaatga gtgtcatgcc tggaatggtc tggcagaata gagacatcga tctccatggt    1440
cccatttggg ctaagattcc tcacacagat ggttacttcc atccctctcc tctcatgggt    1500
ggctttggtc tcaaacatcc tcctcctcag attatgatta aaaacactcc tgtccctgct    1560
aaccctgcca ccatcttcac tcctgtcaaa caaaattctt tcatcactca atactctact    1620
ggtcaagtga ctgtagaaat tgaatgggaa ctccagaagg aaacctccaa gaatggaat     1680 cctgaaatcc agtttacttc caatttcaga aacactattg acttaccttt tgctcccaac    1740
aatgaaggtg tatactctga acctcgtccc attggtaccc gataccttac ccgtcccatc    1800
taa                                                                  1803

<210> SEQ ID NO 37
<211> LENGTH: 1803
<212> TYPE: DNA
<213> ORGANISM: Artificial Sequence
<220> FEATURE:
<223> OTHER INFORMATION: mAAV-EVE1 deduced, modified VP2 coding sequence

<400> SEQUENCE: 37
ctggcgcctg tgaaaggaga aactcctgag aagctgcgca tccctcagca actccaaatc      60
cctcctcctc catctaagcg acaaaagacg agaggactcc cttctcaaccc aaacagcgac    120 aatggagcat acaccagcag tcagcaatca gcccccacta atttgggatc tggtatcatg    180
gcagaaggag gtggcgcacc aatgggcgat aatcaacagg gtgctgatgg agtgggtaat    240
tcctcaggaa attggcattg tgattcccaa tggatgggca acagagtcgt caccgaaca     300 actcgcacct gggtcttgcc cacctacaac aaccacctct acaagcgaat tcaaaacagt    360
gtcaccacag gcagtgccaa caactacttt ggcttcagca ccccctgggg gtattttgac    420
ttcaacagat tccactgcca cttcagcccc cgagactggc aaagactat caataacaac     480 tggggactgc gacctaaaag cctgcgcttc aaactcttca acatccaagt caaggaggtc    540
acaacgacga atggcgagac acaattgct aataaccta ccagcacgat tcaagtcttt    600
gcggactcag agtatcaact cccatacgtg atcgggagtc tcaagagggg tgtctaccc      660 cccttccctc ctgatgtgtt tatgttgcct cagtatgggt attgtacttt ggacaatgat    720
gggaaaagtt tagagaggag tgcattctac tgtctagaat attttcctag ccaaatgttg    780
agaacgggta caacttttga atttcctat gcttttgaat ctgtccctt tcatagcatg      840 tggatgcaca atcagagctt ggatagattg atgaatccat tgattgatca atatctgtat    900
agatttgata atctaaccag tggaaacact gttaatccca ccttcactta caaaagggga    960
tcagcaggtg atatggcttc tcaggctagg aattggttac ctggtcctat gcttaggaat   1020
cagggactaa tggatggtcc taacaatcag gccaatctag atggttggag atcagtcct     1080 ccaatggtga tcaatggaaa atcttctatt atatttcctg ggccatccat gtataccgca   1140
cacaatgctg cagatgaact ggaggttcaa cctagcatta atctccctat ctttgctaaa   1200
gatgcctctg tacctgaatc caccataatt agtagtattg gtaatcaaga tcctaatagt   1260
```

-continued

```
aaattgttag tcactgatga gaacgaggtc gggacagtga atgctactgc tgctaatacc    1320
tgggggtcta tggcagtcaa ccagcagact cccaccccca ctagtgcagg acaggttcta    1380
aatcaaatgg gtgtcatgcc tggaatggtc tggcagaata gagacatcta tctccaaggt    1440
cccatttggg ctaagattcc tcacacagat ggtcacttcc atccctctcc tctcatgggt    1500
ggctttggtc tcaaacatcc tcctcctcag attatgatta aaaacactcc tgtccctgct    1560
aaccctgcca ccatcttcac tcctgtcaaa caaaattctt tcatcactca atactctact    1620
ggtcaagtga ctgtagaaat tgaatgggaa ctccagaagg aaacctccaa gaaatggaat    1680
cctgaaatcc agtttacttc caatttcaga aacactattg acttaccttt tgctcccaac    1740
aatgaaggtg tatactctga acctcgtccc attggtaccc gataccttac ccgtcccatc    1800
taa                                                                  1803
```

```
<210> SEQ ID NO 38
<211> LENGTH: 610
<212> TYPE: PRT
<213> ORGANISM: Adeno-Associated Virus

<400> SEQUENCE: 38

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
        195                 200                 205

Asp Pro Val Ile Lys Ser Lys Thr Ser Gln Lys Tyr Met Ala Leu Val
    210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270
```

```
Thr Lys Ser Ala Val Asp Tyr Leu Val Gly Ser Ser Val Pro Glu Asp
            275                 280                 285

Ile Ser Lys Asn Arg Ile Trp Gln Ile Phe Glu Met Asn Gly Tyr Asp
290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
        355                 360                 365

Met Leu Ile Trp Trp Glu Glu Gly Lys Met Thr Asn Lys Val Val Glu
370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Val Asp Gly Asn Ser Thr Thr Phe Glu
            420                 425                 430

His Gln Gln Pro Leu Glu Asp Arg Met Phe Lys Phe Glu Leu Thr Lys
        435                 440                 445

Arg Leu Pro Pro Asp Phe Gly Lys Ile Thr Lys Gln Glu Val Lys Asp
450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Arg Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
        515                 520                 525

Val Thr Val Asp Pro Ala Pro Leu Arg Pro Leu Asn Trp Asn Ser Arg
530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
                565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
        595                 600                 605

Glu Gln
610

<210> SEQ ID NO 39
<211> LENGTH: 621
<212> TYPE: PRT
<213> ORGANISM: Adeno-Associated Virus

<400> SEQUENCE: 39

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30
```

Lys Glu Trp Glu Leu Pro Pro Asp Ser Asp Met Asp Leu Asn Leu Ile
              35                  40                  45

Glu Gln Ala Pro Leu Thr Val Ala Glu Lys Leu Gln Arg Asp Phe Leu
 50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
             115                 120                 125

Pro Asn Trp Phe Ala Val Thr Lys Thr Arg Asn Gly Ala Gly Gly Gly
 130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
                260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

```
Glu Leu Thr Arg Arg Leu Asp His Asp Phe Gly Lys Val Thr Lys Gln
    450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
Pro Ser Asp Ala Asp Ile Ser Glu Pro Lys Arg Val Arg Glu Ser Val
                500                 505                 510
Ala Gln Pro Ser Thr Ser Asp Ala Glu Ala Ser Ile Asn Tyr Ala Asp
                515                 520                 525
Arg Tyr Gln Asn Lys Cys Ser Arg His Val Gly Met Asn Leu Met Leu
            530                 535                 540
Phe Pro Cys Arg Gln Cys Glu Arg Met Asn Gln Asn Ser Asn Ile Cys
545                 550                 555                 560
Phe Thr His Gly Gln Lys Asp Cys Leu Glu Cys Phe Pro Val Ser Glu
                565                 570                 575
Ser Gln Pro Val Ser Val Val Lys Lys Ala Tyr Gln Lys Leu Cys Tyr
            580                 585                 590
Ile His His Ile Met Gly Lys Val Pro Asp Ala Cys Thr Ala Cys Asp
        595                 600                 605
Leu Val Asn Val Asp Leu Asp Asp Cys Ile Phe Glu Gln
610                 615                 620

<210> SEQ ID NO 40
<211> LENGTH: 738
<212> TYPE: PRT
<213> ORGANISM: Adeno-Associated Virus

<400> SEQUENCE: 40

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Arg Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Ala Pro Ser Gly Val Gly Pro Asn Thr Met Ala Ala Gly Gly
        195                 200                 205
```

-continued

Gly Ala Pro Met Ala Asp Asn Glu Gly Ala Asp Gly Val Gly Ser
210                 215                 220

Ser Ser Gly Asn Trp His Cys Asp Ser Thr Trp Leu Gly Asp Arg Val
225             230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

```
Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
            690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
            725                 730                 735

Asn Leu

<210> SEQ ID NO 41
<211> LENGTH: 735
<212> TYPE: PRT
<213> ORGANISM: Adeno-Associated Virus

<400> SEQUENCE: 41

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
            165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
            210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255
```

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys

```
                675                 680                 685
Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

ADENO-ASSOCIATED VIRUS POLYNUCLEOTIDES, POLYPEPTIDES AND VIRIONS

RELATED APPLICATIONS

This application is associated with and claims priority from U.S. Provisional Patent Application No. 62/331,188, filed on 3 May 2016, entitled "Adeno-associated virus polynucleotides, polypeptides and virions", the entire contents of which are incorporated herein by reference.

FIELD OF INVENTION

The present disclosure relates generally to polypeptides encoded by an adeno-associated virus (AAV)-derived endogenous viral element (mAAV-EVE1) found within the germline of numerous closely-related marsupial species. The disclosure is also related to nucleic acid molecules encoding the polypeptides, vectors comprising the nucleic acid molecules and recombinant AAV virions comprising polypeptides. The disclosure also relates to uses of nucleic acid molecules, vectors and recombinant AAV virions.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 29358110_1.TXT, the date of creation of the ASCII text file is Nov. 2, 2018, and the size of the ASCII text file is 168 KB.

BACKGROUND OF THE DISCLOSURE

Gene therapy has most commonly been investigated and achieved using viral vectors, in particular adeno-associated viral vectors. Adeno-associated virus (AAV) is a replication-deficient parvovirus, the single-stranded DNA genome of which is about 4.7 kb in length. The AAV genome includes inverted terminal repeat (ITRs) at both ends of the molecule, flanking two open reading frames: cap and rep. The cap gene encodes three capsid proteins: VP1, VP2 and VP3. The three capsid proteins typically assemble in a ratio of 1:1:10 to form the AAV capsid, although AAV capsids containing only VP3, or VP1 and VP3, or VP2 and VP3, have been produced. The cap gene also encodes the assembly activating protein (AAP) from an alternative open reading frame. AAP promotes capsid assembly, acting to target the capsid proteins to the nucleolus and promote capsid formation. The rep gene encodes four regulatory proteins: Rep78, Rep68, Rep52 and Rep40. These Rep proteins are involved in AAV genome replication.

The ITRs are involved in several functions, in particular integration of the AAV DNA into the host cell genome, as well as genome replication and packaging. When AAV infects a host cell, the viral genome integrates into the host's chromosome resulting in latent infection of the cell. Thus, AAV can be exploited to introduce heterologous sequences into cells. In a natural system, a helper virus (for example, adenovirus or herpesvirus) provides genes that allow for production of AAV virus in the infected cell. In the case of adenovirus, genes E1A, E1B, E2A, E4 and VA provide helper functions. Upon infection with a helper virus, the AAV provirus is rescued and amplified, and both AAV and adenovirus are produced.

Recombinant AAVs containing a genome that lacks some, most or all of the native AAV genome and instead contains one or more heterologous sequences flanked by the ITRs have been successfully used in gene therapy settings. One of the major problems associated with the use of recombinant AAV is the pre-existing immunity in patients to AAV, particularly the AAV serotypes that most commonly circulate among humans, such as AAV2. The immune response is almost entirely directed to the capsid protein. Another problem is the limited tropism of the commonly used recombinant AAV virions. Thus, there is a continued need for alternative recombinant AAV virions, in particular those that contain capsid proteins that are distinct from those of the AAV serotypes in circulation and that are resistant to pre-existing immunity to AAV, and those with broader or different tropism.

SUMMARY OF THE DISCLOSURE

The present disclosure is predicated in part on the identification of an adeno-associated virus (AAV)-derived endogenous viral element (mAAV-EVE1) found within the germline of numerous closely-related marsupial species. Nucleic acid molecules containing the various mAAV-EVE1 genes, such as the capsid gene (cap) and fragments thereof, can be used to produce rAAV virions. The cap gene of mAAV-EVE1 and the encoded capsid polypeptides have limited homology to other known AAV serotypes. As a result, rAAV virions comprising these capsid polypeptides or fragments thereof are particularly useful for gene therapy in humans because pre-existing anti-AAV antibodies are unlikely to cross-react with the rAAV virions. The rAAV virions may also exhibit altered tropism, which may confer enhanced performance on the AAV system for gene addition and/or genome editing functions.

In one aspect, the present disclosure is directed to an isolated capsid polypeptide, comprising the sequence of amino acids set forth in SEQ ID NO:2 or a sequence having at least or about 70%, 75%, 80%, 85%, 90%, 91%, 92%, 93%, 94%, 95%, 96%, 97%, 98% or 99% sequence identity to the sequence set forth in SEQ ID NO:2. In some embodiments, the capsid polypeptide comprises the sequence of amino acids set forth in SEQ ID NO:1 or a sequence having at least or about 70%, 75%, 80%, 85%, 90%, 91%, 92%, 93%, 94%, 95%, 96%, 97%, 98% or 99% sequence identity to the sequence set forth in SEQ ID NO:1.

In particular examples, the capsid polypeptide comprises a region selected from among a phospholipase A2 (PLA2) domain set forth in amino acid residues 41-100 of SEQ ID NO:1; a VR-I set forth in amino acid residues 250-259 of SEQ ID NO:1; a VR-II set forth in amino acid residues 313-318 of SEQ ID NO:1; a VR-III set forth in amino acid residues 368-376 of SEQ ID NO:1; a VR-IV set forth in amino acid residues 436-454 of SEQ ID NO:1; a VR-V set forth in amino acid residues 473-489 of SEQ ID NO:1; a VR-VI set forth in amino acid residues 510-528 of SEQ ID NO:1; a VR-VII set forth in amino acid residues 531-552 of SEQ ID NO:1; a VR-VIII set forth in amino acid residues 575-590 of SEQ ID NO:1; and a VR-IX set forth amino acid residues 700-707 of SEQ ID NO:1, or corresponding regions of a polypeptide comprising the sequence of amino acids set forth in SEQ ID NO:1 or a sequence having at least or about 70%, 75%, 80%, 85%, 90%, 91%, 92%, 93%, 94%, 95%, 96%, 97%, 98% or 99% sequence identity to the sequence set forth in SEQ ID NO:1.

The present disclosure is also directed to a chimeric capsid polypeptide, comprising at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids of the mAAV-EVE capsid polypeptide set forth in SEQ ID NO:1 or the mAAV-EVE capsid polypeptide having at least or about 70%, 75%, 80%, 85%, 90%, 91%, 92%, 93%, 94%, 95%, 96%, 97%, 98% or 99% sequence identity to the mAAV-EVE capsid polypeptide set forth in SEQ ID NO: 1; and contiguous amino acids from a capsid protein other than the mAAV-EVE capsid polypeptide set forth in SEQ ID NO:1 or the mAAV-EVE capsid polypeptide having at least or about 70%, 75%, 80%, 85%, 90%, 91%, 92%, 93%, 94%, 95%, 96%, 97%, 98% or 99% sequence identity to the mAAV-EVE capsid polypeptide set forth in SEQ ID NO: 1. In some instances, the chimeric capsid polypeptide comprises at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids from a capsid protein other than the mAAV-EVE capsid polypeptide. In particular examples, the chimeric capsid polypeptide comprises the sequence of amino acids set forth in SEQ ID NO:2 or a sequence having at least or about 70%, 75%, 80%, 85%, 90%, 91%, 92%, 93%, 94%, 95%, 96%, 97%, 98% or 99% sequence identity to the sequence set forth in SEQ ID NO:2.

In one embodiment, the chimeric capsid polypeptide comprises a region selected from among a PLA2 domain set forth in amino acid residues 41-100 of SEQ ID NO:1; a VR-I set forth in amino acid residues 250-259 of SEQ ID NO:1; a VR-II set forth in amino acid residues 313-318 of SEQ ID NO:1; a VR-III set forth in amino acid residues 368-376 of SEQ ID NO:1; a VR-IV set forth in amino acid residues 436-454 of SEQ ID NO:1; a VR-V set forth in amino acid residues 473-489 of SEQ ID NO:1; a VR-VI set forth in amino acid residues 510-528 of SEQ ID NO:1; a VR-VII set forth in amino acid residues 531-552 of SEQ ID NO:1; a VR-VIII set forth in amino acid residues 575-590 of SEQ ID NO:1; and a VR-IX set forth amino acid residues 700-707 of SEQ ID NO:1, or corresponding regions of a polypeptide comprising the sequence of amino acids set forth in SEQ ID NO:1 or a sequence having at least or about 70%, 75%, 80%, 85%, 90%, 91%, 92%, 93%, 94%, 95%, 96%, 97%, 98% or 99% sequence identity to the sequence set forth in SEQ ID NO:1.

Also provided are recombinant AAV (rAAV) virions comprising a capsid polypeptide or a chimeric capsid polypeptide described above and herein. In particular embodiments, the rAAV further comprises a heterologous sequence.

The present disclosure further provides nucleic acid molecules encoding a capsid polypeptide or a chimeric capsid polypeptide described above and herein. In one embodiment, the nucleic acid molecule comprises the sequence set forth in SEQ ID NO:3 or a sequence having at least or about 70%, 75%, 80%, 85%, 90%, 91%, 92%, 93%, 94%, 95%, 96%, 97%, 98% or 99% sequence identity to the sequence set forth in SEQ ID NO:3.

The present disclosure is also directed to vectors comprising a nucleic acid molecule of described above and herein. In one example, the vector is selected from among a plasmid, cosmid, phage, transposon and viral vector. In instances where the vector is a viral vector, the viral may be, for example, an AAV, lentiviral, retroviral, adenoviral, herpesviral, hepatitis viral or baculoviral vector.

Also provided are host cells comprising a rAAV, a nucleic acid molecule and/or a vector described above and herein.

The present disclosure is also related to a method for introducing a heterologous sequence into a host cell, comprising contacting a host cell with a rAAV described above and herein that contains a heterologous sequence.

Also provided herein is a method for producing a chimeric capsid gene, comprising: (a) providing two or more AAV capsid genes from two or more serotypes of AAV, wherein at least one capsid gene encodes a capsid polypeptide described above and herein; (b) digesting the AAV capsid genes into fragments; and (c) reassembling the fragments using PCR to form a chimeric capsid gene. In some examples, the chimeric capsid gene encodes a region or domain of a capsid polypeptide as described above and herein. Using such methods, a library of chimeric capsid genes may be produced.

In some embodiments, the method for producing a chimeric capsid gene further comprises inserting the chimeric capsid gene into a vector, such as, for example, an AAV vector. Using such methods, a library of vectors may be produced. In particular embodiments, the AAV vectors are introduced into a host cell under conditions sufficient to produce a rAAV virion, thereby producing a rAAV virion comprising a chimeric capsid. In some instances, a library of rAAV virions is produced.

Also provided, therefore, are chimeric capsid genes and libraries thereof, vectors and libraries thereof, and rAAV and libraries thereof, produced by these methods.

The present disclosure is also directed to a method for producing a rAAV virion, comprising introducing into a cell a nucleic acid molecule described above and herein, an AAV rep gene, an AAV vector comprising a heterologous sequence flanked by inverted terminal repeats, and helper functions for generating a productive AAV infection; and allowing assembly of an rAAV virion comprising a capsid encoded by the nucleic acid molecule, wherein the capsid encapsidates the heterologous sequence.

BRIEF DESCRIPTION OF THE DRAWINGS

Embodiments of the disclosure are described herein, by way of non-limiting example only, with reference to the following drawings.

FIG. 2, (b) shows a ClustalW alignment (BLOSUM scoring matrix) of mAAV-EVE1 Rep (SEQ ID NO: 21) with the Rep proteins encoded by AAV5 (SEQ ID NO: 38) and AAV2 (SEQ ID NO: 39). Putative beta strands are indicated by blue arrows. Putative alpha helices are indicated by purple rectangles. FIG. 2, (c) is a schematic representation of the mAAV-EVE1 Rep nuclease domain based upon comparison to the AAV5 Rep nuclease domain. FIG. 2, (d) is a molecular model of mAAV-EVE1 Rep nuclease domain (residues 9 through 200) based upon the structural determination of the nuclease domain of AAV5 Rep (QMEAN z-score=−0.11).

FIG. 5 provides an alignment between the amino acid sequence of two mAAV-EVE1 capsid polypeptides: the initially-deduced capsid set forth in SEQ ID NO:1 and a modified capsid set forth in SEQ ID NO:30.

DETAILED DESCRIPTION

Figure 1:
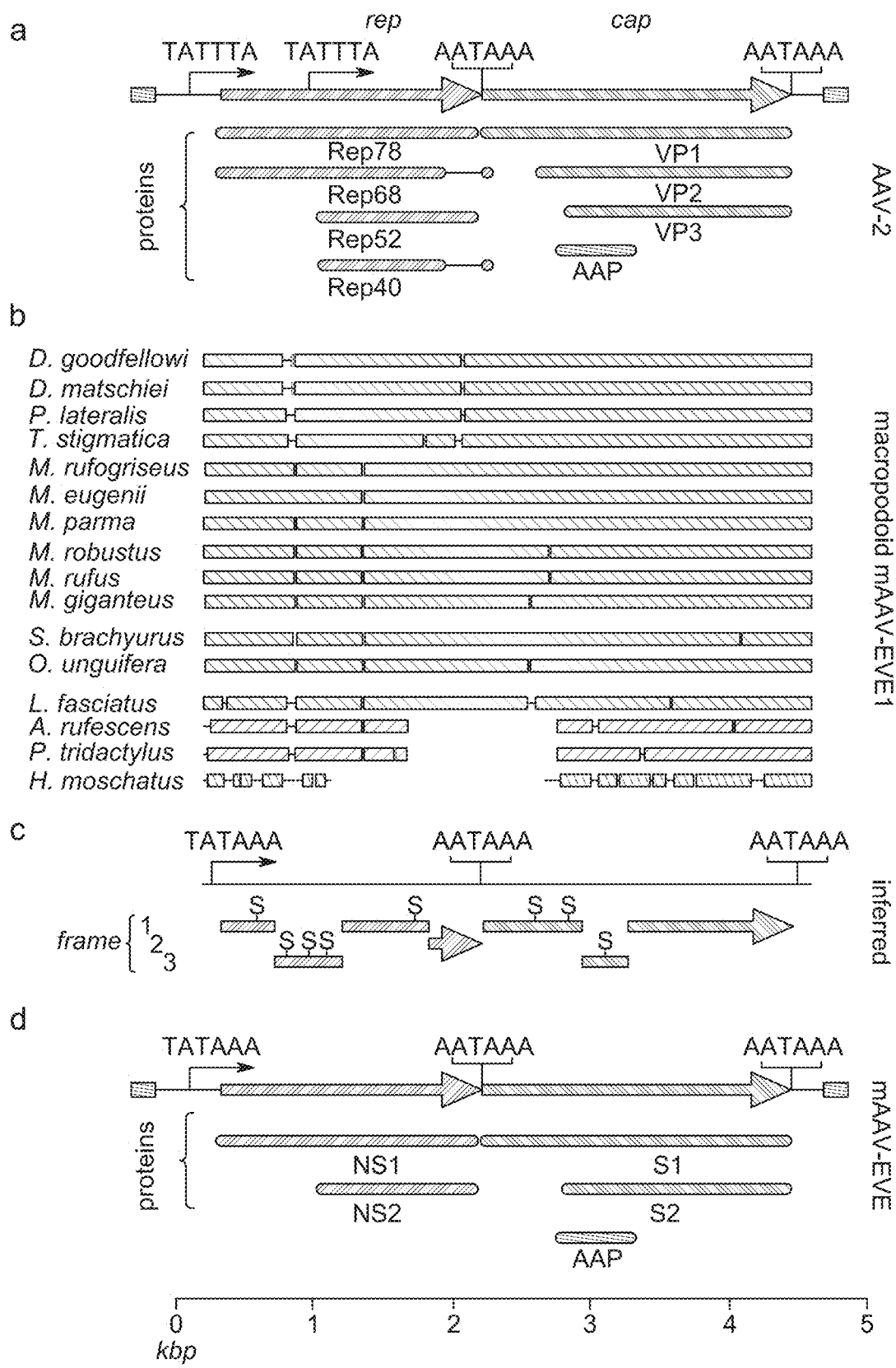
FIG. 1 depicts the maximum likelihood estimation of an inferred mAAV-EVE ancestral sequence. (a) Schematic representation of the genes and protein products encoded by the prototypical AAV serotype, AAV2. Relative positions of the p5 and p19 promoters ("TATA" boxes) and AATAAA polyadenylation signals are indicated. (b) Schematic representation of the genetic structure of endogenous mAAV sequences from sixteen macropodoid species. Species names are indicated at the left. Macropodidae elements are in blue, Potoroidea elements are in green, and the Hypsiprymnodontidae element is in yellow. Coloured rectangles indicate areas of significant similarity (90% identity, window length 50 bases). Gaps not bridged by a solid line represent deletions relative to the full-length mAAV-EVE1 consensus. (c) Raw, unedited maximum likelihood inference of the mAAV-EVE1 ancestral sequence. The rep gene is in red and the cap gene is in blue. Frameshifts are indicated by vertical discontinuities. Nonsense codons are represented by an "S". (d) Schematic depiction of putative ancestral exogenous viral sequences prior to mAAV-EVE1 endogenization, after editing for frameshifts, stop codons, and indels. NS1 and NS2, putative non-structural proteins; S1 and S2, putative structural proteins; AAP, putative assembly-activating protein.

Unless defined otherwise, all technical and scientific terms used herein have the same meaning as is commonly understood by one of skill in the art to which the disclosure belongs. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it understood that such identifiers can change and particular information on the internet can come and go, but equivalent information can be found by searching the internet. Reference to the identifier evidences the availability and public dissemination of such information.

As used herein, the singular forms "a", "an" and "the" also include plural aspects (i.e. at least one or more than one) unless the context clearly dictates otherwise. Thus, for example, reference to "a polypeptide" includes a single polypeptide, as well as two or more polypeptides.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, a "vector" refers to a nucleic acid molecule which is capable of capable of delivering a heterologous sequence contained within the vector into a host cell and is capable of replication when associated with the proper control elements. Vectors can be episomal, i.e., do not integrate into the genome of a host cell, or can integrate into the host cell genome. Exemplary vectors include, but are not limited to, plasmids, cosmids, phage, transposons and viral vectors, such as AAV, lentiviral, retroviral, adenoviral, herpesviral, hepatitis viral and baculoviral vectors.

As used herein, the term "AAV vector" refers to a vector derived from any adeno-associated virus serotype isolated from any animal species, including without limitation, AAV-1, AAV-2, AAV-3, AAV-4, AAV-5, AAV-6, AAV-7, AAV-8 and the mAAV-EVE described herein. Accordingly, an AAV vector includes at least one element of AAV origin and has the capacity to be packaged into a recombinant AAV virion. AAV vectors can have one or more of the AAV wild-type genes deleted in whole or part, but retain functional flanking ITR sequences, which are necessary for the rescue, replication and packaging of the AAV virion. Thus, an AAV vector includes at least those sequences required in cis for replication and packaging (e.g., functional ITRs) of the virus. The ITRs need not be the wild-type nucleotide sequences, and may be altered, e.g., by the insertion, deletion or substitution of nucleotides, as long as the sequences provide for functional rescue, replication and packaging. The AAV vector and/or virion can be utilized for the purpose of transferring heterologous sequences into cells either in vitro or in vivo.

The terms "recombinant AAV", "rAAV", "recombinant AAV virion", and "rAAV virion," are used interchangeably and refer to an infectious, replication-defective virus that includes an AAV protein shell encapsidating a heterologous sequence flanked on both sides by AAV ITRs. Recombinant AAV virions can be produced from host cells into which an AAV vector has been introduced. To facilitate packaging of the AAV vector, additional AAV-derived coding sequences, such as the AAV rep and cap genes, are also introduced into the host cell.

The term "ITR" refers to an inverted terminal repeat at either end of the AAV genome. This sequence can form hairpin structures and is involved in AAV DNA replication and rescue, or excision, from prokaryotic plasmids. ITRs for use in the present invention need not be the wild-type nucleotide sequences, and may be altered, e.g., by the insertion, deletion or substitution of nucleotides, as long as the sequences provide for functional rescue, replication and packaging of rAAV.

As used herein, "functional" with reference to a capsid polypeptide means that the polypeptide can self assemble or assemble with different capsid polypeptides to produce the proteinaceous shell (capsid) of an AAV virion. It is to be understood that not all capsid polypeptides in a given host cell assemble into AAV capsids. Preferably, at least 25%, at least 50%, at least 75%, at least 85%, at least 90%, at least 95% of all AAV capsid polypeptide molecules assemble into AAV capsids. Suitable assays for measuring this biological activity are described e.g. in Smith-Arica and Bartlett (2001), Curr Cardiol Rep 3(1): 43-49.

As used herein, "corresponding nucleotides" or "corresponding amino acid residues" refer to nucleotides or amino acids that occur at aligned loci. The sequences of related or variant polynucleotides or polypeptides are aligned by any method known to those of skill in the art. Such methods typically maximize matches (e.g. identical nucleotides or amino acids at positions), and include methods such as using manual alignments and by using the numerous alignment programs available (for example, BLASTN, BLASTP, Clust1W, Clust1W2, EMBOSS, LALIGN, Kalign, etc) and others known to those of skill in the art. By aligning the sequences of polynucleotides, one skilled in the art can identify corresponding nucleotides. For example, by aligning the mAAV-EVE1 cap gene set forth in SEQ ID NO:3 and one or more other mAAV-EVE1 cap genes set forth in SEQ ID NOs: 5-20, one of skill in the art can identify nucleotides within the other mAAV-EVE1 cap genes that correspond to particular regions or nucleotides, such as the VP3-encoding region, in mAAV-EVE1 cap gene set forth in SEQ ID NO:3. In another example, by aligning the mAAV-EVE1 capsid polypeptide set forth in SEQ ID NO:1 with another AAV capsid polypeptide, such as the one set forth in SEQ ID NO:30, one of skill in the art can identify amino acids residues within the other AAV polypeptide that correspond to VR-I at amino acid residues 250-259 of SEQ ID NO:1 (i.e. amino acid residues 250-259 of SEQ ID NO:30).

A "heterologous sequence" as used herein refers to nucleic acid sequence present in a polynucleotide, vector, or host cell that is not naturally found in the polynucleotide, vector, or host cell or is not naturally found at the position that it is at in the polynucleotide, vector, or host cell, i.e. is non-native. A "heterologous sequence" can encode a peptide or polypeptide, or a polynucleotide that itself has a function or activity, such as an antisense or inhibitory oligonucleotide, including antisense DNA and RNA (e.g. miRNA, siRNA, and shRNA). In some examples, the heterologous sequence is a stretch of nucleic acids that is essentially homologous to a stretch of nucleic acids in the genomic DNA of an animal, such that when the heterologous sequence is introduced into a cell of the animal, homologous recombination between the heterologous sequence and the genomic DNA can occur.

As used herein, the term "operably-linked" with reference to a promoter and a coding sequence means that the transcription of the coding sequence is under the control of, or driven by, the promoter.

The term "host cell" refers to a cell, such as a mammalian cell, that has introduced into it exogenous DNA, such as a vector. The term includes the progeny of the original cell into which the exogenous DNA has been introduced. Thus, a "host cell" as used herein generally refers to a cell that has been transfected or transduced with exogenous DNA.

As used herein, "isolated" with reference to a nucleic acid molecule means that the nucleic acid molecule is substantially free of cellular material or other contaminating proteins from the cells from which the nucleic acid molecule is derived, or substantially free from chemical precursors or other chemicals when chemically synthesized.

The term "subject" as used herein refers to an animal, in particular a mammal and more particularly a primate including a lower primate and even more particularly, a human who can benefit from the present invention. A subject regardless of whether a human or non-human animal or embryo may be referred to as an individual, subject, animal, patient, host or recipient. The present invention has both human and veterinary applications. For convenience, an "animal" specifically includes livestock animals such as cattle, horses, sheep, pigs, camelids, goats and donkeys, as well as domestic animals, such as dogs and cats. With respect to horses, these include horses used in the racing industry as well as those used recreationally or in the livestock industry. Examples of laboratory test animals include mice, rats, rabbits, guinea pigs and hamsters. Rabbits and rodent animals, such as rats and mice, provide a convenient test system or animal model as do primates and lower primates. In some embodiments, the subject is human.

It will be appreciated that the above described terms and associated definitions are used for the purpose of explanation only and are not intended to be limiting.

TABLE 1

Brief Description of the Sequences

| SEQ ID NO. | Description |
|---|---|
| 1 | mAAV-EVE1 deduced capsid protein (VP1) |
| 2 | mAAV-EVE1 deduced VP3 protein |
| 3 | mAAV-EVE1 deduced cap gene (VP1 coding sequence) |
| 4 | mAAV-EVE1 deduced VP3 coding sequence |
| 5 | mAAV-EVE1 cap gene (*Macropus rufogriseus*) |
| 6 | mAAV-EVE1 cap gene (*Macropus rufus*) |
| 7 | mAAV-EVE1 cap gene (*Macropus parma*) |
| 8 | mAAV-EVE1 cap gene (*Macropus robustus*) |
| 9 | mAAV-EVE1 cap gene (*Macropus giganteus*) |
| 10 | mAAV-EVE1 cap gene (*Macropus eugenii*) |
| 11 | mAAV-EVE1 cap gene (*Lagorchestes conspicillatus*) |
| 12 | mAAV-EVE1 cap gene (*Setonix brachyurus*) |
| 13 | mAAV-EVE1 cap gene (*Onychogalea unguifera*) |
| 14 | mAAV-EVE1 cap gene (*Dendrolagus matschiei*) |
| 15 | mAAV-EVE1 cap gene (*Dendrolagus goodfellowi*) |
| 16 | mAAV-EVE1 cap gene (*Petrogale lateralis*) |
| 17 | mAAV-EVE1 cap gene (*Thylogale stigmatica*) |
| 18 | mAAV-EVE1 cap gene (*Lagostrophus fasciatus*) |
| 19 | mAAV-EVE1 cap gene (*Aepyprymnus rufescens*) |
| 20 | mAAV-EVE1 cap gene (*Hypsiprymnodon moschatus*) |
| 21 | mAAV-EVE1 deduced Rep protein |
| 22 | mAAV-EVE1 deduced rep gene |
| 23 | AA55 primer |
| 24 | SIG primer |
| 25 | AAV-EVE_flank_up primer |
| 26 | AAVEVE_flank_dwn primer |
| 27 | Macr(-335)flank_up primer |
| 28 | mAAV-EVE1 deduced AAP protein |
| 29 | mAAV-EVE1 deduced aap gene |
| 30 | mAAV-EVE1 deduced, modified capsid protein (VP1) |
| 31 | mAAV-EVE1 deduced, modified VP3 protein |
| 32 | mAAV-EVE1 deduced, modified cap gene (VP1 coding sequence) |
| 33 | mAAV-EVE1 deduced, modified VP3 coding sequence |
| 34 | mAAV-EVE1 deduced VP2 protein |
| 35 | mAAV-EVE1 deduced, modified VP2 protein |
| 36 | mAAV-EVE1 deduced VP2 coding sequence |
| 37 | mAAV-EVE1 deduced, modified VP2 coding sequence | mAAV-EVE1 Nucleic Acid Molecules and Polypeptides

Figure 2:
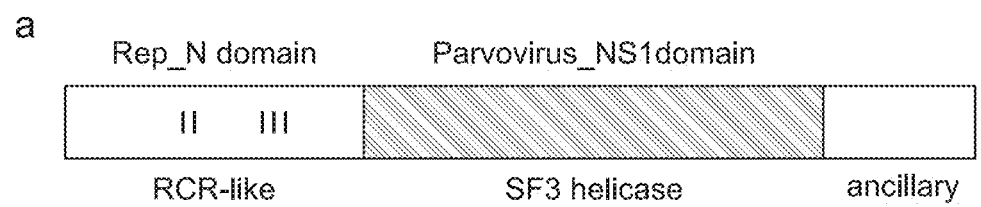
FIG. 2 shows the mAAV-EVE1 Rep protein. More specifically, FIG. 2, (a) is a schematic representation of the mAAV-EVE1 Rep protein consisting of an amino-terminal nuclease domain, a central SFIII helicase domain, and a unique carboxy-terminal ancillary domain.
Figure 2:
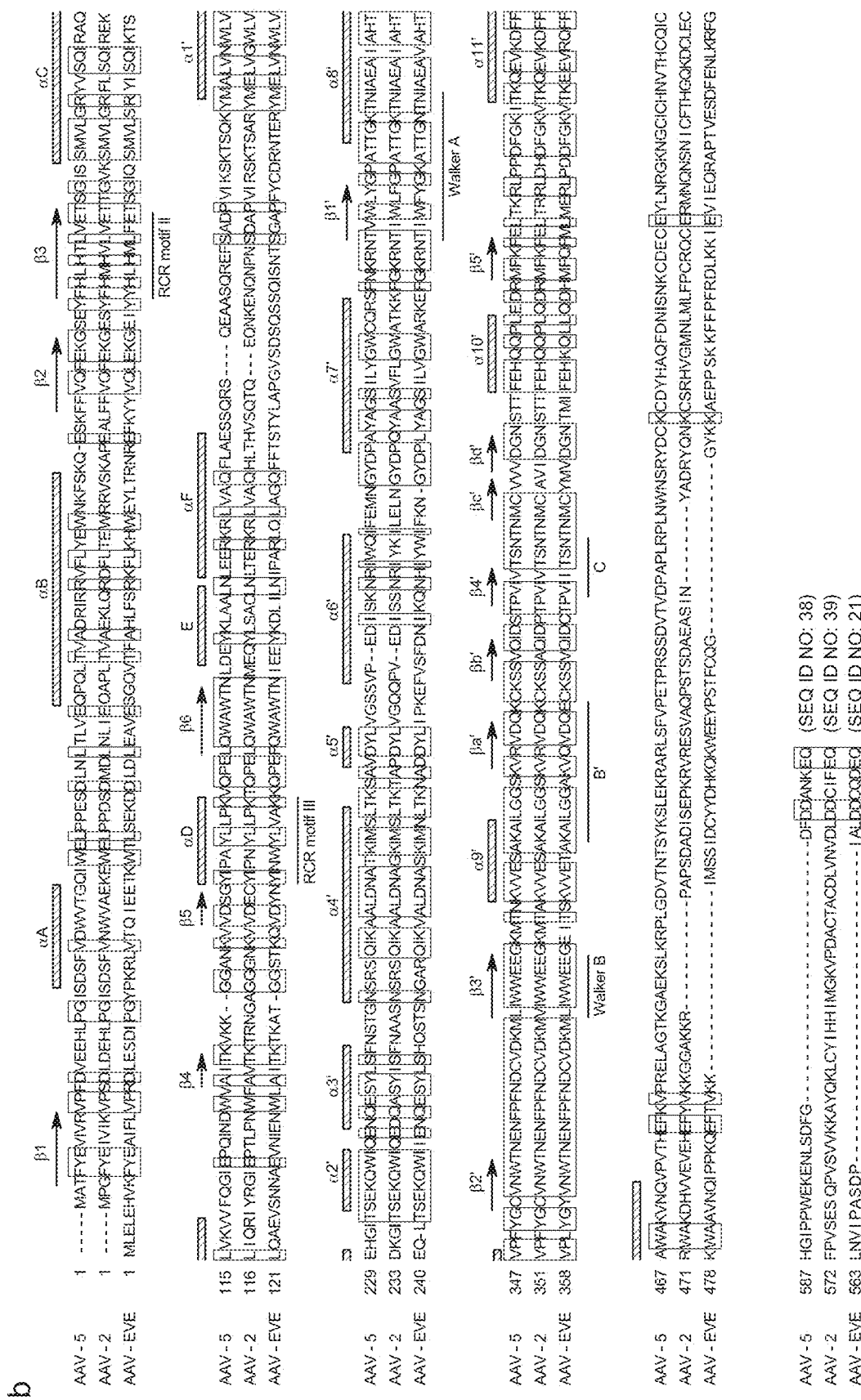
Figure 2:
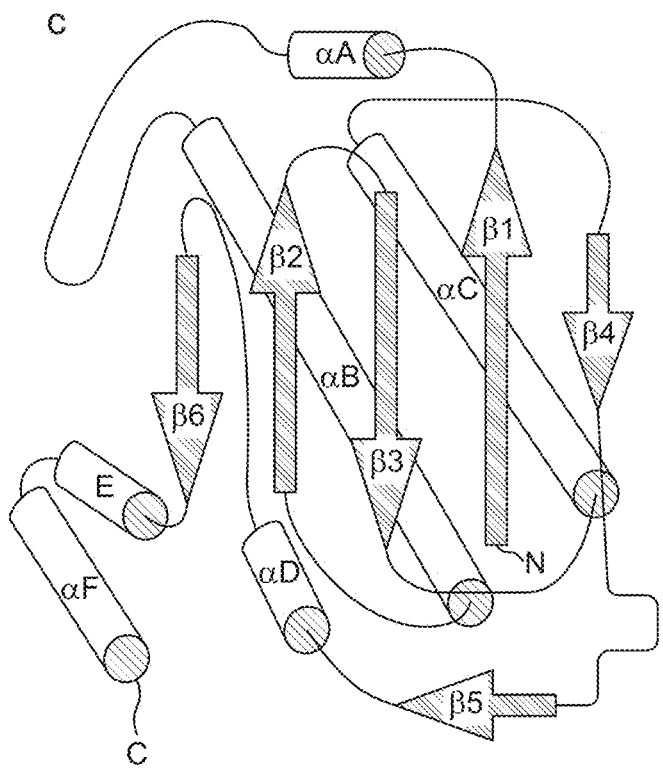
Figure 2:
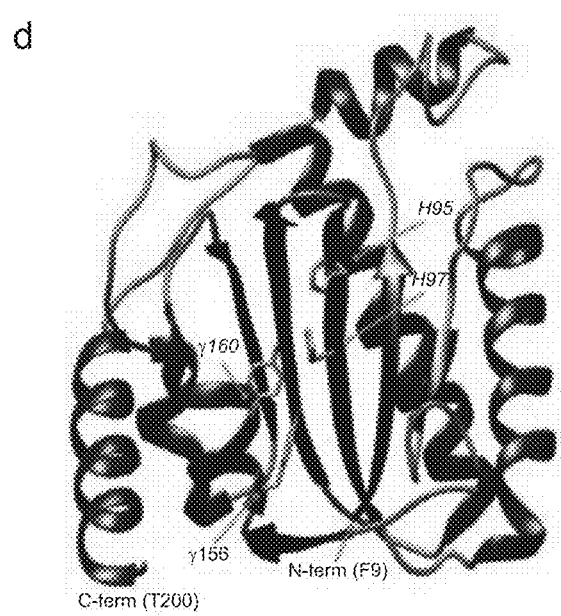
Figure 3:
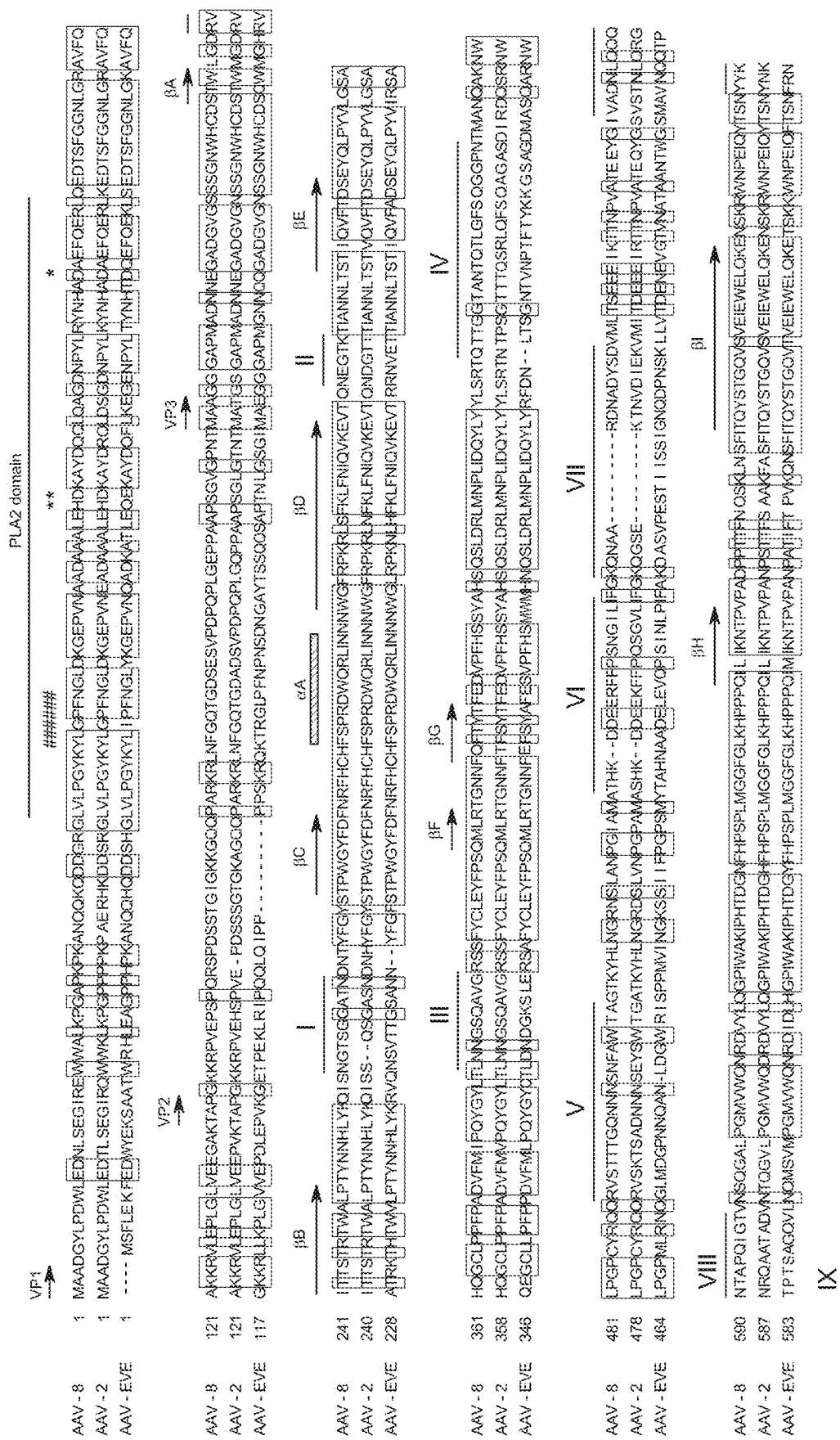
FIG. 3 depicts mAAV-EVE1 structural proteins. ClustalW alignment (BLOSUM scoring matrix) of AAV8 (SEQ ID NO: 40), AAV2 (SEQ ID NO: 41), and mAAV-EVE1 (SEQ ID NO: 30) VP1 coat proteins. Beta-strands are indicated by arrows. The position of the lone α-helix is indicated by a purple rectangle. PLA2, phospholipase A2 domain. Catalytic residues of the PLA2 domain are indicated by asterisks. Residues know to form a calcium-binding loop are indicated by hashtags.

The present disclosure is predicated in part on the identification of an adeno-associated virus (AAV)-derived endogenous viral element (mAAV-EVE1) found within the germline of numerous closely-related marsupial species. As described herein, the mAAV-EVE1 comprises the major structural and non-structural genes observed in other AAV serotypes (FIG. 1), although with relatively limited sequence homology (FIGS. 2 and 3). The mAAV-EVE1 cap gene encodes capsid polypeptides, including at least a VP1 protein and a VP3 protein (FIG. 3). Also encoded by the cap gene is an AAP polypeptide (FIG. 1). The mAAV-EVE1 also contains a rep gene that encodes a Rep protein (FIG. 2). Thus, provided herein are polypeptides comprising all or a portion of the mAAV-EVE1 capsid polypeptides, including polypeptides comprising all or a portion of the VP1 protein and/or the VP3 protein, and variants thereof. Also provided are nucleic acid molecules encoding all or a portion of the mAAV-EVE1 capsid polypeptides and variants thereof. Additionally, provided are polypeptides comprising all or a portion of the mAAV-EVE1 Rep protein or AAP protein and variants thereof, and nucleic acid molecules encoding such polypeptides.

mAAV-EVE1 Capsid

Provided herein are isolated capsid polypeptides. The capsid polypeptides of the present disclosure have amino acid sequences that are quite distinct and divergent from other AAV capsid polypeptides described previously, including capsid polypeptides from AAV serotypes that commonly circulate amongst humans. Accordingly, the capsid polypeptides of the present disclosure are particularly useful for producing rAAV virions for gene therapy.

Capsid polypeptides of the present disclosure include those that comprise all or a portion of a mAAV-EVE1 VP1 protein, such as a VP1 protein having an amino acid sequence set forth in SEQ ID NO:1 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:1. Thus, provided are capsid polypeptides comprising an amino acid sequence set forth in SEQ ID NO:1 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:1. In one example, the capsid polypeptide comprises a sequence set forth in SEQ ID NO:30. The present disclosure also provides VP1 polypeptides comprising a sequence having at least or about 75%, 80%, 85%, 90%, 91%, 92%, 93%, 94%, 95%, 96%, 97%, 98% or 99% sequence identity to a sequence set forth in SEQ ID NO:30.

Also provided are capsid polypeptides that comprise all or a portion of the mAAV-EVE1 VP3 protein, such as a VP3 protein with an amino acid sequence set forth in SEQ ID NO:2 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:2. Thus, provided are polypeptides comprising an amino acid sequence set forth in SEQ ID NO:2 or an amino acid sequence having at least or about 70%, 75%, 80%, 85%, 90%, 91%, 92%, 93%, 94%, 95%, 96%, 97%, 98% or 99% sequence identity to a sequence set forth in any one of SEQ ID NO:2. In one example, the polypeptide comprises a sequence set forth in SEQ ID NO:31. Also provided are VP3 polypeptides comprising a sequence having at least or about 75%, 80%, 85%, 90%, 91%, 92%, 93%, 94%, 95%, 96%, 97%, 98% or 99% sequence identity to a sequence set forth in SEQ ID NO:31.

Also provided are capsid polypeptides that comprise all or a portion of the mAAV-EVE1 VP2 protein, such as a VP2 protein with an amino acid sequence set forth in SEQ ID NO:34 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:34. Thus, provided are polypeptides comprising an amino acid sequence set forth in SEQ ID NO:34 or an amino acid sequence having at least or about 70%, 75%, 80%, 85%, 90%, 91%, 92%, 93%, 94%, 95%, 96%, 97%, 98% or 99% sequence identity to a sequence set forth in any one of SEQ ID NO:34. In one example, the polypeptide comprises a sequence set forth in SEQ ID NO:35. Also provided are VP2 polypeptides comprising a sequence having at least or about 75%, 80%, 85%, 90%, 91%, 92%, 93%, 94%, 95%, 96%, 97%, 98% or 99% sequence identity to a sequence set forth in SEQ ID NO:35.

The capsid polypeptides of the present invention include those comprising a fragment of a mAAV-EVE1 VP1, VP2 or VP3 protein, such as a fragment of a polypeptide comprising an amino acid set forth in SEQ ID NO:1, 34 or 2 or a fragment of a polypeptide having an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:1, 34 or 2. In particular examples, the fragment is a fragment of a polypeptide comprising an amino acid set forth in SEQ ID NO:30, 35 or 31 or an amino acid sequence having at least or about 75%, 80%, 85%, 90%, 91%, 92%, 93%, 94%, 95%, 96%, 97%, 98% or 99% sequence identity to a sequence set forth in SEQ ID NO:30, 35 or 31. The fragment may be of any length but is typically at least 31 amino acids long. Exemplary fragments include those that comprise at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids of a polypeptide having an amino acid sequence set forth in SEQ ID NO:1, 2, 30, 31, 34 or 35 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO: 1, 2, 30, 31, 34 or 35. Exemplary fragments include those containing the VP3 protein (e.g. SEQ ID NO:2 or SEQ ID NO:31; corresponding to amino acid residues 191-731 of SEQ ID NO:1 and SEQ ID NO:30, respectively), those that contain the phospholipase A2 (PLA2) domain (amino acid residues 41-100 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:1 or SEQ ID NO:30) and those containing any one or more of the variable regions (VR), including VR-I (amino acid residues 250-259 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:1 or SEQ ID NO:30); VR-II (amino acid residues 313-318 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to a sequence set forth in SEQ ID NO:1 or SEQ ID NO:30); (amino acid residues 368-376 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to a sequence set forth in SEQ ID NO:1 or SEQ ID NO:30); VR-IV (amino acid residues 436-454 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to a sequence set forth in SEQ ID NO:1 or SEQ ID NO:30); VR-V (amino acid residues 473-489 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to a sequence set forth in SEQ ID NO:1 or SEQ ID NO:30); VR-VI (amino acid residues 510-528 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to a sequence set forth in SEQ ID NO:1 or SEQ ID NO:30); VR-VII (amino acid residues 531-552 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to a sequence set forth in SEQ ID NO:1 or SEQ ID NO:30); VR-VIII (amino acid residues 575-590 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to a sequence set forth in SEQ ID NO:1 or SEQ ID NO:30); and VR-IX (amino acid residues 700-707 of SEQ ID NO:1 or SEQ ID NO:30 or corresponding residues in a sequence having at least or about 70%, 75%, 80%, 85%, 90%, 91%, 92%, 93%, 94%, 95%, 96%, 97%, 98% or 99% sequence identity to a sequence set forth in SEQ ID NO:1 or SEQ ID NO:30).

The fragments can be functional fragments, i.e. can self-assemble to form an AAV capsid (alone or when present with other capsid polypeptides) that facilitates binding and internalization of the rAAV virion into a host cell. Exemplary of the functional fragments contemplated herein are those that include a mAAV-EVE1 VP3 protein, such as a VP3 protein comprising an amino acid sequence set forth in SEQ ID NO:2 or SEQ ID NO:31 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:2 or SEQ ID NO:31.

In other examples, the fragments are functional when part of a chimeric capsid polypeptide, i.e. the chimeric polypeptide can self assemble or assemble with other capsid polypeptides to the AAV capsid of a rAAV virion. For example, the fragment can be part of a chimeric capsid protein that also contains fragments of capsid proteins from one or more other AAV serotypes, including, but not limited to, AAV1, AAV2, AAV3, AAV4, AAV5, AAV6, AAV7 and AAV8. Thus, also provided are capsid polypeptides that are chimeric and that include at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids of the mAAV-EVE capsid polypeptide set forth in SEQ ID NO:1 or SEQ ID NO:30 or a mAAV-EVE capsid polypeptide having at least or about 70%, 75%, 80%, 85%, 90%, 91%, 92%, 93%, 94%, 95%, 96%, 97%, 98% or 99% sequence identity to the mAAV-EVE capsid polypeptide set forth in SEQ ID NO: 1 or SEQ ID NO:30. The chimeric capsid polypeptides also comprise contiguous amino acids from a capsid protein other than the mAAV-EVE capsid polypeptide set forth in SEQ ID NO:1 or SEQ ID NO:30 or a mAAV-EVE capsid polypeptide having at least or about 70%, 75%, 80%, 85%, 90%, 91%, 92%, 93%, 94%, 95%, 96%, 97%, 98% or 99% sequence identity to the mAAV-EVE capsid polypeptide set forth in SEQ ID NO: 1 or SEQ ID NO:30. For example, the chimeric capsid polypeptide can include contiguous amino acids from one or more capsid proteins from one or more of AAV1, AAV2, AAV3, AAV4, AAV5, AAV6, AAV7 or AAV8. The amino acid sequences of numerous AAV serotypes have been described and are well known in the art, and can be used to produce the chimeric capsid polypeptides of the invention. It is contemplated that the chimeric capsid polypeptides can comprise any number of contiguous amino acids from a capsid protein other than the mAAV-EVE capsid polypeptide, provided the resulting chimeric capsid polypeptide is functional. In some embodiments, the chimeric capsid polypeptide comprises at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids from a capsid protein other than the mAAV-EVE capsid polypeptide.

Also contemplated herein are nucleic acid molecules encoding the capsid polypeptides of the present disclosure. Accordingly, provided are nucleic acid molecules encoding a capsid polypeptide comprising the amino acid sequence set forth in SEQ ID NOs: 1, 2, 30, 31, 34 or 35 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO: 1, 2, 30, 31, 34 or 35, or a fragment thereof. Exemplary nucleic acid molecules include those that comprise the sequence set forth in SEQ ID NOs:3, 4, 32, 33, 36 or 37 or a sequence having at least or about 70%, 75%, 80%, 85%, 90%, 91%, 92%, 93%, 94%, 95%, 96%, 97%, 98% or 99% sequence identity to the sequence set forth in SEQ ID NO:3, 4, 32, 33, 36 or 37 or a fragment thereof. In particular examples, the nucleic acid molecules include a promoter operably linked to the nucleic acid encoding the polypeptides, such that the polypeptides can be expressed in a host cell.

mAAV-EVE1 AAP

The present disclosure also provides polypeptides that comprise all or a portion of the mAAV-EVE1 AAP protein. Thus, provided are AAP polypeptides comprising the amino acid sequence set forth in SEQ ID NO:28 or an amino acid sequence having at least or about 70%, 75%, 80%, 85%, 90%, 91%, 92%, 93%, 94%, 95%, 96%, 97%, 98% or 99% sequence identity to a sequence set forth in any one of SEQ ID NO:28.

Also provided are AAP polypeptides comprising a fragment of a mAAV-EVE1 AAP protein, such as a fragment of a polypeptide having an amino acid sequence set forth in SEQ ID NO:28 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:28. The fragment may be of any length but is typically at least 20 amino acids long. Exemplary fragments include those that comprise at least or about 20, 25, 35, 40, 45, 50, 55, 60, 65, 75, 80, 85, 90, 95, 100, 120, 140, 160, 180 or 200 contiguous amino acids of a polypeptide having an amino acid sequence set forth in SEQ ID NO:28 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:28. The fragments can be functional fragments, i.e. can promote AAV capsid formation, which can be assessed using assays well known in the art. For example, the ability of AAP to promote capsid formation of VP3 alone can be assessed as described by, for example, Sontag et al. (J. Virol. (2011) 85:12686-12697).

mAAV-EVE1 Rep

Polypeptides of the present disclosure include those that comprise all or a portion of the mAAV-EVE1 Rep protein. Thus, provided are Rep polypeptides comprising the amino acid sequence set forth in SEQ ID NO:21 or an amino acid sequence having at least or about 70%, 75%, 80%, 85%, 90%, 91%, 92%, 93%, 94%, 95%, 96%, 97%, 98% or 99% sequence identity to a sequence set forth in any one of SEQ ID NO:21.

Also provided are Rep polypeptides comprising a fragment of a mAAV-EVE1 Rep protein, such as a fragment of a polypeptide having an amino acid sequence set forth in SEQ ID NO:21 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:21. The fragment may be of any length but is typically at least 20 amino acids long. Exemplary fragments include those that comprise at least or about 20, 25, 35, 40, 45, 50, 55, 60, 65, 75, 80, 85, 90, 95, 100, 120, 140, 160, 180, 200, 250, 300, 350, 400, 450, 500 or 550 contiguous amino acids of a polypeptide having an amino acid sequence set forth in SEQ ID NO:21 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:21. In one example, the fragment comprises the NS2 protein set forth at amino acids 232-581 of SEQ ID NO:21.

The present disclosure also provides nucleic acid molecules encoding the Rep polypeptides of the present disclosure. Accordingly, provided are nucleic acid molecules encoding a Rep polypeptide comprising the amino acid sequence set forth in SEQ ID NO:21 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:21, or a fragment thereof. In particular examples, the nucleic acid molecule includes a promoter operably linked to the nucleic acid encoding the polypeptide, such that the polypeptide can be expressed in a host cell. The fragments can be functional fragments, i.e. can facilitate AAV replication, and can be assessed using standard assays for Rep function, such as described by Chiorini et al. (1994) J Virol. 68(2): 797-804.

Vectors

The present disclosure also provides vectors comprising a nucleic acid molecule described herein, such as one that encodes a capsid polypeptide, AAP polypeptide and/or Rep polypeptide. Typically the nucleic acid encoding the capsid polypeptide, AAP polypeptide and/or Rep polypeptide is operably linked to a promoter to allow for expression of the capsid polypeptide and/or Rep protein or fragment thereof. The vectors can be episomal vectors (i.e., that do not integrate into the genome of a host cell), or can be vectors that integrate into the host cell genome. Exemplary vectors include, but are not limited to, plasmids, cosmids, and viral vectors, such as AAV, lentiviral, retroviral, adenoviral, herpesviral, and hepatitis viral vectors. In particular examples, the vectors are plasmids. In other examples, the vectors are AAV vectors. The choice and design of an appropriate vector is within the ability and discretion of one of ordinary skill in the art.

Vectors of the present disclosure can comprise nucleic acid described herein that encodes all or a portion of a mAAV-EVE1 capsid polypeptide, e.g. that encode polypeptides comprising an amino acid sequence set forth in SEQ ID NO:1, 2, 30, 31, 34 or 35 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:1, 2, 30, 31, 34 or 35 or fragments thereof, as described above. Such vectors can be used for the production of rAAV virions comprising a mAAV-EVE1 capsid polypeptide described herein. In particular examples, the vectors also comprise nucleic acid encoding an AAP protein, such as a mAAV-EVE1 AAP protein or fragment thereof as described herein or an AAP protein from another AAV serotype; and/or also comprise nucleic acid encoding a Rep protein, such as a mAAV-EVE1 Rep protein or fragment thereof as described herein or a Rep protein from another AAV serotype.

In some embodiments, the vectors of the present disclosure function to provide the mAAV-EVE1 capsid polypeptides, AAP polypeptides and/or Rep polypeptides or fragments thereof in trans for the production of rAAV virions. For example, in such embodiments, the vector may be co-transfected into a host cell with an AAV vector containing a heterologous sequence flanked by ITRs and a helper plasmid or helper virus such that rAAV virions containing the mAAV-EVE1 capsid polypeptides and encapsidating the heterologous sequence is produced. In other embodiments, the vectors are AAV vectors that provide the mAAV-EVE1 capsid polypeptides or fragments thereof in cis for the production of rAAV virions containing the capsid polypeptides. For such examples, the AAV vector typically also contains a heterologous sequence that will be packaged into the rAAV virion.

Thus, in some embodiments, the vectors of the present invention also comprise a heterologous sequence. The heterologous sequence may be operably linked a promoter to facilitate expression of the sequence. The heterologous sequence can encode a peptide or polypeptide, such as a therapeutic peptide or polypeptide, or can encode a polynucleotide or transcript that itself has a function or activity, such as an antisense or inhibitory oligonucleotide, including antisense DNA and RNA (e.g. miRNA, siRNA, and shRNA). In some examples, the heterologous sequence is a stretch of nucleic acids that is essentially homologous to a stretch of nucleic acids in the genomic DNA of an animal, such that when the heterologous sequence is introduced into a cell of the animal, homologous recombination between the heterologous sequence and the genomic DNA can occur. As would be appreciated, the nature of the heterologous sequence is not essential to the present disclosure. In particular embodiments, the vectors comprising the heterologous sequence(s) will be used in gene therapy.

In particular examples, the heterologous sequence encodes a peptide or polypeptide, or polynucleotide, whose expression is of therapeutic use, such as, for example, for the treatment of a disease or disorder. For example, expression of a therapeutic peptide or polypeptide may serve to restore or replace the function of the endogenous form of the peptide or polypeptide that is defective (i.e. gene replacement therapy). In other examples, expression of a therapeutic peptide or polypeptide, or polynucleotide, from the heterologous sequence serves to alter the levels and/or activity of one or more other peptides, polypeptides or polynucleotides in the host cell. Thus, according to particular embodiments, the expression of a heterologous sequence introduced by a vector described herein into a host cell can be used to provide a therapeutic amount of a peptide, polypeptide or polynucleotide to ameliorate the symptoms of a disease or disorder. In other instance, the heterologous sequence is a stretch of nucleic acids that is essentially homologous to a stretch of nucleic acids in the genomic DNA of an animal, such that when the heterologous sequence is introduced into a cell of the animal, homologous recombination between the heterologous sequence and the genomic DNA can occur. Accordingly, the introduction of a heterologous sequence by a vector or rAAV described herein into a host cell can be used to correct mutations in genomic DNA, which in turn can ameliorate the symptoms of a disease or disorder.

In embodiments where the vector is an AAV vector, the heterologous sequence is flanked by 3' and 5' AAV ITRs to allow packaging of the heterologous sequence into a rAAV virion. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV1, AAV2, AAV3, AAV4, AAV5, AAV6, AAV7 and AAV8, etc. Such ITRs and vectors comprising them are well known in the art.

Vectors suitable for use in mammalian cells are widely described and well-known in the art. Those skilled in the art would appreciate that vectors of the present invention may also contain additional sequences and elements useful for the replication of the vector in prokaryotic and/or eukaryotic cells, selection of the vector and the expression of a heterologous sequence in a variety of host cells. For example, the vectors of the present disclosure can include a prokaryotic replicon (that is, a sequence having the ability to direct autonomous replication and maintenance of the vector extrachromosomally in a prokaryotic host cell, such as a bacterial host cell. Such replicons are well known in the art. In some embodiments, the vectors can include a shuttle element that makes the vectors suitable for replication and integration in both prokaryotes and eukaryotes. In addition, vectors may also include a gene whose expression confers a detectable marker such as a drug resistance gene, which allows for selection and maintenance of the host cells. Vectors may also have a reportable marker, such as gene encoding a fluorescent or other detectable protein.

The vectors of the present invention comprise promoters that facilitate expression of an operably linked coding region, such as a cap, aap or rep gene or heterologous sequence. In some examples, the promoters are AAV promoters, such as the p5, p19 or p40 promoter. In other example, the promoters are derived from other sources. Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1α, promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Non-limiting examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In some embodiments, tissue specific promoters are used. Non-limiting examples of such promoters include the liver-specific thyroxin binding globulin (TBG) promoter, insulin promoter, glucagon promoter, somatostatin promoter, pancreatic polypeptide (PPY) promoter, synapsin-1 (Syn) promoter, creatine kinase (MCK) promoter, mammalian desmin (DES) promoter, a α-myosin heavy chain (a-MHC) promoter, a cardiac Troponin T (cTnT) promoter, beta-actin promoter, and hepatitis B virus core promoter. The selection of an appropriate promoter is well within the ability of one of ordinary skill in the art.

The vectors can also include transcriptional enhancers, translational signals, and transcriptional and translational termination signals. Examples of transcriptional termination signals include, but are not limited to, polyadenylation signal sequences, such as bovine growth hormone (BGH) poly(A), SV40 late poly(A), rabbit beta-globin (RBG) poly (A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence.

The vectors can include various posttranscriptional regulatory elements. In some embodiments, the posttranscriptional regulatory element can be a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element, and any variants thereof. The RTE can be a rev response element (RRE), for example, a lentiviral RRE. A non-limiting example is bovine immunodeficiency virus rev response element (RRE). In some embodiments, the RTE is a constitutive transport element (CTE). Examples of CTE include, but are not limited to Mason-Pfizer Monkey Virus CTE and Avian Leukemia Virus CTE.

A signal peptide sequence can also be included in the vector to provide for secretion of a polypeptide from a mammalian cell. Examples of signal peptides include, but are not limited to, the endogenous signal peptide for HGH and variants thereof; the endogenous signal peptide for interferons and variants thereof, including the signal peptide of type I, II and III interferons and variants thereof; and the endogenous signal peptides for known cytokines and variants thereof, such as the signal peptide of erythropoietin (EPO), insulin, TGF-β1, TNF, IL1-α, and IL1-β, and variants thereof. Typically, the nucleotide sequence of the signal peptide is located immediately upstream of the heterologous sequence (e.g., fused at the 5' of the coding region of the protein of interest) in the vector. In instances where the vector does not include a heterologous sequence, a signal sequence can be included in the vector downstream of the promoter so that upon insertion of a heterologous sequence, the signal peptide is in-frame with the heterologous sequence.

In further examples, the vectors can contain a regulatory sequence that allows, for example, the translation of multiple proteins from a single mRNA. Non-limiting examples of such regulatory sequences include internal ribosome entry site (IRES) and 2A self-processing sequence, such as a 2A peptide site from foot-and-mouth disease virus (F2A sequence).

The vectors of the present invention can be constructed using known techniques, including, without limitation, the standard techniques of restriction endonuclease digestion, ligation, transformation, plasmid purification, in vitro or chemical synthesis of DNA, and DNA sequencing. The vectors of the present invention may be introduced into a host cell using any method known in the art. Accordingly, the present disclosure is also directed to host cells comprising a vector or nucleic acid described herein.

Recombinant AAV

Also provided are rAAV virions comprising a polypeptide described herein, such as a polypeptide comprising all or a portion of a mAAV-EVE1 capsid protein (e.g. a polypeptide comprising the amino acid sequence set forth in SEQ ID NO:1, 2, 30, 31, 34 or 35 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:1, 2, 30, 31, 34 or 35 or a fragment thereof). The rAAV virions can be produced using the vectors described herein, and methods for producing rAAV having a desired capsid protein are well known in the art. Typically, the rAAV virions will have packaged within them a heterologous sequence as described above.

Typically the methods involve culturing a host cell which contains a nucleic acid molecule encoding an AAV capsid polypeptide (e.g., a nucleic acid molecule encoding a polypeptide comprising the amino acid sequence set forth in SEQ ID NO:1, 2, 30, 31, 34 or 35 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:1, 2, 30, 31, 34 or 35, or a fragment thereof); a functional rep gene; an AAV vector containing AAV ITRs flanking a heterologous sequence; and sufficient helper functions to permit packaging of the AAV vector.

In some embodiments, methods for producing a recombinant AAV include introducing into a packaging cell line a nucleic acid molecule encoding mAAV-EVE1 Cap protein or fragment thereof, a rep gene, an AAV vector, and helper functions for generating a productive AAV infection, and recovering a recombinant AAV from the supernatant of the packaging cell line. Various types of cells can be used as the packaging cell line. For example, packaging cell lines that can be used include, but are not limited to, HEK 293 cells, HeLa cells, and Vero cells, for example as disclosed in US20110201088.

The helper functions may be provided by one or more helper plasmids or helper viruses comprising adenoviral helper genes. Non-limiting examples of the adenoviral helper genes include E1A, BM, E2A, E4 and VA, which can provide helper functions to AAV packaging.

In some embodiments, the nucleic acid encoding a capsid polypeptide of the present disclosure is present in a plasmid. The plasmid can further comprise an AAV rep gene. In some instances, the rep gene is a mAAV-EVE1 rep gene. In other instances, the rep gene is from another AAV serotype, including, but not limited to, AAV1, AAV2, AAV4, AAV5, AAV6, AAV7, AAV8, AAV9, and any variants thereof.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US20110201088, helper vectors pHELP (Applied Viromics). A skilled artisan will appreciate that any helper virus or helper plasmid of AAV that can provide adequate helper function to AAV can be used herein.

In some instances, rAAV virions are produced using a cell line that stably expresses some of the necessary components for AAV virion production. For example, a plasmid (or multiple plasmids) comprising the nucleic acid encoding a capsid polypeptide of the present invention and a rep gene, and a selectable marker, such as a neomycin resistance gene, can be integrated into the genome of a cell (the packaging cells). The packaging cell line can then be transfected with an AAV vector and a helper plasmid or transfected with an AAV vector and co-infected with a helper virus (e.g., adenovirus providing the helper functions). The advantages of this method are that the cells are selectable and are suitable for large-scale production of the recombinant AAV. As another non-limiting example, adenovirus or baculovirus rather than plasmids can be used to introduce the nucleic acid encoding the capsid polypeptide, and optionally the rep gene, into packaging cells. As yet another non-limiting example, the AAV vector is also stably integrated into the DNA of producer cells, and the helper functions can be provided by a wild-type adenovirus to produce the recombinant AAV.

As will be appreciated by a skilled artisan, any method suitable for purifying AAV can be used in the embodiments described herein to purify the recombinant AAV, and such methods are well known in the art. For example, the recombinant AAV can be isolated and purified from packaging cells and/or the supernatant of the packaging cells. In some embodiments, the AAV is purified by separation method using a CsCl gradient. In other embodiments, AAV is purified as described in US20020136710 using a solid support that includes a matrix to which an artificial receptor or receptor-like molecule that mediates AAV attachment is immobilized.

Host Cells

Also provided herein are host cells comprising a nucleic acid molecule, vector or rAAV virion of the present disclosure. In some instances, the host cells are used to amplify, replicate, package and/or purify a polynucleotides, vector or rAAV virion. In other examples, the host cells are used to express a heterologous sequence, such as one packaged within a rAAV virion. Exemplary host cells include prokaryotic and eukaryotic cells. In some instances, the host cell is a mammalian host cell. It is well within the skill of a skilled artisan to select an appropriate host cell for the expression, amplification, replication, packaging and/or purification of a polynucleotide, vector or rAAV virion of the present invention. Exemplary mammalian host cells include, but are not limited to, HEK-293 cells, HeLa cells, Vero cells, HUH7 cells, and HepG2 cells.

Compositions and Methods

Also provided are compositions comprising the nucleic acid molecules, polypeptides and/or rAAV of the present invention. In particular examples, provided are pharmaceutical compositions comprising the recombinant virions disclosed herein and a pharmaceutically acceptable carrier. The compositions can also comprise additional ingredients such as diluents, stabilizers, excipients, and adjuvants.

The carriers, diluents and adjuvants can include buffers such as phosphate, citrate, or other organic acids; antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; mono saccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

The rAAV virions of the present disclosure, and compositions containing the rAAV virions, may be used in methods for the introduction of a heterologous sequence into a host cell. Such methods involve contacting the host cell with the rAAV virion. This may be performed in vitro, ex vivo or in vivo.

When the methods are performed ex vivo or in vivo, typically the introduction of the heterologous sequence into the host cell is for therapeutic purposes, whereby expression of the heterologous sequence results in the treatment of a disease or condition. Thus, the rAAV virions disclosed herein can be administered to a subject (e.g., a human) in need thereof, such as subject with a disease or condition amendable to treatment with a protein, peptide or polynucleotide encoded by a heterologous sequence described herein.

Titers of rAAV virions to be administered to a subject will vary depending on, for example, the particular recombinant virus, the disease or disorder to be treated, the mode of administration, the treatment goal, the individual to be treated, and the cell type(s) being targeted, and can be determined by methods well known to those skilled in the art. Although the exact dosage will be determined on an individual basis, in most cases, typically, recombinant viruses of the present invention can be administered to a subject at a dose of between $1\times10^{10}$ genome copies of the recombinant virus per kg of the subject and $1\times10^{14}$ genome copies per kg.

The route of the administration is not particularly limited. For example, a therapeutically effective amount of the rAAV can be administered to the subject by via, for example, intramuscular, intravaginal, intravenous, intraperitoneal, subcutaneous, epicutaneous, intradermal, rectal, intraocular, pulmonary, intracranial, intraosseous, oral, buccal, or nasal routes. The rAAV can be administrated as a single dose or multiple doses, and at varying intervals.

Capsid Diversification

The nucleic acid molecules of the present invention that encode the capsid polypeptides may be used in techniques for capsid diversification, which produce rAAV with chimeric capsids that contain regions or domains of capsids from multiple serotypes. Exemplary of such techniques are capsid shuffling techniques, which utilize multiple capsid genes that are then "shuffled" to generate a chimeric capsid gene, typically a library of chimeric capsid genes. These can then be used to produce rAAV comprising chimeric capsid proteins. Generally, a library of rAAV is produced, which is then screened to identify capsids and rAAV having desirable traits, such as reduced immunogenicity, reduced cross-reactivity and altered or improved cell tropism. The nucleic acids molecules of the present invention can therefore be used in such methods to produce a chimeric capsid and rAAV comprising the chimeric capsid. Accordingly, the present disclosure is also directed to methods for producing chimeric capsid genes, methods for producing vectors comprising the genes, methods for producing chimeric capsids polypeptides encoded by the genes and methods for producing rAAV comprising the chimeric capsids. Also contemplated are capsid genes, capsid gene libraries, vectors, vector libraries, capsid polypeptides, capsid polypeptide libraries, rAAV and rAAV libraries produced by these methods.

Various capsid shuffling methods have been described in the art. These include "DNA family shuffling" techniques, which have been used to generate diverse libraries of many types of proteins. DNA family shuffling involves in vitro recombination of related genes (in this instance, capsid genes) with >50% homology. The genes are first enzymatically fragmented and then reassembled based on partial homology, resulting in libraries of chimeric genes. DNA family shuffling techniques to produce chimeric capsids have been well described, such as by Grimm et al. (J. Virol. 2008. 82:5887-5911), Koerber et al. (Mol Ther. 2008. 16: 1703-1709), and Li et al. (Mol Ther. 2008. 16: 1252-1260) in U.S. Pat. Nos. 7,588,772 and 9,169,299, and are well known to those of skill in the art. Such methods can be performed using the nucleic acids provided herein that encode a capsid polypeptide of the invention.

Briefly, the methods can include providing two or more different capsid genes from two or more AAV serotypes, wherein one capsid gene encodes a capsid polypeptide of the present disclosure; enzymatically digesting the capsid genes, such as with DNase I, to produce fragments; and reassembling the fragments into chimeric capsid genes which produces a library of chimeric plasmid genes. Reassembly of the gene fragments can be performed by PCR. Because of the related nature of the different capsid genes, the gene fragments have overlapping regions of homology that allow the fragments to self prime in the absence of additional primer in the PCR. Thus, non-primer driven PCR can be used to assemble the fragments into chimeric capsid genes that contain capsid regions from multiple AAV serotypes. In some embodiments, primer-driven PCR is then also used to further amplify the chimeric capsid genes. The method can therefore produce a chimeric capsid gene encoding a chimeric capsid polypeptide that contains a fragment, region or domain of a capsid polypeptide of the present invention. The fragment, region or domain may comprise, for example, one or more of the variable regions (VR), including VR-I, VR-II, VR-III, VR-IV, VR-V, VR-VI, VR-VII, VR-VIII and/or VR-IX, and/or the PLA2 domain, as described above. Typically, a library of chimeric capsid genes is produced.

The chimeric genes can then be inserted into vectors. This can result in the generation of a vector library. The vectors may be, for example, basic plasmids that facilitate subsequent cloning, amplification, replication and/or expression. In other instances, the vectors are AAV vectors that contain AAV ITRs and a rep gene, which facilitate production of rAAV comprising a chimeric capsid protein. The AAV vectors can be introduced into a host cell under conditions that facilitate the production of rAAV virions. Such conditions are well known in the art and are briefly described above. For example, a helper virus or a helper plasmid can be introduced into the host cell with the rAAV vector. In this way, a rAAV virion comprising chimeric capsid polypeptides, such as chimeric capsid polypeptides comprising a fragment, domain or region of a capsid polypeptide of the present invention, may be produced. In instances where a vector library is introduced into host cells, a library of rAAV will be produced.

Other Uses

The mAAV-EVE sequences described herein can also be used for other purposes. For example, the mAAV-EVE nucleic acid sequences, including those set forth in SEQ ID NOs:3-20, 22, 29, 32, 33, 36 or 37 can be used to detect other AAV sequences, such as other endogenous "ancestral" or "fossil" AAV sequences. This detection of other AAV sequences can be achieved using any of the methods known the art, including, but not limited to, the use of polymerase chain reaction (PCR) using AAV-specific primers, or the use of detectable AAV-specific oligonucleotide probes. For example, genomic DNA isolated from cells of animal can be screened for the presence of AAV sequences by PCR using PCR primers (i.e. a 5' primer and a 3' primer) designed using the mAAV-EVE sequences of the present disclosure. The primers have a sequence sufficiently complementary to, or the same as, a sequence flanking a target region within the sequences set forth in SEQ ID NOs:3-20, 22, 29, 32, 33, 36 or 37 such that the primers hybridize to a nucleic molecule containing the AAV target region under high, medium or low stringency conditions. In some examples, the primers have 80%, 81%, 82%, 83%, 84%, 85%, 86%, 87%, 88%, 89%, 90%, 91%, 92%, 93%, 94%, 95%, 96%, 97%, 98% or more sequence identity to a sequence within the sequences set forth in SEQ ID NOs:3-20, 22, 29, 32, 33, 36 or 37 or a reverse, complementary sequence thereto, i.e. the sequences flanking the target region have 80%, 81%, 82%, 83%, 84%, 85%, 86%, 87%, 88%, 89%, 90%, 91%, 92%, 93%, 94%, 95%, 96%, 97%, 98% or more sequence identity to a sequence within the sequences set forth in SEQ ID NOs:3-20, 22, 29, 32, 33, 36 or 37 or a reverse, complementary sequence thereto. Typically, the primers are at least 15, 16, 17, 18, 19, 20, 21, 22, 23, 24, 25, 26, 27, 28, 29, or 30 nucleotides in length. Generally, the primers are from 15 to 40 or from 15 to 30 nucleotides in length. These primers can therefore be used to amplify the corresponding target region in another "ancestral" or "fossil" AAV sequence present in the genomic DNA of an animal cell, i.e. used to generate amplicons containing the target region. Generally, the amplicons are between 50 and 500 nucleic acids in length, such as about 50, 60, 70, 80, 90, 100, 120, 140, 160, 180, 200, 220, 240, 260, 280, 300, 320, 340, 360, 380, 400, 420, 440, 460, 480 or 500 nucleic acids in length. In some embodiments, sequencing of the amplicons is also performed.

Thus, the present disclosure also provides a method for detecting AAV nucleotide sequences in the genomic DNA of an animal cell, comprising performing PCR on the DNA under conditions that allow for specific amplification of a target AAV region with a pair of PCR primers consisting of a first PCR primer (e.g. a 5' primer) and a second PCR primer (e.g. a 3' primer) that are designed to amplify the target AAV region, wherein the first PCR primer and the second PCR primer hybridize to and form a duplex with AAV sequences that flank the target AAV region, wherein the target region corresponds to a region within the sequences set forth in SEQ ID NOs:3-20, 22, 29, 32, 33, 36 or 37 and wherein the presence of amplicons containing the target region and resulting from the PCR indicates that AAV nucleotide sequences have been detected in the DNA.

The mAAV-EVE sequences of the present disclosure can also be used to assign a marsupial species to a tissue sample, i.e. determine which marsupial species selected from *M. robustus, M. rufus, M. parma, M. giganteus, M. eugenii, M. rufogriseus, O. unguifea, S. brachyurus, D. goodfellowi, D. matschiei, P. lateralis, T. stigmatica, L. fasciatus, A. rufescens, P. tridactylus*, and *H. moschatus* a tissue sample is derived from. In such methods, mAAV-EVE sequences are amplified from nucleic acid isolated from the tissue sample using AAV-specific PCR primers so as to produce an amplicon. The amplicon is then sequenced and the sequence compared to the sequences set forth in SEQ ID NOs:5-20 to determine which marsupial species the tissue sample is derived from.

In order that the invention may be readily understood and put into practical effect, particular preferred embodiments will now be described by way of the following non-limiting examples.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Example 1. Identification and Characterization of mAAV-EVE1 Genome and Proteins

A. Materials and Methods
Sample Acquisition

*Macropus giganteus* tissue samples were obtained in accordance with the provisions of a General License issued to the investigators by the NSW National Parks and Wildlife Service (NPWS, License number MWL000100088). All remaining samples were either collected from animals that had succumbed to road trauma, under the provision of a NPWS Scientific License held by the investigators (License number SL100022), or were available from previous studies in the form of purified genomic DNA or liver tissue samples.

Cloning and Sequencing of mAAV-EVE1 Loci

For linker-mediated "genome walking" analysis, genomic DNA was extracted from kangaroo tissue samples (liver, muscle, and brain) using a FastPrep FP120 tissue homogenizer (ThermoSavant) utilizing Lysing Matrix tubes (MP Biochemicals) according to the manufacturer's instructions. Briefly, 50-75 mg of tissue was placed in a 2-ml tube containing MP Lysing Matrix A. To each tube, 360 μl of ATL buffer with proteinase K (DNeasy Blood & Tissue Kit; Qiagen) was added. Tissue was homogenized for 40 seconds at setting 5, followed by centrifugation at 10,000×g for 2 minutes to collect fluid. Samples were incubated at 56° C. for 1 hour, and then centrifuged at 10,000×g for 1 minute. Following centrifugation, 200 μl of the tissue homogenate was applied to a DNeasy column (Qiagen) and processed following the manufacturer's instructions for animal tissue. To obtain endogenous AAV sequences, approximately 0.4 μg of genomic liver DNA was subjected to PCR amplification using Platinum Taq PCR SuperMix (Invitrogen) using combinations of previously reported primer pairs recognizing conserved regions of the AAV genome (primers SIG+ and SIG− and primers AA55 and AA56). The thermal cycling conditions were 94° C. for 5 minutes followed by 35 rounds of 94° C. for 30 seconds, 55° C. for 30 seconds, and 72° C. for 30 seconds, with a final 5 minute extension at 72° C. A positive PCR result was obtained from liver DNA using the following primer pair:

"AA55" 5'-GTGCCCTTCTACGGCTGCGT-CAACTGGACCAATGAGAACTTTCC-3' (SEQ ID NO:23) and "SIG−" 5'-GAATCCCCAGTTGTTGTTGAT-GAGTC-3' (SEQ ID NO:24). Upon identification of an endogenous AAV "anchor sequence", linker-mediated "genome walking" was performed using the GenomeWalker Universal Kit (Clontech) according to the manufacturer's instructions. Briefly, kangaroo liver DNA (2.5 μg) was digested overnight in separate 100-μl reactions containing individual restriction endonucleases (e.g., DraI, NruI, ScaI, or StuI) to yield blunt-ended genomic DNA fragments. The restriction enzyme digest was then heat inactivated at 70° C. for 10 minutes, and the genomic DNA fragments were partially purified using a PCR Kleen Spin column (BioRad). A GenomeWalker kit-provided adapter was ligated to enzyme-digested genomic DNA fragments overnight at 16° C. using T4 DNA ligase. Following heat inactivation (70° C. for 10 minutes), residual adapters were removed by passage over a PCR Kleen Spin column (BioRad) according to manufacturer's instructions. Following nested PCR using unique sequence/adapter-specific primers pairs, amplified PCR products were "TA-cloned" into pCR4-TOPO (Invitrogen). Following bacterial transformation and antibiotic marker selection, individual colonies were expanded in small-scale liquid culture, and plasmid DNA was isolated for sequencing using a QIAprep Spin Kit (Qiagen).

Genomic DNA for amplification across the mAAV-EVE1 locus was extracted from liver tissue samples using either a Gentra Puregene Tissue Kit (Qiagen) or a Blood & Cell Culture DNA Kit with Genomic-tip 100/G (Qiagen), in each case following the manufacturer's protocols for DNA extraction from tissues. Amplification of the locus containing mAAV-EVE1 was initially achieved using a forward primer (AAV-EVE_flank_up, targeting the upstream flanking region: 5'-GATGTTTACAGATTAGTRTTKYAT-CATCAGTGCTATTTYCYCWCAAWRARRATYC C-3'; SEQ ID NO:25) containing multiple degenerate positions to accommodate phylogenetically diverse marsupials, and a reverse primer (AAVEVE_flank_dwn, targeting the downstream flanking region: 5'-AGGGAGAGTACCTATTATCT-TAATTACTGTCAGACC-3'; SEQ ID NO:26). The forward primer includes a 5' non-homologous tail to facilitate reamplification. These primers amplified the locus (irrespective of its mAAV-EVE1 occupancy) from all sampled marsupials. Later, some macropodiform mAAV-EVE1 loci were amplified using a forward primer without degenerate positions (Macr(−335)flank_up: 5'-CCTGGAAT-TTGTGGGTGGAAACAATGATCC-3'; SEQ ID NO: 27), specifically targeted to Macropodiformes. Amplifications were carried out using the Expand Long Template PCR System (Roche) or a LongRange PCR Kit (Qiagen) according to the manufacturers' instructions. Amplicons were gel-extracted using a Wizard SV Gel and PCR Clean-Up System (Promega) and cloned using the TOPO TA Cloning Kit for Sequencing, the Zero Blunt TOPO PCR Cloning Kit for Sequencing (Life Technologies; both in conjunction with One Shot TOP10 Chemically Competent *E. coli* cells), or the pGEM-T Easy Vector System I (Promega; in conjunction with XL10-Gold Ultracompetent Cells [Agilent]). Sanger sequencing of cloned inserts utilized primers directed against the cloning vectors, as well as internal, amplicon-specific primers, using an AB 3730xl instrument (Australian Genome Research Facility). A portion of the cloned mAAV-EVE1 sequences and "empty loci" were amplified using Platinum PCR SuperMix High Fidelity (Invitrogen) in conjunction with primers AAV-EVE_flank_up and AAVEVE_flank_dwn. Amplified sequences were cloned by direct addition of a portion of the final PCR to topo-activated pCR4-TOPO (Invitrogen) without prior gel purification. Cloned fragments were transformed into bacterial strain DH10B (Invitrogen) by electroporation following desalting in a BioRad PCR Kleen Spin column according to manufacturer's instructions. The cloned amplicons were sequenced at the U.S. Food and Drug Administration (FDA) Bethesda campus core facility, or by commercial vendor.

Reconstruction of Ancestral mAAV-EVE1 Sequence

A maximum likelihood algorithm, as implemented in MEGA6.06, was used to infer ancestral mAAV-EVE1 nucleotide sequences from a multiple sequence alignment of sixteen macropodoid mAAV-EVE1 loci (*M. robustus, M. rufus, M. parma, M. giganteus, M. eugenii, M. rufogriseus, O. unguifea, S. brachyurus, D. goodfellowi, D. matschiei, P. lateralis, T. stigmatica, L. fasciatus, A. rufescens, P. tridactylus*, and *H. moschatus*: SEQ ID NOs: 5-20), with the inclusion of "empty" mAAV-EVE1 loci from related non-macropodoid marsupials (*P. breviceps, P. peregrinus, S. maculatus, T. vulpecula, L. latifrons, P. cinereus, D. marsupialis*, and *M. domestica*) serving as an outgroup. Briefly, the twenty-four member dataset was aligned using the MUSCLE multiple sequence alignment algorithm with default settings (gap open penalty=−400; gap extend penalty=0; clustering method (all iterations)=UPGMB; minimum diagonal length (lambda)=24). An isolated alignment of eight outgroup nucleotides (IUPAC nucleotide code: KGRTHACY) extant within the "empty locus" sequences (most likely representing nucleotides lost from the stem-macropodoid locus during the exogenous AAV integration event) was removed from the alignment. A short heterogeneous region of predominantly reiterated guanosine residues occurring within the 5' portion of the mAAV-EVE rep gene was manually aligned. The most appropriate nucleotide substitution model was determined using the "Find Best DNA/Protein Models" function in MEGA, which determines the maximum likelihood fits of twenty-four evolutionary models given the data. For the mAAV-EVE1 dataset, the Tamura 3-parameter model with heterogeneity of substitution rates among sites modeled via a discrete Gamma distribution with five rate categories (i.e., T92+G) gave the lowest Bayesian Information Criterion score (33153.754), and was chosen as the best nucleotide substitution model for further analysis. A mAAV-EVE1 evolutionary tree was constructed in MEGA using the maximum likelihood (ML) method (substitution model=T92+G; gaps/missing data treatment=use all sites; ML heuristic method=nearest-neighbor interchange; initial tree for ML inference was generated automatically by maximum parsimony analysis). Most probable ancestral sequences at each node of the ML tree were exported as a "Detailed Text Export" file from the MEGA6 Tree Explorer module. The most probable ancestral sequences were extracted from the Detailed Text Export file using the command-line utility program, ExtAncSeqME-GA.exe. Due to genomic sequence deletions within mAAV-EVE1 loci occurring within the macropodoid basal taxon, *H. moschatus*, as well as the potoroids (*A. rufescens* and *P. tridactylus*), the full-length inferred mAAV-EVE1 sequence used for ancestral AAV modeling was derived from node 39 of the mAAV-EVE1 evolutionary tree (supplementary fig. S1), occurring at the split between *Lagostrophus fasciatus* and the remainder of the Macropodidae at approximately 13.8 MYA. Reading frames encoding the rep and cap genes within the inferred ancestral sequence were identified by a BLAST search of translated nucleotide databases (tblastx) for significant homology to extant AAV proteins using an ancestral mAAV-EVE1 query sequence. Using homology among the translated mAAV-EVE1 ORFs and extant dependoparvovirus protein sequence alignments as a guide, the raw mAAV-EVE1 ancestral nucleotide sequence was manually edited for frameshifts, nonsense codons, and indels. In all but one instance, frameshifts within the "raw" inferred mAAV-EVE1 nucleotide sequence could be resolved by correction based upon a non-frameshifted member of the dataset. A frameshift occurring within mAAV-EVE rep codon 242 was corrected by arbitrary insertion of a dinucleotide sequence (TT). At various positions, the inferred mAAV-EVE ancestral sequence (Node 39 sequence) was manually edited to give precedence to nucleotides encoding amino acid residues among one or more mAAV-EVE1 sequences homologous with highly conserved extant AAV protein residues.

Building a 3D Structure Model for mAAV-EVE1

The inferred mAAV-EVE1 VP3 sequence was used to generate a 3D structure model with the AAV8 VP3 structure coordinates (RCSB PDB accession No. 2QA0) supplied as a reference template to the SWISS MODEL online 3D modeling server (http://swissmodel.expasy.org/). A comparison of the mAAVEVE1 model to the AAV4 VP3 structure (RCSB PDB accession No. 2G8G) to identify VRs was conducted using the secondary structure matching (SSM) subroutine within PDBeFOld (http://www.ebi.ac.uk/msdsrv/ssm/). VP3 VRs were defined as stretches of two or more sequential Ca positions that are >1 Å apart. The structures were visualized in the COOT program for further comparison of the VRs between mAAV-EVE, AAV2, AAV4, and AAV8. To enable description of the assembled mAAV-EVE1 capsid, the VP3 monomer model was used to generate a 60 mer by icosahedral matrix multiplication in the Viperdb online server (http://viperdb.scripps.edu/oligomer_multi.php). The VP3 and 60 mer coordinates were used to generate secondary structure and capsid surface images, respectively, using the PyMol program.

A. Maximum Likelihood Sequence Reconstruction of an Ancient AAV Genome

A maximum likelihood algorithm, as implemented in MEGA (Kumar et al. 2008), was used to infer ancestral mAAV-EVE1 sequences from a nucleotide alignment of sixteen mAAV-EVE1 loci set forth in SEQ ID NOs: 5-20. The genetic structure of the orthologous mAAV-EVE1 sequences resembles that of contemporary AAVs (FIG. 1). The average size of the "full-length" mAAV-EVE1 virus-derived sequence was approximately 4.4 kbp. The representatives of the family Potoroidae (*A. rufescens* and *P. tridactylus*) bore internal deletions of approximately 1.2 kbp, whereas the EVE recovered from *H. moschatus* (the sole extant member of the family Hypsiprymnodontidae) displayed an internal deletion of 1.6 kbp. Additional minor indels were distributed throughout the various mAAV-EVE1 sequences. The average GC-content of full-length, virus-derived mAAV-EVE1 sequences is approximately 43%, compared to approximately 56%, 54%, and 46% for representative extant primate AAVs (serotypes 1 through 6), avian AAVs (strains DA1 and VR-865), and the goose/Muscovy duck parvoviruses, respectively. The majority of the nucleotide substitutions were single base substitutions. The rep gene of the inferred ancestral mAAV-EVE1 genomic sequence contained three frameshift mutations and five nonsense codons (FIG. 1c). A heterogeneous region of repeated guanosine residues among the mAAV-EVE1 orthologs (resolved to glycine codons 146 and 147 of the inferred mAAV-EVE1 rep ORF) was recalcitrant to unambiguous alignment and was manually edited. The mAAV-EVE1 cap gene of the inferred genome contained three nonsense codons as well as two frameshift mutations (FIG. 1c). A putative TATA box approximately 90 bp upstream of the rep ORF and a putative polyadenylation signal (AATAAA) approximately 40 bp downstream of the cap ORF were identified in locations similar to those mapped in extant AAV genomes. A potential polyadenylation signal was also observed between the rep and cap genes of the mAAV-EVE1 sequences. A similarly located polyadenylation signal occurs within extant primate AAV genomes, and has been shown to be utilized in AAV5 (Qiu et al. 2004. J Virol 78:83-93). ITR sequences were not identified.

To ascertain potential binding sites for known transcription factors and to compare the structure of the mAAV-EVE NS1 promoter to that of an extant dependoparvovirus, the 216-nt sequence extending from the left end of the mAAV-EVE genome to the start codon of the NS1 open reading frame and the equivalent 175-nt region of the AAV2 P5 promoter were analyzed using the web-based software application TFBIND (http://tfbind.hgc.jp). This identified ~300 transcription factor binding site motifs within each promoter (314 motifs within the AAV2 P5 promoter and 297 motifs within the mAAV-EVE NS1 promoter, each with some degree of binding site signature redundancy). The two promoters shared 77 of the transcription factor binding site signature motifs. Notably, putative binding sites for two transacting factors shown to be important for the transcriptional regulation of the AAV2 P5 promoter, viz. YY1 and MLTF/USF, occur at similar locations within each promoter. Similar to the AAV2 P5 promoter, a potential YY1 binding site was identified approximately 25 bp downstream of the putative TATA box of the mAAV-EVE NS1 promoter (although the upstream "−60" YY1 site was not identified). In addition, a potential binding site for MLTF/USF was identified approximately 60 bp upstream of the putative TATA box of the mAAV-EVE1 NS1 promoter, a location similar to the MLTF/USF site mapped approximately 50 bp upstream of the TATA box of the AAV2 P5 promoter (Chang et al. 1989. J Virol 63:3479-88). Potential binding sites for equivalents of the AAV2 P19 and P40 promoters were not analyzed owing to ambiguity as to the potential location of these gene embedded promoters in the absence of transcript mapping data.

Equivalents of the major nonstructural, replication initiator protein (Rep78) and major coat protein (VP3) encoded by the prototypical AAV species (AAV2) were readily apparent (FIG. 1d). The existence of a methionine codon at an equivalent position to the AAV2 Rep52/40 ORF suggests that the exogenous ancestor of mAAV-EVE1 encoded at least one amino-terminally truncated Rep protein. A start codon at an equivalent position to the AAV2 VP1 protein suggests that the ancestral exogenous virus also encoded a VP1-like molecule. An ACG codon at an equivalent position to that utilized by AAV2 for the translational initiation of the VP2 protein was not observed. However, subsequent comparison to other capsid sequences indicated that the VP2 protein initiates at the codon encoding position 132 with a leucyl-tRNA CTG start codon, such that the mAAV-EVE1 VP2 coding sequence is set forth in SEQ ID NO:36.

B. Characterisation of the Rep Protein

The overlapping polypeptides encoded by the AAV rep gene (FIG. 1) are pleiotropic transacting factors shown to possess the nuclease and helicase activities required for initiation (and possibly termination) of AAV DNA replication, as well as packaging of nascent viral genomes. Translation of the mAAV-EVE1 rep open reading frame (ORF) set forth in SEQ ID NO:22) yields an acidic 581 amino acid protein (SEQ ID NO:21; estimated pI 5.2) with a predicted molecular weight of approximately 67.6 kilo daltons (kDa).

A BLAST search of the NCBI non-redundant protein sequences database (nr), using the mAAV-EVE1 Rep protein as a query sequence, identified two conserved protein domains: i) an amino-terminal RepN superfamily catalytic domain associated with DNA binding and ssDNA endonuclease activity; and ii) a central parvovirus_NS1 superfamily domain associated with nucleoside triphosphate hydrolysis and helicase activity (FIG. 2a). The carboxy-terminal domain of mAAV-EVE1 Rep appears unique, with no significant similarity to known protein domains. The top four homologous Rep proteins identified by the BLAST search were encoded by bovine AAV (max score=548), primate AAV5 (max score=543), goat AAV-Go. 1 (max score=542), and avian AAV strain DA-1 (max score=542), respectively. Amino acid alignment of AAV5, AAV2 and mAAV-EVE1 Rep proteins shows retention of clearly identifiable Rolling Circle Replication (RCR) motifs II and III in the N-terminal nuclease domain of the mAAV-EVE1 Rep protein (FIG. 2b). Similar to extant dependoparvovirus Rep proteins, RCR motif I was not apparent. RCR motif II, known as the HUH motif, consists of two invariant histidine residues (positions 95 and 97 of the mAAV-EVE1 Rep protein) embedded within a patch of bulky hydrophobic amino acids (typically uHuHuuu, where u represents a hydrophobic residue).

The crystal structure of the nuclease domain of the AAV5 Rep protein has been solved (Hickman et al. 2002. Rep. Mol Cell 10:327-337). Modeling of the mAAV-EVE1 Rep nuclease domain on a template of AAV5 nuclease atomic coordinates indicates remarkable conservation of domain structure. The AAV Rep nuclease domain fold consists of a five-stranded anti-parallel beta sheet bearing the conserved RCR motifs sandwiched between flanking alpha helical clusters (FIG. 2c). The modeled mAAV-EVE1 Rep nuclease domain shows a high degree of structural similarity to the extant AAV5 domain (QMEAN z-score −0.11), including the juxtaposition of the catalytic RCR motifs within the central cleft of the domain (FIG. 2c). Hickman et al. (2002) noted an acidic 38-amino acid loop between beta strand β1 and alpha helix αB that was a distinctive feature of the AAV5 nuclease domain (FIG. 2c). Although the two regions only share four aligned acidic residues, the relatively large excess negative charge of the loop region is conserved among the mAAV-EVE1 and AAV5 Rep proteins.

The Superfamily 3 helicase domain fold, conserved among extant AAVs and other parvoviruses, was readily apparent within mAAV-EVE1 Rep residues 210 to 495, as were the conserved "Walker motifs" involved in nucleotide triphosphate binding and hydrolysis. The lysine residue of the highly conserved GKT triplet within the Walker A site was substituted with an asparagine residue in the inferred mAAVEVE1 Rep protein. There appears to be no precedent for this substitution in other Walker A site-containing nucleoside triphosphatases. Notably, amino acid substitutions at critical positions of known catalytic sites (e.g., the essential lysine residue of the Rep helicase Walker A site, the catalytic tyrosine residue of the DNA cleavage domain, and the invariant histidine residue of the VP1 phospholipase A2 domain) were observed in many of the individual mAAV-EVE1 Rep and Cap protein sequences. This pattern suggests that expression of active proteins from the endogenized viral sequence could be disadvantageous to host cell function and/or proliferation resulting in selection of function-inactivating mutations.

C. Characterisation of the Capsid Protein

The mAAV-EVE1 capsid gene is a 2196 polynucleotide (SEQ ID NO:3) that, as shown in FIG. 3, encodes a VP1-like protein (SEQ ID NO:1), and a VP3-like protein (SEQ ID NO:2). The VP2-like protein is predicted to span residues 132-731 of the VP1 capsid protein and therefore comprised a sequence set forth in SEQ ID NO:34.

A phospholipase A2 domain (PLA2: amino acid residues 41-100 of SEQ ID NO:1) required for parvovirus infectivity (Zadori et al. 2001. Dev Cell 1L291-302) was conserved within mAAV-EVE1 VP1. However, the otherwise invariant histidine residue at position 71 within the catalytic site of the domain was substituted with a glutamine in mAAV-EVE1 VP1.

Analysis of the mAAV-EVE1 VP3 sequence using BLAST and sequence alignment with AAV2, AAV4, and AAV8 using Clustal W showed the highest sequence identity to AAV2 and AAV8 at ~61% compared to ~55% to AAV4. However, when the SWISS MODEL online subroutine was used to build a VP3 3D structure model for mAAV-EVE1 with AAV2 and AAV8 as reference templates, identities of 63.9% and 65.4%, respectively, were reported. Accordingly, the AAV8-based model was used for further analysis.

Figure 4:
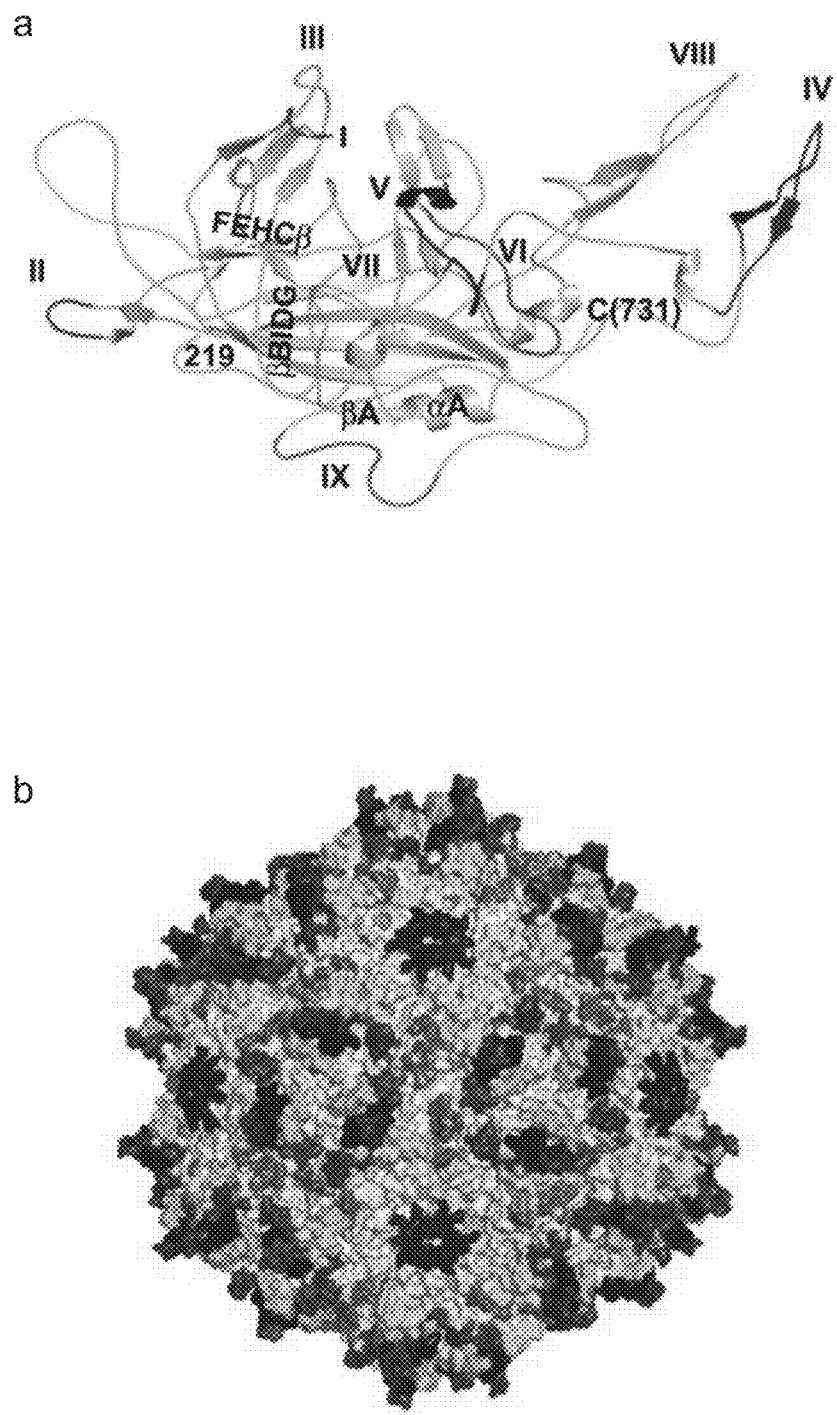
FIG. 4 depicts a mAAV-EVE1 capsid structure. (a) VP3 monomer model of mAAV-EVE1. The nine variable regions (VRs) are color-coded within a grey monomer and labelled. VR-I: purple, VR-II: blue, VR-III: yellow, VR-IV: red, VR-V: black, VR-VI: cerise pink, VR-VII: cyan, VR-VIM green and VR-IX: brown. The core conserved secondary structure elements, the βBIDG and βCHEF β-sheets as well as αA, are labelled. The first N-terminal residue in the model (219) and C-terminal residue (741) are labelled. (b) The mAAV-EVE1 capsid with the VRs coloured as in (a). The HI loops are coloured in wheat. The juxtaposition of the VRs to the most prominent AAV capsid features, for example the 3-fold protrusions by VR-IV, VR-V, and VR-VIII, is evident in this image. The figures were generated using PyMOL.

As has been observed for all the other AAV structures available, the VP3 monomer contains an eight-stranded β-barrel core (βBIDG-CHEF) and the β-strand A with variable loops (in sequence and structure) inserted between the strands and a small a-helix (αA) (FIG. 4). The placement of known regions of amino acid variability associated with surface loops (regions I through IX) were consistent with those of extant AAV capsids (FIG. 4a). These regions are located at or near the exterior surface of the VP3 monomer (FIG. 4a). Interestingly, VR-VII was substantially larger in mAAV-EVE1 compared to AAV2 and AAV8 (FIG. 3). The mAAV-EVE1 capsid, assembled from 60 copies of the VP3 common region of the VP, conserves the characteristic features of the AAVs: a depression at the icosahedral 2-fold axis, three protrusions surrounding an icosahedral 3-fold axis, a channel at the icosahedral 5-fold axis, and an HI loop (between βH and βI) lining a depression surrounding the 5-fold channel. The VRs cluster on the mAAV-EVE1 capsid surface to create local surface topology differences compared to other AAVs (FIG. 6b). For example, the larger VR-VII is located at the base of the 3-fold protrusions and extends into the depression surrounding the 5-fold channel creating a unique surface topology in mAAVEVE1. These VRs control several AAV functions, including receptor attachment, trafficking phenotypes, transduction efficiency, and antigenic reactivity (Parrish 2010. Curr Top Microbiol Immunol 343:149-176; Halder et al. 2012. Future Virol 7:253-278).

An AAG-initiated open reading frame encoding a potential assembly-activating protein (AAP: SEQ ID NO:29) homolog, a protein involved in AAV capsid assembly (Sonntag et al. (2010) Proc Natl Acad Sci USA 107:10220-10225), was embedded within the cap gene (FIG. 1d). Assuming that, similar to numerous extant AAVs, translational initiation of the AAP ORF begins at a non-canonical CTG codon (Naumer et al. 2012. J Virol 86:13038-13048; Pénzes et al. 2015. J Gen Virol 96:2769-2779), the putative mAAV-EVE AAP is 201 amino acids in length with a molecular weight of approximately 21.6 kDa and a predicted pI of 8.30 (SEQ ID NO:28). The protein sequence demonstrates evolutionarily-conserved characteristic features of the AAP family, including a conserved core sequence flanked by hydrophobic and proline-rich regions respectively, followed by a region rich in serine/threonine residues (Naumer et al. (2012) J Virol 86:13038-13048; Pénzes et al. (2015) J Gen Virol 96:2769-2779).

Example 2. Modification of mAAV-EVE Capsid

The mAAV-EVE1 capsid protein was modified in silico to include residues that were evolutionarily conserved between phylogenetically divergent AAV serotypes. Positions within the mAAV-EVE1 capsid sequence set forth ion SEQ ID NO:1 that were not in agreement with the conserved sequences were evaluated, and changed where deemed appropriate, based on tiered criteria: 1) if any of the individual macropodiform AAV-EVE sequences (from which mAAV-EVE1 was deduced, i.e. polypeptides encoded by SEQ ID NOs:5-20) supported the conserved sequence, the corresponding residue was changed; 2) if criterion 1 did not apply, but additional contemporary/extant marsupial AAV sequences supported the conserved sequence, the corresponding residue was changed; 3) if neither criterion 1 nor 2 applied, but a single nucleotide substitution could be used to effect an amino acid change to match the conserved sequence, the corresponding residue was changed. Residues that were not in agreement with conserved positions but could not be changed in accordance with any of the three criteria above were left unchanged.

The above process produced the mAAV-EVE1 capsid protein (VP1) set forth in SEQ ID NO:30, which has 96.17% sequence identity to the originally-deduced mAAV-EVE1 capsid polypeptide set forth in SEQ ID NO:1 (see FIG. 5). An exemplary encoding capsid gene is set forth in SEQ ID NO:32. The VP3 of this deduced, modified mAAV-EVE1 capsid is set forth in SEQ ID NO:31 (exemplary encoding polynucleotide set forth in SEQ ID NO: 33), and the VP2 is set forth in SEQ ID NO:35 (exemplary encoding polynucleotide set forth in SEQ ID NO: 37).

Example 3. Production of rAAV

The mAAV-EVE1 cap gene set forth in SEQ ID NO:1 or SEQ ID NO:30 is cloned into an AAV2 Rep-expressing plasmid, downstream of the rep gene. This plasmid is co-transfected into HEK293T cells with a transgene plasmid (AAV vector) containing AAV ITRs flanking the GFP gene and pAd5 in a ratio of 1:1:3 using polyethylenimine (PEI) The plasmids are added to 80-90% confluent HEK293 cells in 10% DMEM+1% penicillin/streptomycin. Briefly, for each plate of cells, DNA is to pre-warmed OptiMem medium (final volume 250 µL; 7.5 µg Rep+Cap-expressing plasmid: 7.5 µg AAV vector: 22.5 pAd5). 150 µL PEI (1 µg/µL in 1×PBS pH 4.5) is added to 100 µL pre-warmed OptiMem (4:1 ratio of PEI:DNA) and briefly vortexed (10 sec). Both solutions are mixed, vortexed briefly and left for 10 min at room temperature. Cells are harvested at 72 hours post transfection by washing the plates with the media in the plate. Cells are pooled in 2×500-mL Corning tubes and centrifuged for 15 min at 3800 rpm.

The supernatant is moved to new 500-mL tubes and the cell pellets are resuspended in 30-40 mL benzonase buffer. The supernatant is centrifuged again before being transferred into a 1000-mL single use bottle, and ¼ volume 40% PEG in 2.5 M NaCl is added. The supernatant/PEG solution is incubated on ice for at least 3 hrs before being mixed and moved into 500-mL Corning tubes. The tube is centrifuged for 30 min at 3800 rpm at 4° C. and the resulting PEG pellet is resuspended in 20 mL 1× cracking buffer by rotating the tube at 4° C. overnight. This preparation is maintained at 4° C. for further AAV purification (below).

The cells are lysed using 3 freeze-thaw cycles. The cell suspension is frozen in dry ice/EtOH and the tube is placed in a 37° C. water bath until the cells are completely thawed. After the second thaw, benzonase enzyme is added at 200 U/ml and the cells are frozen again before being thawed a third time with benzonase. After 1 hr incubation at 37° C., the cells are spun at 3000-4000 rpm for 15 min to pellet the cell debris, and the supernatant is transferred to a new tube. To the supernatant, 1/39th volume 1 M $CaCl_2$ is added to obtain a 25 mM $CaCl_2$ final solution, which is then kept on ice for 1 hour. The solution is centrifuged at maximum speed for 30 min at 4° C. and the supernatant is added to a new tube. One quarter volume 40% PEG-8000/2.5 M NaCl (final 8% PEG) is added and mixed well before the tube is incubated on ice for at least 3 hrs. The solution is centrifuged at maximum speed for 30 min at 4° C. and the supernatant is discarded. The pellet is resuspended in 10 ml NaHepes/EDTA resuspension buffer, to which a further 10 ml more buffer is added before being left overnight at 4° C. shaking.

To purify the AAV from the cell pellet preparation and the supernatant preparation, each preparation is treated as follows: Twelve mL of 1.3 g/mL CsCl in PBS is added to a 30 ml SW28 tube. A further 5 mL of 1.5 g/mL CsCl in PBS is added to the bottom of the tube to establish a clear interface. To this, 20-22 mL of virus suspension is slowly added at the top. The tube is centrifuged and at 28K (104,000×g) at 20° C. for 24 hrs and the virus band at the interface is collected using a 10-mL syringe/18G needle. The virus suspension is pooled and a second CsCl gradient is performed by adjusting the suspension to 1.37 g/mL CsCl in PBS centrifuging at 38K for 24 hrs. Full virions are then collected by sealing the top of the tube with Parafilm and collect 0.5-mL fractions by piercing the bottom of the tube. The presence of rAAV in each fraction is confirmed by SDS gel and qPCR on 1 µl from each dilution for each fraction, and the fractions with full rAAV are pooled.

The rAAV is the dialysed with PBS pH 7.4 using Slide-a-lyzer dialysis cassettes (10,000 MWCO, 0.5-3.0 ml capacity: Pierce) at 4° C. Briefly, the cassette is pre-wet in the buffer for at least 2 min, with foam float and rAAV is added to the cassette with 1 mL pipette using the pipette port. The rAAV is dialysed in PBS for 2 hrs or overnight, then in fresh PBS for 2 hrs. A third dialysis for 2 hrs in PBS/5% sorbitol is performed before the rAAV is removed from the cassette using a syringe. The virus is filtered through a 0.22-m syringe filter into a 15-ml Falcon tube or 5-mL Eppendorf tube and stores at −80° C.

Example 4. Assessment of rAAV

The functionality of the rAAV containing the mAAV-EVE1 capsid polypeptides is assessed by transducing human and mouse cells with the rAAV and determining capsid tropism. Briefly, a panel of human cell lines representing the broadest possible range of tissues is transduced with a vector encoding GFP and packaged using the mAAV-EVE capsid. GFP expression is then assessed by fluorescence microscopy and by FACS. For mouse cell targeting, C57BL/6 mice are injected via the tail vein with a similar vector encoding both luciferase and GFP, separated by a 2A peptide sequence. Whole-body bioluminescent imaging is used to detect luciferase expression, while specific tissues from sacrificed mice are assessed for GFP expression by fluorescence microscopy and FACS.

The invention claimed is:

1. An isolated capsid polypeptide, comprising a sequence having at least 95% sequence identity to the sequence set forth in SEQ ID NO:2.

2. The isolated capsid polypeptide of claim 1, comprising the sequence of amino acids set forth in SEQ ID NO:1 or a sequence having at least 95% sequence identity to the sequence set forth in SEQ ID NO:1.

3. The isolated capsid polypeptide of claim 1, wherein the sequence having at least 95% sequence identity to the sequence set forth in SEQ ID NO: 1 comprises:
   (a) a region selected from the group consisting of:
      (i) a phospholipase A2 (PLA2) domain set forth in amino acid residues 41-100 of SEQ ID NO:1;
      (ii) a VR-I set forth in amino acid residues 250-259 of SEQ ID NO:1;
      (iii) a VR-II set forth in amino acid residues 313-318 of SEQ ID NO:1;
      (iv) a VR-III set forth in amino acid residues 368-376 of SEQ ID NO:1;
      (v) a VR-IV set forth in amino acid residues 436-454 of SEQ ID NO:1;
      (vi) a VR-V set forth in amino acid residues 473-489 of SEQ ID NO:1;
      (vii) a VR-VI set forth in amino acid residues 510-528 of SEQ ID NO:1;
      (viii) a VR-VII set forth in amino acid residues 531-552 of SEQ ID NO:1;
      (ix) a VR-VIII set forth in amino acid residues 575-590 of SEQ ID NO:1; and
      (x) a VR-IX set forth amino acid residues 700-707 of SEQ ID NO:1; or
   (b) the sequence set forth in SEQ ID NO:1;
   (c) the sequence set forth in SEQ ID NO:2;
   (d) the sequence set forth in SEQ ID NO:30; or
   (e) the sequence set forth in SEQ ID NO:31.

4. A recombinant AAV (rAAV) virion, comprising the capsid polypeptide of claim 1.

5. The rAAV of claim 4, further comprising a heterologous sequence.

6. A nucleic acid molecule encoding the capsid polypeptide of claim 1.

7. The nucleic acid molecule of claim 6, comprising the sequence set forth in SEQ ID NO:3 or a sequence having at least 95% sequence identity to the sequence set forth in SEQ ID NO:3.

8. A vector comprising the nucleic acid molecule of claim 6.

9. The vector of claim 8, wherein the vector is selected from the group consisting of a plasmid, a cosmid, a phage, a transposon and a viral vector.

10. The vector of claim 9, wherein the viral vector is selected from the group consisting of an adeno-associated viral (AAV), a lentiviral, a retroviral, an adenoviral, a herpesviral, a hepatitis viral and a baculoviral vector.

11. An isolated host cell, comprising the rAAV of claim 4.

12. A method for introducing a heterologous sequence into an isolated host cell, comprising contacting the host cell with the rAAV of claim 5.

13. A method for producing a chimeric capsid gene, comprising:
   (a) providing two or more AAV capsid genes from two or more serotypes of AAV, wherein at least one capsid gene encodes a capsid polypeptide of claim 1;
   (b) digesting the AAV capsid genes into fragments; and
   (c) reassembling the fragments to form a chimeric capsid gene.

14. The method of claim 13, wherein a library of chimeric capsid genes is produced.

15. The method of claim 13, further comprising inserting the chimeric capsid gene into a vector.

16. The method of claim 15, wherein the vector is an AAV vector.

17. The method of claim 15, wherein a library of vectors is produced.

18. The method of claim 17, further comprising introducing the AAV vector into an isolated host cell under conditions sufficient to produce a rAAV virion, thereby producing a rAAV virion comprising a chimeric capsid.

19. The method of claim 18, wherein a library of rAAV virions is produced.

20. A method for producing a rAAV virion, comprising:
   (a) introducing into a cell the nucleic acid molecule of claim 6, an AAV rep gene, an AAV vector comprising a heterologous sequence flanked by inverted terminal repeats, and helper functions for generating a productive AAV infection; and
   (b) allowing assembly of an rAAV virion comprising a capsid encoded by the nucleic acid molecule of claim 6, wherein the capsid encapsidates the heterologous sequence.

21. The isolated capsid polypeptide of claim 3, comprising a plurality of regions selected from the group consisting of (i)-(x).

* * * * *